United States Patent
Takami et al.

(10) Patent No.: US 12,378,256 B2
(45) Date of Patent: *Aug. 5, 2025

(54) HETEROCYCLIC COMPOUND

(71) Applicant: Takeda Pharmaceutical Company Limited, Osaka (JP)

(72) Inventors: Kazuaki Takami, Kanagawa (JP); Masaki Seto, Kanagawa (JP); Shinobu Sasaki, Kanagawa (JP); Haruhi Ando, Tokyo (JP); Masaki Ogino, Kanagawa (JP); Tomoko Ohashi, Kanagawa (JP); Toshihiro Imaeda, Kanagawa (JP); Ikuo Fujimori, Tokyo (JP); Yasuhiro Tsukimi, Kanagawa (JP); Masami Yamada, Kanagawa (JP); Kenichiro Shimokawa, Kanagawa (JP); Takeshi Wakabayashi, Kanagawa (JP); Masataka Murakami, Kanagawa (JP); Makoto Fushimi, New York, NY (US); Tomohiro Okawa, Kanagawa (JP); Jinichi Yonemori, Kanagawa (JP); Tomohiro Ohashi, Kanagawa (JP); Hideo Suzuki, Kanagawa (JP); Hironobu Maezaki, Kanagawa (JP); Ayumu Sato, Kanagawa (JP); Yasutomi Asano, Kanagawa (JP); Steve Swann, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 579 days.

This patent is subject to a terminal disclaimer.

(21) Appl. No.: 17/475,733

(22) Filed: Sep. 15, 2021

(65) Prior Publication Data

US 2022/0017530 A1 Jan. 20, 2022

Related U.S. Application Data

(63) Continuation of application No. 16/622,632, filed as application No. PCT/JP2018/023357 on Jun. 19, 2018, now Pat. No. 11,236,099.

(60) Provisional application No. 62/683,418, filed on Jun. 11, 2018.

(30) Foreign Application Priority Data

Jun. 20, 2017 (JP) .................................. 2017-120859
Jan. 17, 2018 (JP) .................................. 2018-005960

(51) Int. Cl.
  *C07D 491/048* (2006.01)
  *A61K 31/4355* (2006.01)
  *A61P 1/10* (2006.01)

(52) U.S. Cl.
  CPC ...... *C07D 491/048* (2013.01); *A61K 31/4355* (2013.01); *A61P 1/10* (2018.01)

(58) Field of Classification Search
  None
  See application file for complete search history.

(56) References Cited

U.S. PATENT DOCUMENTS

| | | | |
|---|---|---|---|
| 9,315,458 B2 | 4/2016 | Yamada et al. |
| 9,403,802 B2 | 8/2016 | Sakamoto et al. |
| 9,499,516 B2 | 11/2016 | Yamada et al. |
| 9,518,042 B2 | 12/2016 | Yamada et al. |
| 9,655,881 B2 | 5/2017 | Yamada et al. |
| 9,662,316 B2 | 5/2017 | Yamada et al. |
| 9,675,597 B2 | 6/2017 | Yamada et al. |
| 9,775,827 B2 | 10/2017 | Yamada et al. |
| 9,777,005 B2 | 10/2017 | Sugimoto et al. |
| 9,789,083 B2 | 10/2017 | Yamada et al. |
| 9,789,084 B2 | 10/2017 | Yamada et al. |
| 9,868,725 B2 | 1/2018 | Yamada et al. |
| 9,878,989 B2 | 1/2018 | Sugimoto et al. |

(Continued)

FOREIGN PATENT DOCUMENTS

| | | |
|---|---|---|
| JP | 2006-045220 | 2/2006 |
| JP | 2013-514358 | 4/2013 |

(Continued)

OTHER PUBLICATIONS

Stahl and Wermuth, Handbook of Pharmaceutical Salts: Properties, Selection, and Use, Chapter 12 "Selected Procedures for the Preparation of Pharmaceutically Acceptable Salts," 2011, 307-325.

(Continued)

*Primary Examiner* — Po-Chih Chen
(74) *Attorney, Agent, or Firm* — Foley & Lardner LLP

(57) ABSTRACT

The present invention aims to provide a compound that may be useful for the prophylaxis or treatment of constipation and the like. The present invention provides a compound represented by the following formula (I):

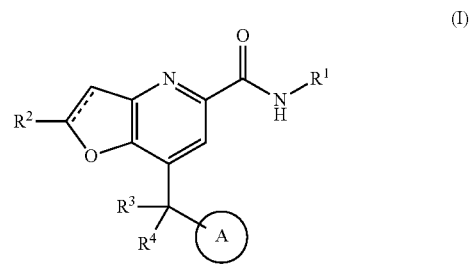

wherein each symbol is as described in the specification, or a salt thereof.

17 Claims, No Drawings

(56) References Cited

U.S. PATENT DOCUMENTS

| | | |
|---|---|---|
| 10,087,150 B2 | 10/2018 | Sugimoto et al. |
| 10,208,046 B2 | 2/2019 | Sugimoto et al. |
| 10,214,508 B2 | 2/2019 | Ogino et al. |
| 10,323,027 B2 | 6/2019 | Sugimoto et al. |
| 10,428,056 B2 | 10/2019 | Sugimoto et al. |
| 10,457,670 B2 | 10/2019 | Yamada et al. |
| 10,548,877 B2 | 2/2020 | Ogino et al. |
| 10,548,899 B2 | 2/2020 | Sugimoto et al. |
| 2012/0252808 A1 | 10/2012 | Kuduk et al. |
| 2015/0126487 A1 | 5/2015 | Sakamoto et al. |
| 2015/0307451 A1 | 10/2015 | Yamada et al. |
| 2015/0307497 A1 | 10/2015 | Sugimoto et al. |
| 2016/0075656 A1 | 3/2016 | Kuduk et al. |
| 2016/0152598 A1 | 6/2016 | Yamada et al. |
| 2016/0152603 A1 | 6/2016 | Yamada et al. |
| 2016/0376244 A1 | 12/2016 | Sugimoto et al. |
| 2017/0027921 A1 | 2/2017 | Yamada et al. |
| 2017/0044143 A1 | 2/2017 | Yamada et al. |
| 2017/0081332 A1 | 3/2017 | Sugimoto et al. |
| 2017/0100373 A1 | 4/2017 | Yamada et al. |
| 2017/0100384 A1 | 4/2017 | Yamada et al. |
| 2017/0121308 A1 | 5/2017 | Ogino et al. |
| 2017/0216255 A1 | 8/2017 | Yamada et al. |
| 2017/0258764 A1 | 9/2017 | Yamada et al. |
| 2017/0266162 A1 | 9/2017 | Yamada et al. |
| 2018/0000780 A1 | 1/2018 | Yamada et al. |
| 2018/0050996 A1 | 2/2018 | Sugimoto et al. |
| 2018/0162850 A1 | 6/2018 | Sugimoto et al. |
| 2018/0303841 A1 | 10/2018 | Sugimoto et al. |
| 2018/0346452 A1 | 12/2018 | Yamada et al. |
| 2018/0362516 A1 | 12/2018 | Sugimoto et al. |
| 2019/0083467 A1 | 3/2019 | Ogino et al. |
| 2019/0241547 A1 | 8/2019 | Yamada et al. |
| 2019/0248776 A1 | 8/2019 | Sugimoto et al. |

FOREIGN PATENT DOCUMENTS

| | | | |
|---|---|---|---|
| RU | 2482850 C2 | | 5/2013 |
| WO | WO-2004/089350 A1 | | 10/2004 |
| WO | 2011/084368 | | 7/2011 |
| WO | 2011/159554 | | 12/2011 |
| WO | 2012/158474 | | 11/2012 |
| WO | 2013/129622 | | 9/2013 |
| WO | 2014/077401 | | 5/2014 |
| WO | 2015/163485 | | 10/2015 |
| WO | 2015/174534 | | 11/2015 |
| WO | 2015/190564 | | 12/2015 |
| WO | 2016/009297 | | 1/2016 |
| WO | 2016/208775 | | 12/2016 |
| WO | 2017/069173 | | 4/2017 |
| WO | 2017/143041 | | 8/2017 |
| WO | 2017155050 | | 9/2017 |
| WO | 2018/042362 | | 3/2018 |
| WO | WO2018042632 | * | 3/2018 |
| WO | 2018/063552 | | 4/2018 |
| WO | 2018/194181 | | 10/2018 |

OTHER PUBLICATIONS

Horig et al., "From Bench to Clinic and Back: Perspective on the 1st IQPC Translational Research Conference", Journal of Translational Medicine, Dec. 20, 2004, 2(44):1-8.

Pustovit et al., "Muscarinic receptor 1 allosteric modulators stimulate colorectal emptying in dog, mouse and rat and resolve constipation", Neurogastroenterology & Motility, 2019, 31:e13692, 2 pages, abstract.

Schafer et al., "Failure is an option: Learning From Unsuccessful Proof-Of-Concept Trials," Drug Discovery Today, Nov. 2008, 13(21/22):913-916.

Belikov, V.G., "Relationships between the Chemical Structure, Properties of the Compound, and Its Effect on a Living Body," Pharmaceutical Chemistry, Moscow: MEDpress-Inform, 2007, Chapter 2.6:27-29.

Berge et al., "Pharmaceutical Salts", Journal of Pharmaceutical Sciences, Jan. 1977, 66(1):1-19.

Rook, J. M. et al., "Diverse Effects on M1 Signaling and Adverse Effect Liability within a Series of M1 Ago-PAMs", ACS Chemical Neuroscience, 2017 [published online Dec. 21, 2016], vol. 8, No. 4, pp. 866-883.

Harrington A.M. et al., "Immunohistochemical localisation of cholinergic muscarinic receptor subtype 1 (M1r) in the guinea pig and human enteric nervous system", Journal of Chemical Neuroanatomy, 33:193-201, 2007.

Adachi Y. et al., "Comparative Studies on in Vitro Methods for Evaluating in Vivo Function of MDR1 P-Glycoprotein", Pharm. Res. 18:1660-1668, 2001.

Takeuchi T. et al., "Establishment and Characterization of the Transformants Stably-Expressing MDR1 Derived from Various Animal Species in LLC-PK1", Pharm. Res., 23(7):1460-1472, 2006.

Sugimoto H. et al., "Quantitative Investigation of the Impact of P-Glycoprotein Inhibition on Drug Transport across Blood-Brain Barrier in Rats", Drug Metab. Dispos., 39(1):8-14, 2011.

International Search Report issued in International Application No. PCT/JP2018/023357, Aug. 14, 2018, 2 pages.

English Translation of the Written Opinion of the International Searching Authority issued in International Application No. PCT/JP2018/023357, Aug. 14, 2018, 5 pages.

* cited by examiner

HETEROCYCLIC COMPOUND

CROSS-REFERENCE TO RELATED APPLICATIONS

This application is a Continuation of U.S. application Ser. No. 16/622,632, which is the the U.S. National Stage of PCT/JP2018/023357, filed Jun. 19, 2018, which claims priority from U.S. Provisional Application No. 62/683,418, filed Jun. 11, 2018, JP 2017-120859, filed Jun. 20, 2017, and JP 2018-005960, filed Jan. 17, 2018.

TECHNICAL FIELD

The present invention relates to a heterocyclic compound possibly having a cholinergic muscarinic M1 receptor positive allosteric modulator activity and possibly useful as a medicament such as a prophylactic or therapeutic drug for constipation and the like. As used herein, the positive allosteric modulator activity refers to an action to potentiate receptor function by binding to a moiety different from that of an endogenous activator (acetylcholine for this receptor).

BACKGROUND OF THE INVENTION

Acetylcholine is a neurotransmitter that induces signal transduction in the central nervous system and the neuromuscular connections (the parasympathetic nerve and motor nerve). In the gastrointestinal tract, myenteric plexus, submucosal plexus and the like form a neural network and control gastrointestinal function. Of these, acetylcholine is a major neurotransmitter in the gastrointestinal function and plays a key role in the gastrointestinal motility.

Acetylcholine receptor is classified into a ligand dependent ion channel (cholinergic nicotinic receptor) and a G-protein-conjugated receptor (cholinergic muscarinic receptor). The cholinergic muscarinic receptor is one kind of receptor for excitatory neurotransmitter acetylcholine, and was named based on the selective activation of the receptor by muscarine. The muscarinic receptor is further classified into subtypes of M1 to M5, and the M1 receptor is known to be widely distributed mainly in the brain. On the other hand, expression of M1 receptor in the gastrointestinal nerve plexus is also known and its role of regulating the functions of the gastrointestinal tract has been pointed out (non-patent document 1). From the studies in recent years, promotion of gastrointestinal motility by cholinergic M1 receptor agonist has also been reported.

Generally, peristalsis in the gastrointestinal tract consists of coordinated contraction and relaxation at adjacent sites. It is also known that the cholinergic M1 receptor is expressed in both the excitatory nerve and inhibitory nerve in the gastrointestinal nerve plexus (non-patent document 1).

WO2013/129622 (patent document 1) discloses the following compound having a cholinergic muscarinic M1 receptor positive allosteric modulator (M1PAM) activity and useful for the treatment of Alzheimer's disease, schizophrenia, pain, sleep disorder and the like.

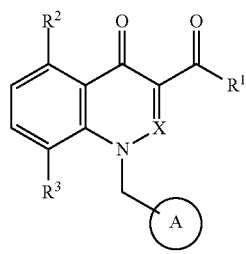

wherein each symbol is as defined in the document.

WO2014/077401 (patent document 2) discloses the following compound having an M1PAM activity and useful for the treatment of Alzheimer's disease, schizophrenia, pain, sleep disorder and the like.

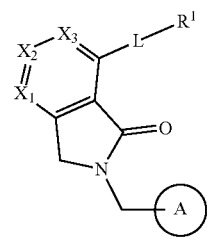

wherein each symbol is as defined in the document.

WO2015/174534 (patent document 3) discloses the following compound having an M1PAM activity and useful for the treatment of Alzheimer's disease, schizophrenia, pain, sleep disorder, Parkinson's disease dementia, Lewy body dementia and the like.

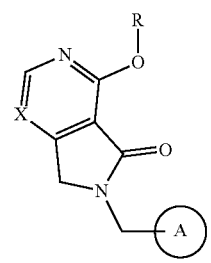

wherein each symbol is as defined in the document.

WO2015/163485 (patent document 4) discloses the following compound having an M1PAM activity and useful for the treatment of Alzheimer's disease, schizophrenia, pain, sleep disorder, Parkinson's disease dementia, Lewy body dementia and the like.

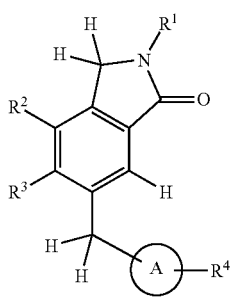

wherein each symbol is as defined in the document.

WO2016/208775 (patent document 5) discloses the following compound having an M1PAM activity and useful for the treatment of Alzheimer's disease, schizophrenia, pain, sleep disorder, Parkinson's disease dementia, Lewy body dementia and the like.

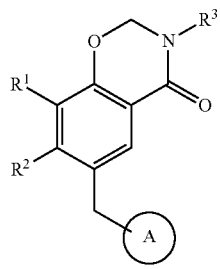

wherein each symbol is as defined in the document.

WO2015/190564 (patent document 6) discloses the following compound having an M1PAM activity and useful for the treatment of Alzheimer's disease, schizophrenia, pain, sleep disorder, Parkinson's disease dementia, Lewy body dementia and the like.

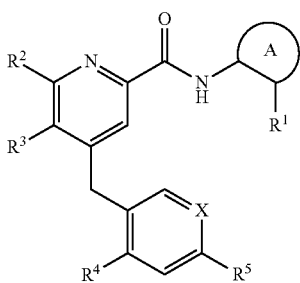

wherein each symbol is as defined in the document.

DOCUMENT LIST

Patent Documents patent document 1: WO2013/129622
patent document 2: WO2014/077401
patent document 3: WO2015/174534
patent document 4: WO2015/163485
patent document 5: WO2016/208775
patent document 6: WO2015/190564

Non-Patent Document non-patent document 1: Journal of Chemical Neuroanatomy, 2007 July, 33(4), 193-201

SUMMARY OF THE INVENTION

Problems to be Solved by the Invention

The development of a compound having a cholinergic muscarine M1 receptor (M1 receptor) positive allosteric modulator activity and useful as a prophylactic or therapeutic agent for constipation, for example, constipation associated with neurological disease (e.g., Parkinson's disease, spinal cord injury, multiple sclerosis), idiopathic constipation, age-related constipation, opioid-induced constipation and the like is desired. As used herein, the positive allosteric modulator activity means an action to bind to a site different from an endogenous activator (acetylcholine in this receptor) and potentiate the receptor function.

Means of Solving the Problems

The present inventors have conducted intensive studies in an attempt to solve the aforementioned problems and found that a compound represented by the following formula (I) may have a cholinergic muscarinic M1 receptor positive allosteric modulator activity, which resulted in the completion of the present invention.

Therefore, the present invention relates to the following.

[1] A compound represented by the formula (I):

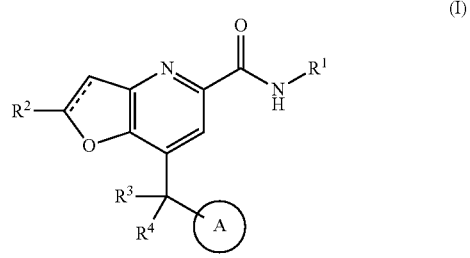

wherein
R$^1$ is an optionally substituted cyclic group;
R$^2$ is a hydrogen atom, a halogen atom, a cyano group, an optionally substituted C$_{1-6}$ alkyl group, or an optionally substituted C$_{1-6}$ alkoxy group;

$=$ is a single bond or a double bond;
ring A is an optionally further substituted ring; and
R$^3$ and R$^4$ are each independently a hydrogen atom, a halogen atom, a hydroxy group, an optionally substituted C$_{1-6}$ alkyl group, or an optionally substituted C$_{1-6}$ alkoxy group, or a salt thereof (sometimes to be abbreviated as "compound (I)" in the present specification).

[2] The compound described in the above-mentioned [1], wherein
R$^1$ is
(1) an optionally substituted 3- to 14-membered non-aromatic heterocyclic group, or
(2) an optionally substituted C$_{3-10}$ cycloalkyl group;

$R^2$ is a hydrogen atom or an optionally substituted $C_{1-6}$ alkyl group;

ring A is
  (1) an optionally further substituted benzene ring,
  (2) an optionally further substituted 5- or 6-membered monocyclic aromatic heterocycle,
  (3) an optionally further substituted 4- to 6-membered monocyclic non-aromatic heterocycle, or
  (4) an optionally further substituted 9- to 14-membered fused polycyclic non-aromatic heterocycle; and $R^3$ and $R^4$ are each independently a hydrogen atom, a halogen atom or an optionally substituted $C_{1-6}$ alkyl group, or a salt thereof.

[3] The compound described in the above-mentioned [1], wherein
  $R^1$ is
    (1) a 3- to 14-membered non-aromatic heterocyclic group optionally substituted by 1 to 3 hydroxy groups, or
    (2) a $C_{3-10}$ cycloalkyl group optionally substituted by 1 to 3 substituents selected from a hydroxy group and a halogen atom;
  $R^2$ is a hydrogen atom or a $C_{1-6}$ alkyl group;
  ring A is
    (1) a benzene ring optionally further substituted by 1 to 3 substituents selected from (a) a halogen atom, (b) a $C_{1-6}$ alkoxy group, (c) a mono- or di-$C_{1-6}$ alkyl-carbamoyl group optionally substituted by 1 or 2 substituents selected from (i) a $C_{1-6}$ alkoxy group, (ii) a $C_{3-10}$ cycloalkyl group, (iii) a 3- to 14-membered non-aromatic heterocyclic group, (iv) a $C_{6-14}$ aryl group optionally substituted by 1 to 3 hydroxy groups, (v) a $C_{1-6}$ alkoxy-carbonyl group, (vi) a carboxy group, (vii) a $C_{1-6}$ alkylthio group, (viii) a mono- or di-$C_{1-6}$ alkyl-carbamoyl group, and (ix) a 3- to 14-membered non-aromatic heterocyclylcarbonyl group, (d) a mono- or di-$C_{3-10}$ cycloalkyl-carbamoyl group, (e) a $C_{6-14}$ aryl-carbamoyl group optionally substituted by 1 to 3 hydroxy groups, and (f) a 5- to 14-membered aromatic heterocyclic group optionally substituted by 1 to 3 $C_{1-6}$ alkyl groups,
    (2) a 5- or 6-membered monocyclic aromatic heterocycle optionally further substituted by 1 to 3 substituents selected from (a) a $C_{1-6}$ alkoxy group and (b) a 5- to 14-membered aromatic heterocyclic group optionally substituted by 1 to 3 $C_{1-6}$ alkyl groups,
    (3) a 4- to 6-membered monocyclic non-aromatic heterocycle optionally further substituted by one oxo group, or
    (4) a 9- to 14-membered fused polycyclic non-aromatic heterocycle optionally further substituted by 1 to 3 substituents selected from a $C_{1-6}$ alkyl group and an oxo group; and
  $R^3$ and $R^4$ are each independently a hydrogen atom, a halogen atom or a $C_{1-6}$ alkyl group, or a salt thereof.

[4] The compound described in the above-mentioned [3], wherein
  $R^1$ is

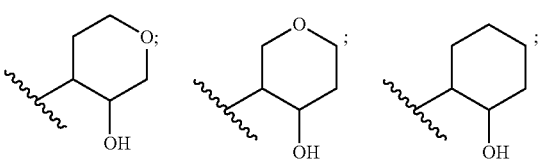

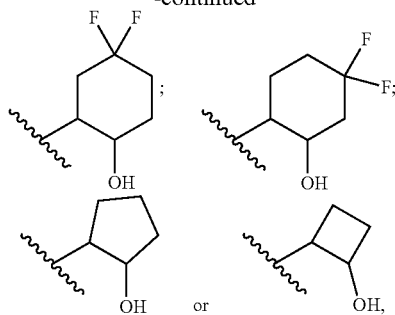

or a salt thereof.

[5] The compound described in the above-mentioned [3], wherein ring A is
  (1) a benzene ring further substituted by 1 to 3 substituents selected from (a) a halogen atom, (b) a mono- or di-$C_{1-6}$ alkyl-carbamoyl group optionally substituted by 1 or 2 substituents selected from (i) a $C_{1-6}$ alkoxy group and (ii) a 3- to 14-membered non-aromatic heterocyclic group, and (c) a 5- to 14-membered aromatic heterocyclic group optionally substituted by 1 to 3 $C_{1-6}$ alkyl groups, or
  (2) a 5- or 6-membered monocyclic aromatic heterocycle further substituted by one 5- to 14-membered aromatic heterocyclic group optionally substituted by 1 to 3 $C_{1-6}$ alkyl groups, or a salt thereof.

[6] The compound described in the above-mentioned [3], wherein ring A is

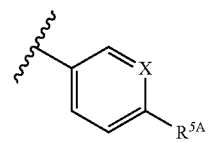

wherein $R^{5A}$ is a mono- or di-$C_{1-6}$ alkyl-carbamoyl group optionally substituted by 1 or 2 substituents selected from a $C_{1-6}$ alkoxy group and a 3- to 14-membered non-aromatic heterocyclic group;

X is $CR^{6A}$ or N; and $R^{6A}$ is a hydrogen atom or a halogen atom, or a salt thereof.

[7] The compound described in the above-mentioned [3], wherein ring A is

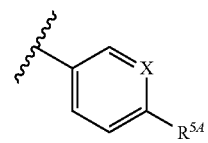

wherein $R^{5A}$ is a 5- to 14-membered aromatic heterocyclic group optionally substituted by 1 to 3 $C_{1-6}$ alkyl groups;

X is $CR^{6A}$ or N; and $R^{6A}$ is a hydrogen atom or a halogen atom, or a salt thereof.

[8] The compound described in the above-mentioned [1], wherein $R^1$ is a 3- to 14-membered non-aromatic heterocyclic group substituted by one hydroxy group;

$R^2$ is a hydrogen atom;

ring A is
(1) a benzene ring further substituted by 1 to 3 substituents selected from (a) a halogen atom, (b) a mono- or di-$C_{1-6}$ alkyl-carbamoyl group optionally substituted by 1 or 2 substituents selected from (i) a $C_{1-6}$ alkoxy group and (ii) a 3- to 14-membered non-aromatic heterocyclic group, and (c) a 5- to 14-membered aromatic heterocyclic group optionally substituted by 1 to 3 $C_{1-6}$ alkyl groups, or
(2) a 5- or 6-membered monocyclic aromatic heterocycle further substituted by one 5- to 14-membered aromatic heterocyclic group optionally substituted by 1 to 3 $C_{1-6}$ alkyl groups; and $R^3$ and $R^4$ are each independently a hydrogen atom or a halogen atom, or a salt thereof.

[9] N-((3R,4S)-3-Hydroxytetrahydro-2H-pyran-4-yl)-7-(4-(1-methyl-1H-1,2,3-triazol-4-yl)benzyl)furo[3,2-b]pyridine-5-carboxamide, or a salt thereof.

[10] N-((3R,4S)-3-Hydroxytetrahydro-2H-pyran-4-yl)-7-(4-(1-methyl-1H-1,2,3-triazol-4-yl)benzyl)-2,3-dihydrofuro[3,2-b]pyridine-5-carboxamide, or a salt thereof.

[11] 7-(3-Fluoro-4-((2-methoxyethyl)carbamoyl)benzyl)-N-((3R,4S)-3-hydroxytetrahydro-2H-pyran-4-yl)-2,3-dihydrofuro[3,2-b]pyridine-5-carboxamide, or a salt thereof.

[12] 7-(3-Fluoro-4-((((S)-tetrahydrofuran-2-yl)methyl)carbamoyl)benzyl)-N-((3R,4S)-3-hydroxytetrahydro-2H-pyran-4-yl)-2,3-dihydrofuro[3,2-b]pyridine-5-carboxamide, or a salt thereof.

[13] 7-(3-Fluoro-4-((((S)-tetrahydrofuran-2-yl)methyl)carbamoyl)benzyl)-N-((3R,4S)-3-hydroxytetrahydro-2H-pyran-4-yl)furo[3,2-b]pyridine-5-carboxamide, or a salt thereof.

[14] A medicament comprising the compound described in the above-mentioned [1] or a salt thereof.

[15] The medicament described in the above-mentioned [14], which is a cholinergic muscarinic M1 receptor positive allosteric modulator.

[16] The medicament described in the above-mentioned [14], which is a prophylactic or therapeutic agent for constipation.

[17] A method of cholinergic muscarinic M1 receptor positive allosteric modulation in a mammal, comprising administering an effective amount of the compound described in the above-mentioned [1] or a salt thereof to said mammal.

[18] A method for the prophylaxis or treatment of constipation in a mammal, comprising administering an effective amount of the compound described in the above-mentioned [1] or a salt thereof to the mammal.

[19] Use of the compound described in the above-mentioned [1] or a salt thereof in the production of a prophylactic or therapeutic agent for constipation.

[20] The compound described in the above-mentioned [1] or a salt thereof for use in the prophylaxis or treatment of constipation.

Effect of the Invention

The compound of the present invention may have a cholinergic muscarinic M1 receptor positive allosteric modulator activity, and may be useful as a medicament such as a prophylactic or therapeutic drug for, for example, constipation, such as constipation associated with neurological disease (e.g., Parkinson's disease, spinal cord injury, multiple sclerosis), idiopathic constipation, age-related constipation, opioid-induced constipation and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl. In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-4}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-4}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,

(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbocycle" include a $C_{6-14}$ aromatic hydrocarbocycle, $C_{3-10}$ cycloalkane and $C_{3-10}$ cycloalkene.

In the present specification, examples of the "$C_{6-14}$ aromatic hydrocarbocycle" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocyclic group" include an aromatic heterocyclic group and a non-aromatic heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycycle (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocyclic groups such as aziridine, oxirane, thiirane, azetidine, oxetane, thietane, tetrahydrothiophene, tetrahydrofuran, Pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzoimidazole, dihydrobenzooxazole, dihydrobenzothiazole, dihydrobenzoisothiazole, dihydronaphto[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include the "heterocycle" containing at least one nitrogen atom as a ring-constituting atom.

Each symbol in the formula (I) is explained below.

$R^1$ is an optionally substituted cyclic group.

As the "optionally substituted cyclic group" for $R^1$, an optionally substituted heterocyclic group, and an optionally substituted non-aromatic hydrocarbon ring group can be mentioned.

As the "heterocyclic group" of the "optionally substituted heterocyclic group" for $R^1$, a 3- to 14-membered non-aromatic heterocyclic group (e.g., tetrahydropyranyl) is preferable. As the substituent, 1 to 3 (preferably 1) hydroxy groups are preferable.

As the "non-aromatic hydrocarbon ring group" of the "optionally substituted non-aromatic hydrocarbon ring group" for $R^1$, a $C_{3-10}$ cycloalkyl group (e.g., cyclobutyl, cyclopentyl, cyclohexyl) is preferable. As the substituent, 1 to 3 (preferably 1) substituents selected from a hydroxy group and a halogen atom (e.g., fluorine atom) are preferable.

$R^1$ is preferably
(1) an optionally substituted 3- to 14-membered non-aromatic heterocyclic group, or
(2) an optionally substituted $C_{3-10}$ cycloalkyl group.

$R^1$ is more preferably
(1) a 3- to 14-membered non-aromatic heterocyclic group (e.g., tetrahydropyranyl) optionally substituted by 1 to 3 (preferably 1) hydroxy groups, or
(2) a $C_{3-10}$ cycloalkyl group (e.g., cyclobutyl, cyclopentyl, cyclohexyl) optionally substituted by 1 to 3 (preferably 1) substituents selected from a hydroxy group and a halogen atom (e.g., fluorine atom).

$R^1$ is further preferably
(1) a 3- to 14-membered non-aromatic heterocyclic group (e.g., tetrahydropyranyl) substituted by one hydroxy group, or
(2) a $C_{3-10}$ cycloalkyl group (e.g., cyclohexyl) substituted by 1 to 3 (preferably 1) substituents selected from a hydroxy group and a halogen atom (e.g., fluorine atom).

$R^1$ is furthermore preferably a 3- to 14-membered non-aromatic heterocyclic group (e.g., tetrahydropyranyl) substituted by one hydroxy group.

In another embodiment of the present invention, $R^1$ is preferably

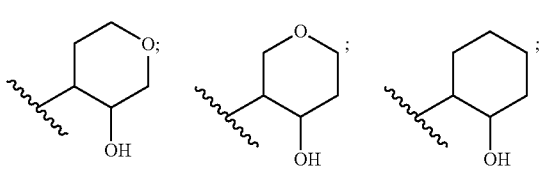

-continued
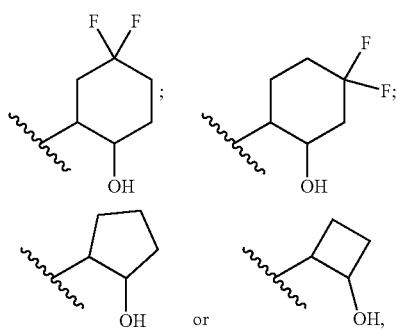
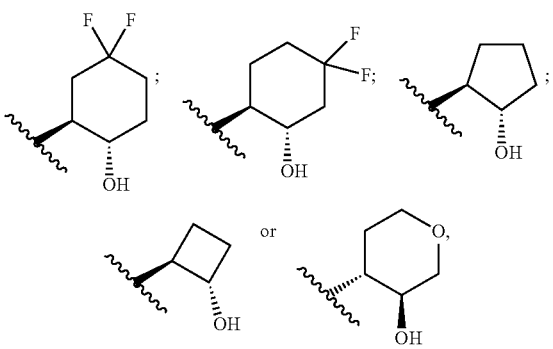
more preferably,
more preferably,
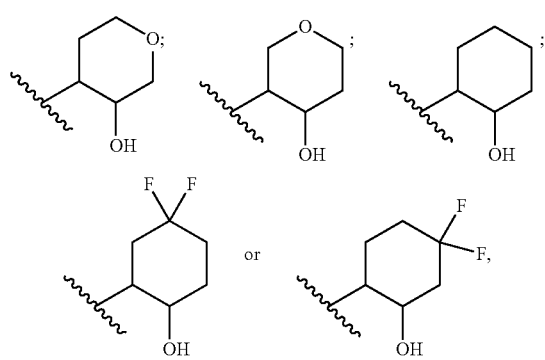
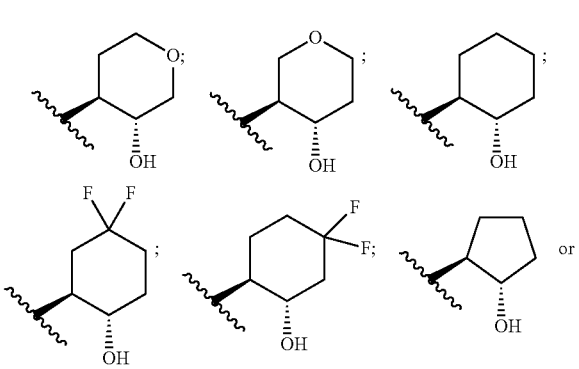
further preferably,
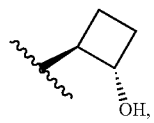
further preferably,
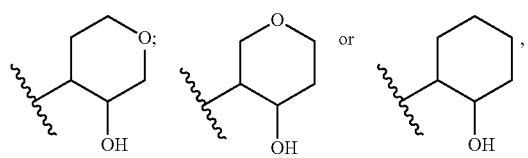 [SMILES: *C1CCOCC1O ; *C1COCCC1O ; *C1CCCCC1O]
particularly preferably,
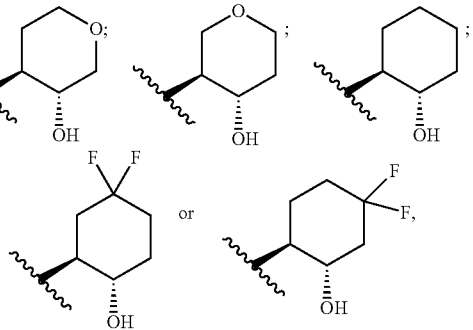
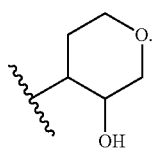 [SMILES: *C1CCOCC1O]
In another embodiment of the present invention, $R^1$ is preferably
furthermore preferably,
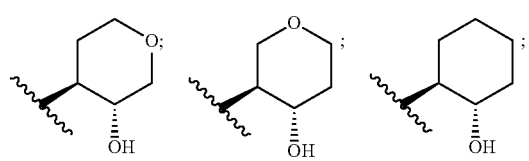
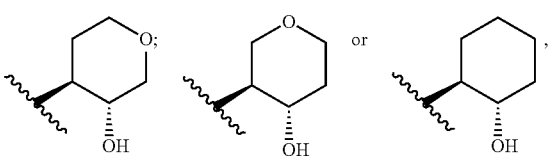 [SMILES: *[C@H]1CCOC[C@@H]1O ; *[C@H]1COCC[C@@H]1O ; *[C@H]1CCCC[C@@H]1O]

particularly preferably,

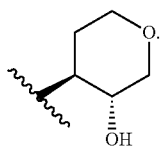 [SMILES: *[C@H]1CCOC[C@@H]1O]

$R^2$ is a hydrogen atom, a halogen atom, a cyano group, an optionally substituted $C_{1-6}$ alkyl group, or an optionally substituted $C_{1-6}$ alkoxy group.

$R^2$ is preferably a hydrogen atom, a halogen atom (e.g., chlorine atom, fluorine atom), a $C_{1-6}$ alkyl group (e.g., methyl), or a $C_{1-6}$ alkoxy group (e.g., methoxy), more preferably, a hydrogen atom or a $C_{1-6}$ alkyl group (e.g., methyl), further preferably, a hydrogen atom.

=== is a single bond or a double bond.

In one embodiment of the present invention,

=== is a single bond.

In another embodiment of the present invention,

=== is a double bond.

Ring A is an optionally further substituted ring.

As the "optionally further substituted ring" for ring A, an optionally further substituted 4- to 6-membered monocyclic hydrocarbon ring, an optionally further substituted 5- or 6-membered monocyclic aromatic heterocycle, an optionally further substituted 4- to 6-membered monocyclic non-aromatic heterocycle, and an optionally further substituted 9- to 14-membered fused polycyclic (preferably bicyclic or tricyclic) non-aromatic heterocycle can be mentioned.

As the "4- to 6-membered monocyclic hydrocarbon ring" of the "optionally further substituted 4- to 6-membered monocyclic hydrocarbon ring" for ring A, a benzene ring, a $C_{4-6}$ cycloalkane ring (e.g., cyclobutane ring, cyclopentane ring, cyclohexane ring), and a $C_{4-6}$ cycloalkene ring (e.g., cyclobutene ring, cyclopentene ring, cyclohexene ring) can be mentioned. As the "4- to 6-membered monocyclic hydrocarbon ring", a benzene ring can be preferably mentioned.

As the substituent of the "optionally further substituted 4- to 6-membered monocyclic hydrocarbon ring" for ring A, 1 to 3 substituents selected from (1) a cyano group, (2) a halogen atom, (3) a carboxy group, (4) an optionally substituted hydroxy group, (5) an optionally substituted carbamoyl group, (6) an optionally substituted amino group, (7) an optionally substituted heterocyclic group and (8) an optionally substituted hydrocarbon group can be mentioned.

As the "5- or 6-membered monocyclic aromatic heterocycle" of the "optionally further substituted 5- or 6-membered monocyclic aromatic heterocycle" for ring A, a 5- or 6-membered monocyclic aromatic heterocycle containing, as a ring-constituting atom besides carbon atom, 1 to 4 hetero atoms selected from a nitrogen atom, a sulfur atom and an oxygen atom (e.g., thiophene ring, furan ring, pyrrole ring, imidazole ring, pyrazole ring, thiazole ring, isothiazole ring, oxazole ring, isoxazole ring, pyridine ring, pyrazine ring, pyrimidine ring, pyridazine ring, 1,2,4-oxadiazole ring, 1,3,4-oxadiazole ring, 1,2,4-thiadiazole ring, 1,3,4-thiadiazole ring, triazole ring, tetrazole ring, triazine ring) can be mentioned. As the "5- or 6-membered monocyclic aromatic heterocycle", pyridine ring can be preferably mentioned.

As the substituent of the "optionally further substituted 5- or 6-membered monocyclic aromatic heterocycle" for ring A, 1 to 3 substituents selected from (1) a cyano group, (2) a halogen atom, (3) a carboxy group, (4) an optionally substituted hydroxy group, (5) an optionally substituted carbamoyl group, (6) an optionally substituted amino group, (7) an optionally substituted heterocyclic group and (8) an optionally substituted hydrocarbon group can be mentioned.

As the "4- to 6-membered monocyclic non-aromatic heterocycle" of the "optionally further substituted 4- to 6-membered monocyclic non-aromatic heterocycle" for ring A, a 4- to 6-membered monocyclic non-aromatic heterocycle containing, as a ring-constituting atom besides carbon atom, 1 to 4 hetero atoms selected from a nitrogen atom, a sulfur atom and an oxygen atom (e.g., azetidine ring, oxetane ring, thietane ring, tetrahydrothiophene ring, tetrahydrofuran ring, pyrroline ring, pyrrolidine ring, imidazoline ring, imidazolidine ring, oxazoline ring, oxazolidine ring, pyrazoline ring, pyrazolidine ring, thiazoline ring, thiazolidine ring, tetrahydroisothiazole ring, tetrahydroisoxazole ring, piperidine ring, piperazine ring, tetrahydropyridine ring, dihydropyridine ring, dihydrothiopyran ring, tetrahydropyrimidine ring, tetrahydropyridazine ring, dihydropyran ring, tetrahydropyran ring, tetrahydrothiopyran ring, morpholine ring, thiomorpholine ring) can be mentioned. As the "4- to 6-membered monocyclic non-aromatic heterocycle", dihydropyridine ring can be preferably mentioned.

As the substituent of the "optionally further substituted 4- to 6-membered monocyclic non-aromatic heterocycle" for ring A, 1 to 3 substituents selected from (1) a cyano group, (2) a halogen atom, (3) a carboxy group, (4) an optionally substituted hydroxy group, (5) an optionally substituted carbamoyl group, (6) an optionally substituted amino group, (7) an optionally substituted heterocyclic group, (8) optionally substituted hydrocarbon group and (9) an oxo group can be mentioned.

As the "9- to 14-membered fused polycyclic (preferably bicyclic or tricyclic) non-aromatic heterocycle" of the "optionally further substituted 9- to 14-membered fused polycyclic (preferably bicyclic or tricyclic) non-aromatic heterocycle" for ring A, a 9- to 14-membered fused polycyclic (preferably bicyclic or tricyclic) non-aromatic heterocycle containing, as a ring-constituting atom besides carbon atom, 1 to 4 hetero atoms selected from a nitrogen atom, a sulfur atom and an oxygen atom (e.g., dihydrobenzofuran ring, dihydrobenzimidazole ring, dihydrobenzoxazole ring, dihydrobenzothiazole ring, dihydrobenzisothiazole ring, dihydronaphtho[2,3-b]thiophene ring, tetrahydroisoquinoline ring, tetrahydroquinoline ring, 4H-quinolizine ring, indoline ring, isoindoline ring, tetrahydrothieno[2,3-c]pyridine ring, tetrahydrobenzazepine ring, tetrahydroquinoxaline ring, tetrahydrophenanthridine ring, hexahydrophenothiazine ring, hexahydrophenoxazine ring, tetrahydrophthalazine ring, tetrahydronaphthyridine ring, tetrahydroquinazoline ring, tetrahydrocinnoline ring, tetrahydrocarbazole ring, tetrahydro-β-carboline ring, tetrahydroacridine ring, tetrahydrophenazine ring, tetrahydrothioxanthene ring, octahydroisoquinoline ring) can be mentioned. As the "9- to 14-membered fused polycyclic (preferably bicyclic or tricyclic) non-aromatic heterocycle", isoindoline ring can be preferably mentioned.

As the substituent of the "optionally further substituted 9- to 14-membered fused polycyclic (preferably bicyclic or tricyclic) non-aromatic heterocycle" for ring A, 1 to 3 substituents selected from (1) a cyano group, (2) a halogen atom, (3) a carboxy group, (4) an optionally substituted hydroxy group, (5) an optionally substituted carbamoyl group, (6) an optionally substituted amino group, (7) an optionally substituted heterocyclic group, (8) an optionally substituted hydrocarbon group and (9) an oxo group can be mentioned.

As the "optionally substituted hydroxy group" which is a substituent of the "optionally further substituted 4- to 6-membered monocyclic hydrocarbon ring", the "optionally further substituted 5- or 6-membered monocyclic aromatic heterocycle", the "optionally further substituted 4- to 6-membered monocyclic non-aromatic heterocycle" or the "optionally further substituted 9- to 14-membered fused polycyclic (preferably bicyclic or tricyclic) non-aromatic heterocycle" for ring A, a $C_{1-6}$ alkoxy group is preferable.

As the "optionally substituted carbamoyl group" which is a substituent of the "optionally further substituted 4- to 6-membered monocyclic hydrocarbon ring", the "optionally further substituted 5- or 6-membered monocyclic aromatic heterocycle", the "optionally further substituted 4- to 6-membered monocyclic non-aromatic heterocycle" or the "optionally further substituted 9- to 14-membered fused polycyclic (preferably bicyclic or tricyclic) non-aromatic heterocycle" for ring A, a mono- or di-$C_{1-6}$ alkyl-carbamoyl group, a mono- or di-$C_{3-10}$ cycloalkyl-carbamoyl group, or a $C_{6-14}$ aryl-carbamoyl group, each of which is optionally substituted is preferable.

As the "optionally substituted heterocyclic group" which is a substituent of the "optionally further substituted 4- to 6-membered monocyclic hydrocarbon ring", the "optionally further substituted 5- or 6-membered monocyclic aromatic heterocycle", the "optionally further substituted 4- to 6-membered monocyclic non-aromatic heterocycle" or the "optionally further substituted 9- to 14-membered fused polycyclic (preferably bicyclic or tricyclic) non-aromatic heterocycle" for ring A, a 5- to 14-membered aromatic heterocyclic group (e.g., pyrazolyl, thiazolyl, triazolyl, imidazolyl, pyridazinyl, pyrimidinyl) optionally substituted by 1 to 3 $C_{1-6}$ alkyl groups is preferable.

Ring A is preferably
(1) an optionally further substituted benzene ring,
(2) an optionally further substituted 5- or 6-membered monocyclic aromatic heterocycle,
(3) an optionally further substituted 4- to 6-membered monocyclic non-aromatic heterocycle, or
(4) an optionally further substituted 9- to 14-membered fused polycyclic non-aromatic heterocycle.

Ring A is more preferably
(1) a benzene ring optionally further substituted by 1 to 3 (preferably 1 or 2, more preferably 1) substituents selected from
  (a) a halogen atom (e.g., fluorine atom),
  (b) a $C_{1-6}$ alkoxy group (e.g., methoxy),
  (c) a mono- or di-$C_{1-6}$ alkyl-carbamoyl group (e.g., methylcarbamoyl, ethylcarbamoyl, propylcarbamoyl, isopropylcarbamoyl, butylcarbamoyl, isobutylcarbamoyl, pentylcarbamoyl) optionally substituted by 1 or 2 (preferably 1) substituents selected from
    (i) a $C_{1-6}$ alkoxy group (e.g., methoxy, ethoxy, tert-butoxy),
    (ii) a $C_{3-10}$ cycloalkyl group (e.g., cyclopropyl, cyclopentyl),
    (iii) a 3- to 14-membered non-aromatic heterocyclic group (e.g., tetrahydrofuranyl, tetrahydropyranyl),
    (iv) a $C_{6-14}$ aryl group (e.g., phenyl) optionally substituted by 1 to 3 (preferably 1) hydroxy groups,
    (v) a $C_{1-6}$ alkoxy-carbonyl group (e.g., methoxycarbonyl),
    (vi) a carboxy group,
    (vii) a $C_{1-6}$ alkylthio group (e.g., isopropylthio, tert-butylthio),
    (viii) a mono- or di-$C_{1-6}$ alkyl-carbamoyl group (e.g., dimethylcarbamoyl, diethylcarbamoyl), and
    (ix) a 3- to 14-membered non-aromatic heterocyclyl-carbonyl group (e.g., pyrrolidin-1-ylcarbonyl),
  (d) a mono- or di-$C_{3-10}$ cycloalkyl-carbamoyl group (e.g., cyclopropylcarbamoyl),
  (e) a $C_{6-14}$ aryl-carbamoyl group (e.g., phenylcarbamoyl) optionally substituted by 1 to 3 (preferably 1) hydroxy groups, and
  (f) a 5- to 14-membered aromatic heterocyclic group (e.g., pyrazolyl, thiazolyl, triazolyl, imidazolyl, pyridazinyl, pyrimidinyl) optionally substituted by 1 to 3 (preferably 1 or 2, more preferably 1) $C_{1-6}$ alkyl groups (e.g., methyl),
(2) a 5- or 6-membered monocyclic aromatic heterocycle (e.g., pyridine ring) optionally further substituted by 1 to 3 (preferably 1 or 2, more preferably 1) substituents selected from
  (a) a $C_{1-6}$ alkoxy group (e.g., methoxy), and
  (b) a 5- to 14-membered aromatic heterocyclic group (e.g., pyrazolyl, triazolyl) optionally substituted by 1 to 3 (preferably 1 or 2, more preferably 1) $C_{1-6}$ alkyl groups (e.g., methyl),
(3) a 4- to 6-membered monocyclic non-aromatic heterocycle (e.g., dihydropyridine ring) optionally further substituted by one oxo group, or
(4) a 9- to 14-membered fused polycyclic (preferably bicyclic or tricyclic) non-aromatic heterocycle (e.g., isoindoline ring) optionally further substituted by 1 to 3 (preferably 1 or 2) substituents selected from a $C_{1-6}$ alkyl group (e.g., methyl) and an oxo group.

Ring A is further preferably
(1) a benzene ring optionally further substituted by 1 to 3 (preferably 1 or 2, more preferably 1) substituents selected from
  (a) a halogen atom (e.g., fluorine atom),
  (b) a $C_{1-6}$ alkoxy group (e.g., methoxy),
  (c) a mono- or di-$C_{1-6}$ alkyl-carbamoyl group (e.g., methylcarbamoyl, ethylcarbamoyl) optionally substituted by 1 or 2 (preferably 1) substituents selected from
    (i) a $C_{1-6}$ alkoxy group (e.g., methoxy), and
    (ii) a 3- to 14-membered non-aromatic heterocyclic group (e.g., tetrahydrofuranyl), and
  (d) a 5- to 14-membered aromatic heterocyclic group (e.g., pyrazolyl, thiazolyl, triazolyl, imidazolyl, pyridazinyl, pyrimidinyl) optionally substituted by 1 to 3 (preferably 1 or 2, more preferably 1) $C_{1-6}$ alkyl groups (e.g., methyl),
(2) a 5- or 6-membered monocyclic aromatic heterocycle (e.g., pyridine ring) optionally further substituted by 1 to 3 (preferably 1 or 2, more preferably 1) substituents selected from
  (a) a $C_{1-6}$ alkoxy group (e.g., methoxy), and
  (b) a 5- to 14-membered aromatic heterocyclic group (e.g., pyrazolyl, triazolyl) optionally substituted by 1 to 3 (preferably 1 or 2, more preferably 1) $C_{1-6}$ alkyl groups (e.g., methyl), or
(3) a 4- to 6-membered monocyclic non-aromatic heterocycle (e.g., dihydropyridine ring) optionally further substituted by one oxo group.

Ring A is furthermore preferably
(1) a benzene ring further substituted by 1 to 3 (preferably 1 or 2) substituents selected from
  (a) a halogen atom (e.g., fluorine atom),
  (b) a mono- or di-$C_{1-6}$ alkyl-carbamoyl group (e.g., methylcarbamoyl, ethylcarbamoyl) optionally substituted by 1 or 2 (preferably 1) substituents selected from
    (i) a $C_{1-6}$ alkoxy group (e.g., methoxy), and
    (ii) a 3- to 14-membered non-aromatic heterocyclic group (e.g., tetrahydrofuranyl), and
  (c) a 5- to 14-membered aromatic heterocyclic group (e.g., pyrazolyl, thiazolyl, triazolyl, imidazolyl, pyridazinyl, pyrimidinyl, preferably, pyrazolyl, triazolyl, imidazolyl) optionally substituted by 1 to 3 (preferably 1 or 2, more preferably 1) $C_{1-6}$ alkyl groups (e.g., methyl), or
(2) a 5- or 6-membered monocyclic aromatic heterocycle (e.g., pyridine ring) further substituted by one 5- to 14-membered aromatic heterocyclic group (e.g., pyrazolyl, triazolyl) optionally substituted by 1 to 3 (preferably 1 or 2, more preferably 1) $C_{1-6}$ alkyl groups (e.g., methyl).

In the preferable embodiment of the present invention, ring A is

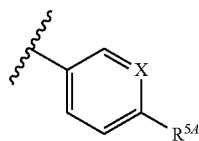

wherein $R^{5A}$ is a mono- or di-$C_{1-6}$ alkyl-carbamoyl group (e.g., methylcarbamoyl, ethylcarbamoyl, propylcarbamoyl, isopropylcarbamoyl, butylcarbamoyl, isobutylcarbamoyl, pentylcarbamoyl) optionally substituted by 1 or 2 (preferably 1) substituents selected from a $C_{1-6}$ alkoxy group (e.g., methoxy, ethoxy, tert-butoxy) and a 3- to 14-membered non-aromatic heterocyclic group (e.g., tetrahydrofuranyl, tetrahydropyranyl);
X is $CR^{6A}$ or N; and
$R^{6A}$ is a hydrogen atom or a halogen atom (e.g., fluorine atom).

In another preferable embodiment of the present invention, ring A is

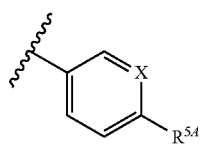

wherein $R^{5A}$ is a 5- to 14-membered aromatic heterocyclic group (e.g., pyrazolyl, thiazolyl, triazolyl, imidazolyl, pyridazinyl, pyrimidinyl) optionally substituted by 1 to 3 (preferably 1 or 2, more preferably 1) $C_{1-6}$ alkyl groups (e.g., methyl);
X is $CR^{6A}$ or N; and
$R^{6A}$ is a hydrogen atom or a halogen atom (e.g., fluorine atom).

$R^3$ and $R^4$ are each independently a hydrogen atom, a halogen atom, a hydroxy group, an optionally substituted $C_{1-6}$ alkyl group, or an optionally substituted $C_{1-6}$ alkoxy group.

Examples of the halogen atom for $R^3$ or $R^4$ include a fluorine atom, a chlorine atom and a bromine atom, and preferably a fluorine atom.

$R^3$ and $R^4$ are preferably each independently a hydrogen atom, a halogen atom, a hydroxy group, a $C_{1-6}$ alkyl group, or a $C_{1-6}$ alkoxy group, more preferably, each independently a hydrogen atom, a halogen atom (e.g., fluorine atom) or a $C_{1-6}$ alkyl group (e.g., methyl), further preferably, each independently a hydrogen atom or a halogen atom (e.g., fluorine atom).

In the preferable embodiment of the present invention, $R^3$ and $R^4$ are both hydrogen atoms, or one of $R^3$ and $R^4$ is a hydrogen atom, and the other is a halogen atom (e.g., fluorine atom), or one of $R^3$ and $R^4$ is a hydrogen atom, and the other is a $C_{1-6}$ alkyl group (e.g., methyl).

In the more preferable embodiment of the present invention, $R^3$ and $R^4$ are both hydrogen atoms.

As preferable embodiments of compound (I), the following compounds can be mentioned.

[Compound I-1]
Compound (I) wherein
$R^1$ is
(1) a 3- to 14-membered non-aromatic heterocyclic group (e.g., tetrahydropyranyl) optionally substituted by 1 to 3 (preferably 1) hydroxy groups, or
(2) a $C_{3-10}$ cycloalkyl group (e.g., cyclobutyl, cyclopentyl, cyclohexyl) optionally substituted by 1 to 3 (preferably 1) substituents selected from a hydroxy group and a halogen atom (e.g., fluorine atom);
$R^2$ is a hydrogen atom or a $C_{1-6}$ alkyl group (e.g., methyl);
ring A is
(1) a benzene ring optionally further substituted by 1 to 3 (preferably 1 or 2, more preferably 1) substituents selected from
  (a) a halogen atom (e.g., fluorine atom),
  (b) a $C_{1-6}$ alkoxy group (e.g., methoxy),
  (c) a mono- or di-$C_{1-6}$ alkyl-carbamoyl group (e.g., methylcarbamoyl, ethylcarbamoyl, propylcarbamoyl, isopropylcarbamoyl, butylcarbamoyl, isobutylcarbamoyl, pentylcarbamoyl) optionally substituted by 1 or 2 (preferably 1) substituents selected from
    (i) a $C_{1-6}$ alkoxy group (e.g., methoxy, ethoxy, tert-butoxy),
    (ii) a $C_{3-10}$ cycloalkyl group (e.g., cyclopropyl, cyclopentyl),
    (iii) a 3- to 14-membered non-aromatic heterocyclic group (e.g., tetrahydrofuranyl, tetrahydropyranyl),
    (iv) a $C_{6-14}$ aryl group (e.g., phenyl) optionally substituted by 1 to 3 (preferably 1) hydroxy groups,
    (v) a $C_{1-6}$ alkoxy-carbonyl group (e.g., methoxycarbonyl),
    (vi) a carboxy group,
    (vii) a $C_{1-6}$ alkylthio group (e.g., isopropylthio, tert-butylthio),
    (viii) a mono- or di-$C_{1-6}$ alkyl-carbamoyl group (e.g., dimethylcarbamoyl, diethylcarbamoyl), and
    (ix) a 3- to 14-membered non-aromatic heterocyclylcarbonyl group (e.g., pyrrolidin-1-ylcarbonyl),
  (d) a mono- or di-$C_{3-10}$ cycloalkyl-carbamoyl group (e.g., cyclopropylcarbamoyl),
  (e) a $C_{6-14}$ aryl-carbamoyl group (e.g., phenylcarbamoyl) optionally substituted by 1 to 3 (preferably 1) hydroxy groups, and
  (f) a 5- to 14-membered aromatic heterocyclic group (e.g., pyrazolyl, thiazolyl, triazolyl, imidazolyl, pyridazinyl, pyrimidinyl) optionally substituted by 1 to 3 (preferably 1 or 2, more preferably 1) $C_{1-6}$ alkyl groups (e.g., methyl), (2) a 5- or 6-membered monocyclic aromatic heterocycle (e.g., pyridine ring) optionally further substituted by 1 to 3 (preferably 1 or 2, more preferably 1) substituents selected from
(a) a $C_{1-6}$ alkoxy group (e.g., methoxy), and
(b) a 5- to 14-membered aromatic heterocyclic group (e.g., pyrazolyl, triazolyl) optionally substituted by 1 to 3 (preferably 1 or 2, more preferably 1) $C_{1-6}$ alkyl groups (e.g., methyl),
(3) a 4- to 6-membered monocyclic non-aromatic heterocycle (e.g., dihydropyridine ring) optionally further substituted by one oxo group, or
(4) a 9- to 14-membered fused polycyclic (preferably bicyclic or tricyclic) non-aromatic heterocycle (e.g., isoindoline ring) optionally further substituted by 1 to 3 (preferably 1 or 2) substituents selected from a $C_{1-6}$ alkyl group (e.g., methyl) and an oxo group; and
$R^3$ and $R^4$ are each independently a hydrogen atom, a halogen atom (e.g., fluorine atom) or $C_{1-6}$ alkyl group (e.g., methyl).

[Compound I-2]
Compound (I) wherein
$R^1$ is
(1) a 3- to 14-membered non-aromatic heterocyclic group (e.g., tetrahydropyranyl) optionally substituted by 1 to 3 (preferably 1) hydroxy groups, or
(2) a $C_{3-10}$ cycloalkyl group (e.g., cyclobutyl, cyclopentyl, cyclohexyl) optionally substituted by 1 to 3 (preferably 1) substituents selected from a hydroxy group and a halogen atom (e.g., fluorine atom);
$R^2$ is a hydrogen atom;
ring A is
(1) a benzene ring optionally further substituted by 1 to 3 (preferably 1 or 2, more preferably 1) substituents selected from
(a) a halogen atom (e.g., fluorine atom),
(b) a $C_{1-6}$ alkoxy group (e.g., methoxy),
(c) a mono- or di-$C_{1-6}$ alkyl-carbamoyl group (e.g., methylcarbamoyl), and
(d) a 5- to 14-membered aromatic heterocyclic group (e.g., pyrazolyl, thiazolyl, triazolyl, pyridazinyl, pyrimidinyl) optionally substituted by 1 to 3 (preferably 1 or 2, more preferably 1) $C_{1-6}$ alkyl groups (e.g., methyl),
(2) a 5- or 6-membered monocyclic aromatic heterocycle (e.g., pyridine ring) optionally further substituted by 1 to 3 (preferably 1 or 2, more preferably 1) substituents selected from
(a) a $C_{1-6}$ alkoxy group (e.g., methoxy), and
(b) a 5- to 14-membered aromatic heterocyclic group (e.g., pyrazolyl, triazolyl) optionally substituted by 1 to 3 (preferably 1 or 2, more preferably 1) $C_{1-6}$ alkyl groups (e.g., methyl), or
(3) a 4- to 6-membered monocyclic non-aromatic heterocycle (e.g., dihydropyridine ring) optionally further substituted by one oxo group; and
$R^3$ and $R^4$ are each independently a hydrogen atom or a halogen atom (e.g., fluorine atom).

[Compound I-3]
Compound (I) wherein
$R^1$ is
(1) 3- to 14-membered non-aromatic heterocyclic group (e.g., tetrahydropyranyl) substituted by one hydroxy group, or
(2) a $C_{3-10}$ cycloalkyl group (e.g., cyclohexyl) substituted by 1 to 3 (preferably 1) substituents selected from a hydroxy group and a halogen atom (e.g., fluorine atom);

$R^2$ is a hydrogen atom;
ring A is
(1) a benzene ring further substituted by 1 to 3 (preferably 1 or 2) substituents selected from
(a) a halogen atom (e.g., fluorine atom),
(b) a mono- or di-$C_{1-6}$ alkyl-carbamoyl group (e.g., methylcarbamoyl, ethylcarbamoyl) optionally substituted by 1 or 2 (preferably 1) substituents selected from
(i) a $C_{1-6}$ alkoxy group (e.g., methoxy), and
(ii) a 3- to 14-membered non-aromatic heterocyclic group (e.g., tetrahydrofuranyl), and
(c) a 5- to 14-membered aromatic heterocyclic group (e.g., pyrazolyl, thiazolyl, triazolyl, imidazolyl, pyridazinyl, pyrimidinyl) optionally substituted by 1 to 3 (preferably 1 or 2, more preferably 1) $C_{1-6}$ alkyl groups (e.g., methyl), or
(2) a 5- or 6-membered monocyclic aromatic heterocycle (e.g., pyridine ring) further substituted by one 5- to 14-membered aromatic heterocyclic group (e.g., pyrazolyl, triazolyl) optionally substituted by 1 to 3 (preferably 1 or 2, more preferably 1) $C_{1-6}$ alkyl groups (e.g., methyl); and
$R^3$ and $R^4$ are each independently a hydrogen atom or a halogen atom (e.g., fluorine atom).

[Compound I-4]
Compound (I) wherein
$R^1$ is a 3- to 14-membered non-aromatic heterocyclic group (e.g., tetrahydropyranyl) substituted by one hydroxy group;
$R^2$ is a hydrogen atom;
ring A is
(1) a benzene ring further substituted by 1 to 3 (preferably 1 or 2) substituents selected from
(a) a halogen atom (e.g., fluorine atom),
(b) a mono- or di-$C_{1-6}$ alkyl-carbamoyl group (e.g., methylcarbamoyl, ethylcarbamoyl) optionally substituted by 1 or 2 (preferably 1) substituents selected from
(i) a $C_{1-6}$ alkoxy group (e.g., methoxy), and
(ii) a 3- to 14-membered non-aromatic heterocyclic group (e.g., tetrahydrofuranyl), and
(c) a 5- to 14-membered aromatic heterocyclic group (e.g., pyrazolyl, triazolyl, imidazolyl) optionally substituted by 1 to 3 (preferably 1 or 2, more preferably 1) $C_{1-6}$ alkyl groups (e.g., methyl), or
(2) a 5- or 6-membered monocyclic aromatic heterocycle (e.g., a pyridine ring) further substituted by one 5- to 14-membered aromatic heterocyclic group (e.g., pyrazolyl, triazolyl) optionally substituted by 1 to 3 (preferably 1 or 2, more preferably 1) $C_{1-6}$ alkyl groups (e.g., methyl); and
$R^3$ and $R^4$ are each independently a hydrogen atom or a halogen atom (e.g., fluorine atom).

[Compound I-5]
Compound (I) wherein
$R^1$ is a 3- to 14-membered non-aromatic heterocyclic group (e.g., tetrahydropyranyl) substituted by one hydroxy group;
$R^2$ is a hydrogen atom;
ring A is a benzene ring further substituted by 1 to 3 (preferably 1 or 2) substituents selected from
(a) a halogen atom (e.g., fluorine atom),
(b) a mono- or di-$C_{1-6}$ alkyl-carbamoyl group (e.g., methylcarbamoyl) optionally substituted by 1 or 2 (preferably 1) substituents selected from a 3- to 14-membered non-aromatic heterocyclic group (e.g., tetrahydrofuranyl), and
(c) a 5- to 14-membered aromatic heterocyclic group (e.g., triazolyl) optionally substituted by 1 to 3 (preferably 1 or 2, more preferably 1) $C_{1-6}$ alkyl groups (e.g., methyl); and
$R^3$ and $R^4$ are each a hydrogen atom.

[Compound I-6]
Compound (I) wherein
R$^1$ is a 3- to 14-membered non-aromatic heterocyclic group (e.g., tetrahydropyranyl) substituted by one hydroxy group;
R$^2$ is a hydrogen atom;
ring A is

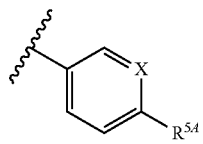

wherein R$^{5A}$ is a mono- or di-C$_{1-6}$ alkyl-carbamoyl group (e.g., methylcarbamoyl, ethylcarbamoyl, propylcarbamoyl, isopropylcarbamoyl, butylcarbamoyl, isobutylcarbamoyl, pentylcarbamoyl) optionally substituted by 1 or 2 (preferably 1) substituents selected from a C$_{1-6}$ alkoxy group (e.g., methoxy, ethoxy, tert-butoxy) and a 3- to 14-membered non-aromatic heterocyclic group (e.g., tetrahydrofuranyl, tetrahydropyranyl);
X is CR$^{6A}$ or N; and
R$^{6A}$ is a hydrogen atom or a halogen atom (e.g., fluorine atom); and
R$^3$ and R$^4$ are each independently a hydrogen atom or a halogen atom (e.g., fluorine atom).

[Compound I-7]
Compound (I) wherein
R$^1$ is a 3- to 14-membered non-aromatic heterocyclic group (e.g., tetrahydropyranyl) substituted by one hydroxy group;
R$^2$ is a hydrogen atom;
ring A is

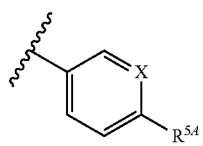

wherein R$^{5A}$ is a 5- to 14-membered aromatic heterocyclic group (e.g., pyrazolyl, thiazolyl, triazolyl, imidazolyl, pyridazinyl, pyrimidinyl) optionally substituted by 1 to 3 (preferably 1 or 2, more preferably 1) C$_{1-6}$ alkyl groups (e.g., methyl);
X is CR$^{6A}$ or N; and
R$^{6A}$ is a hydrogen atom or a halogen atom (e.g., fluorine atom); and
R$^3$ and R$^4$ are each independently a hydrogen atom or a halogen atom (e.g., fluorine atom).

Specific preferable examples of the compound represented by the formula (I) include the compounds of Examples 1-113.

When compound (I) is in the form of a salt, examples of such salt include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, examples of a preferable pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. Compound (I) may be a compound labeled or substituted with an isotope (e.g., $^2$H, $^3$H, $^{11}$C, $^{14}$C, $^{18}$F, $^{35}$S, $^{125}$I). A compound labeled with or substituted by an isotope can be used, for example, as a tracer used for Positron Emission Tomography (PET) (PET tracer), and is useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are also encompassed in compound (I) of the present invention.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature-300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
- alcohols: methanol, ethanol, tert-butyl alcohol, 2-methoxyethanol and the like;
- ethers: diethyl ether, diphenyl ether, tetrahydrofuran, 1,2-dimethoxyethane and the like;
- aromatic hydrocarbons: chlorobenzene, toluene, xylene and the like;
- saturated hydrocarbons: cyclohexane, hexane and the like; amides: N,N-dimethylformamide, N-methylpyrrolidone and the like;
- halogenated hydrocarbons: dichloromethane, carbon tetrachloride and the like;
- nitriles: acetonitrile and the like;
- sulfoxides: dimethyl sulfoxide and the like;
- aromatic organic bases: pyridine and the like;
- acid anhydrides: acetic anhydride and the like;
- organic acids: formic acid, acetic acid, trifluoroacetic acid and the like;
- inorganic acids: hydrochloric acid, sulfuric acid and the like; esters: ethyl acetate and the like;
- ketones: acetone, methyl ethyl ketone and the like; and water.

Two or more kinds of the above-mentioned solvents may be used by mixing at an appropriate ratio.

When a base is used in the reaction of each step, for example, bases shown below or those described in Examples are used.
- inorganic bases: sodium hydroxide, magnesium hydroxide and the like;
- organic bases: sodium carbonate, calcium carbonate, sodium hydrogen carbonate and the like;
- organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
- metal alkoxides: sodium ethoxide, potassium tert-butoxide and the like;
- alkali metal hydrides: sodium hydride and the like; metal amides: sodium amide, lithium diisopropyl amide, lithium hexamethyl disilazide and the like; and organic lithiums: n-butyllithium and the like.

When an acid or an acidic catalyst is used in the reaction of each step, for example, the acids or acidic catalysts shown below or those described in the Examples are used.
- inorganic acids: hydrochloric acid, sulfuric acid, nitric acid, hydrobromic acid, phosphoric acid and the like;
- organic acids: acetic acid, trifluoroacetic acid, citric acid, p-toluenesulfonic acid, 10-camphorsulfonic acid and the like; Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride, a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining an alkyl halide form from alcohol by reacting with triphenylphosphine and carbon tetrachloride or carbon tetrabromide, and the like may be used. Alternatively, a method of synthesizing an alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonic acid esterification reaction is performed in each step, examples of the sulfonylating agent to be used include methanesulfonyl chloride, p-toluenesulfonyl chloride, methanesulfonic anhydride, p-toluenesulfonic anhydride and the like.

When hydrolysis reaction is performed in each step, an acid or a base is used as the reagent. In addition, when acid hydrolysis reaction of tert-butyl ester is performed, formic acid, triethylsilane and the like are sometimes added to reductively trap the by-produced tert-butyl cation.

When a dehydration reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Compound (I) can be produced by the method shown in the following schemes or a method analogous thereto or the method described in Examples.

Compound (IA) can be produced from compound (1) by the following method.

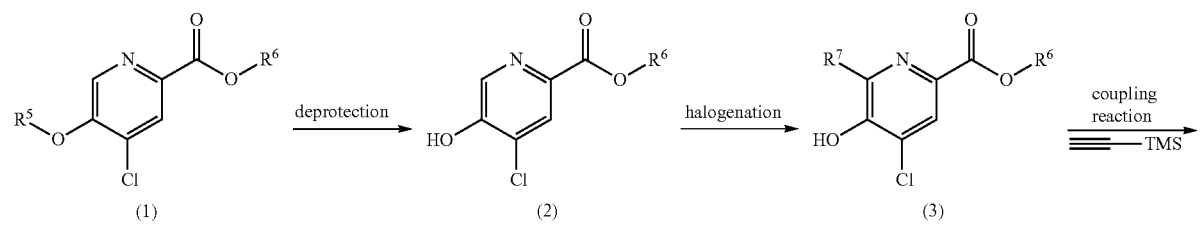

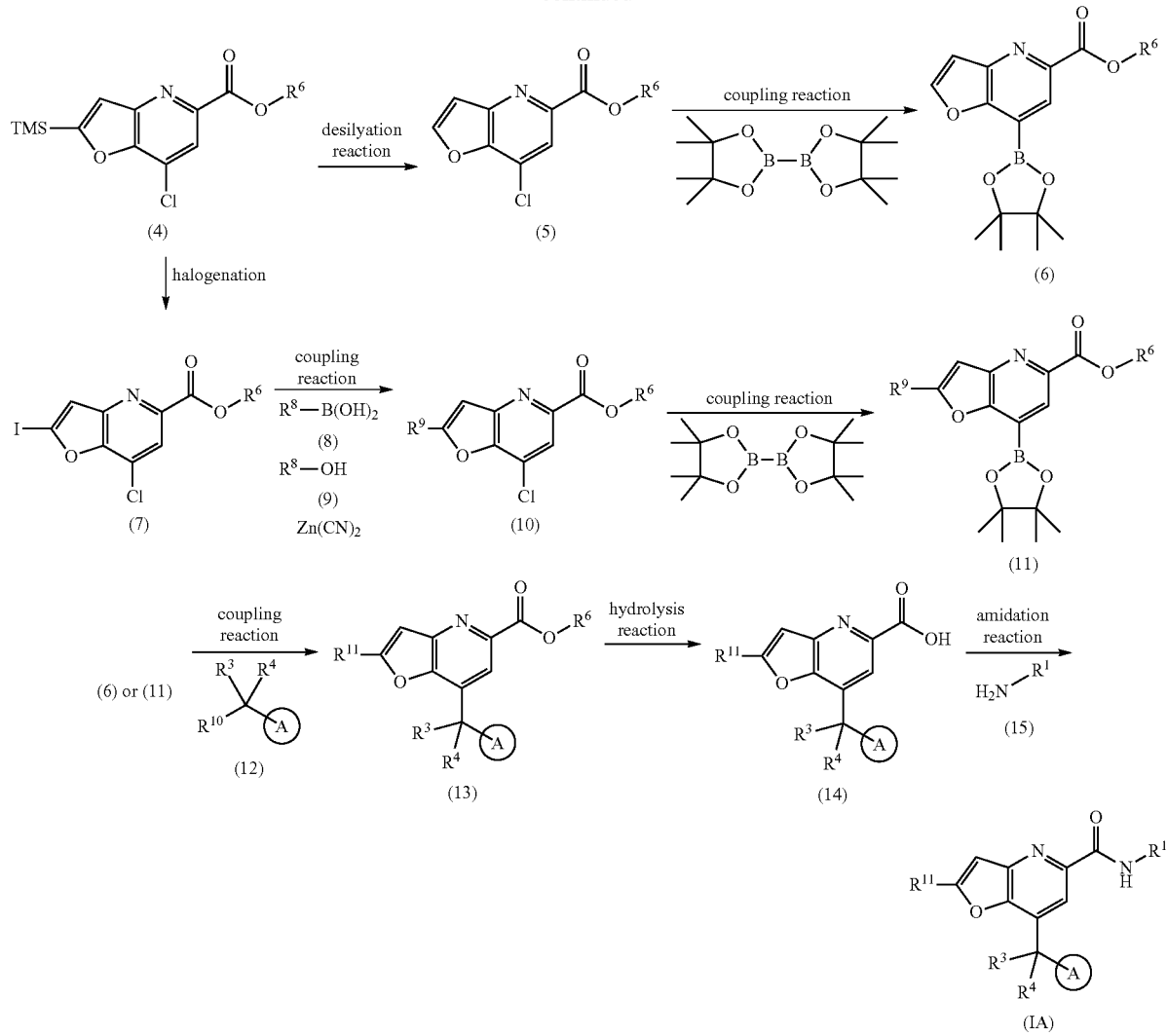

In the reaction formulas, $R^5$ and $R^6$ are each a $C_{1-6}$ alkyl group, $R^7$ and $R^{10}$ are each a halogen atom, $R^8$ is an optionally substituted $C_{1-6}$ alkyl group, $R^9$ is a cyano group, an optionally substituted $C_{1-6}$ alkyl group, or an optionally substituted $C_{1-6}$ alkoxy group, $R^{11}$ is a hydrogen atom, a cyano group, an optionally substituted $C_{1-6}$ alkyl group, or an optionally substituted $C_{1-6}$ alkoxy group, TMS is a trimethylsilyl group, and $R^1$, $R^3$, $R^4$ and ring A mean the same as above.

Compound (2) can be produced by deprotection of $R^5$ which is a protecting group of the hydroxy group of compound (1).

Compound (3) can be produced by halogenation of compound (2) and a halogenating agent such as bromine, iodine and the like.

Compound (4) can be synthesized by Sonogashira coupling reaction of compound (3) and trimethylsilylacetylene in the presence of a metal catalyst and an organic base. As the metal catalyst, a palladium compound such as tetrakis(triphenylphosphine)palladium(0), 1,1'-bis(diphenylphosphino)ferrocene palladium(II) chloride and the like and a copper compound such as copper(I) iodide and the like can be used in combination. As the organic base, triethylamine and diethylamine and the like can be mentioned.

Compound (5) can be produced by a desilylation reaction of compound (4) with fluoride ion such as potassium fluoride, tetran-butylammonium fluoride and the like, or a desilylation reaction of compound (4) under basic conditions such as potassium carbonate and the like or under acidic conditions such as hydrochloric acid and the like.

Compound (6) can be produced by a coupling reaction of compound (5) and bis(pinacolato)diboron in the presence of a metal catalyst.

Compound (7) can be produced by halogenation of compound (4) with N-iodosuccinimide. To the reaction system, a fluoride salt such as potassium fluoride and the like may be added.

Compound (10) can be produced by a coupling reaction of compound (7) and compound (8), compound (9) or zinc cyanide in the presence of a metal catalyst.

Compound (11) can be produced by a coupling reaction of compound (10) and bis(pinacolato)diboron in the presence of a metal catalyst.

Compound (13) can be produced by a coupling reaction of compound (6) or compound (11) and compound (12) in the presence of a metal catalyst.

Compound (14) can be produced by hydrolysis of compound (13).

Compound (IA) can be produced by an amidation reaction of compound (14) and compound (15).

Compound (13) in the above-mentioned scheme can also be produced from compound (16) by the following method.

Compound (22) can be produced by a desilylation reaction of compound (21) with fluoride ion such as potassium fluoride, tetran-butylammonium fluoride and the like, or a desilylation reaction of compound (21) under basic condi-

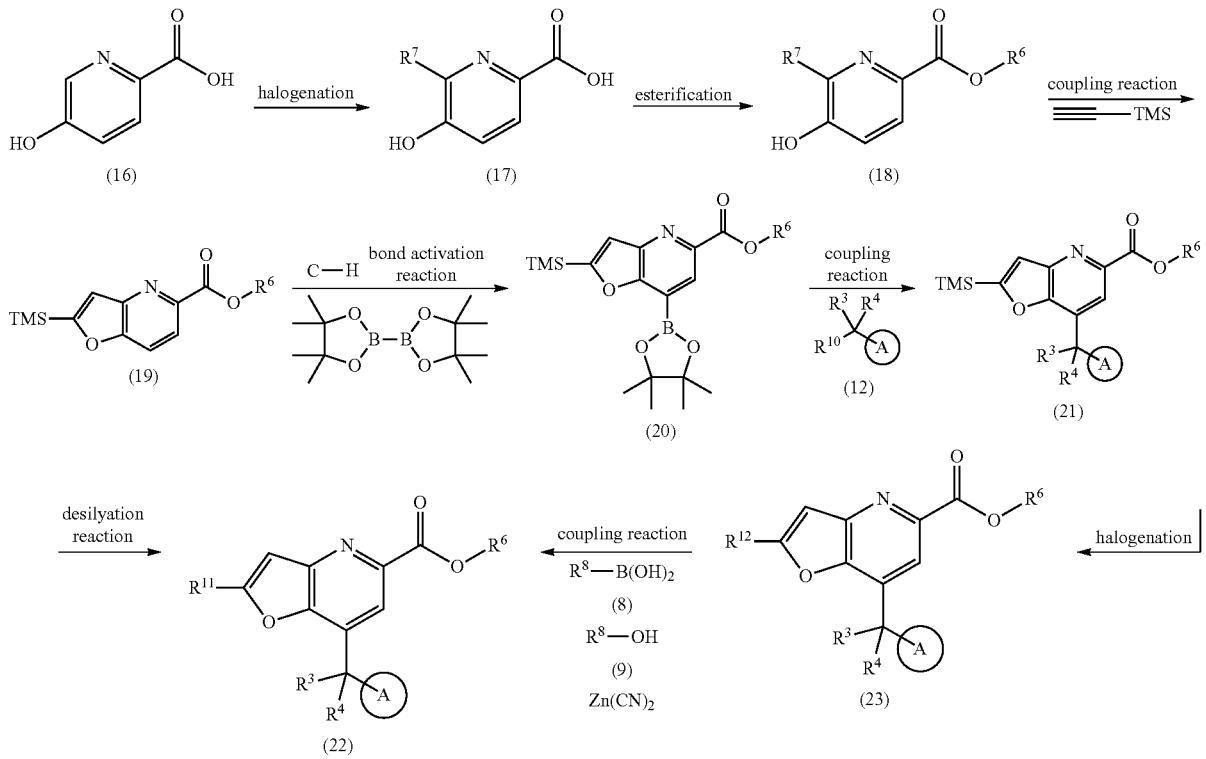

In the reaction formulas, $R^{12}$ is a halogen atom, and $R^3$, $R^4$, $R^6$, $R^7$, $R^{10}$, $R^{11}$ and ring A mean the same as above.

Compound (17) can be produced by halogenation of compound (16) and a halogenating agent such as bromine, iodine and the like.

Compound (18) can be produced by esterification of compound (17).

Compound (19) can be produced by Sonogashira coupling reaction of compound (18) and trimethylsilylacetylene in the presence of a metal catalyst and an organic base. As the metal catalyst, a palladium compound such as tetrakis (triphenylphosphine)palladium(0), 1,1'-bis(diphenylphosphino)ferrocene palladium(II) chloride and the like and a copper compound such as copper(I) iodide and the like can be used in combination. As the organic base, triethylamine, diethylamine and the like can be mentioned.

Compound (20) can be produced by a C—H bond activation reaction of compound (19) in the presence of a metal catalyst. As the metal catalyst, an iridium compound such as bis(1,5-cyclooctadiene)di-μ-methoxydiiridium(I), bis(1,5-cyclooctadiene)diiridium(I) dichloride and the like can be mentioned, which can be used with a ligand such as 2,2'-bipyridine, 4,4'-di-tert-butyl-2,2'-bipyridine and the like for the reaction.

Compound (21) can be produced by a coupling reaction of compound (20) and compound (12) in the presence of a metal catalyst.

Compound (23) can be produced by halogenation of compound (21) with a halogenating agent such as N-iodosuccinimide, NBS, NCS and the like. To the reaction system, a fluoride salt such as potassium fluoride and the like may be added.

tions such as potassium carbonate and the like or under acidic conditions such as hydrochloric acid and the like, or a coupling reaction of compound (23) and compound (8), compound (9) or zinc cyanide in the presence of a metal catalyst.

Compound (IB) can be produced from compound (23) by the following method.

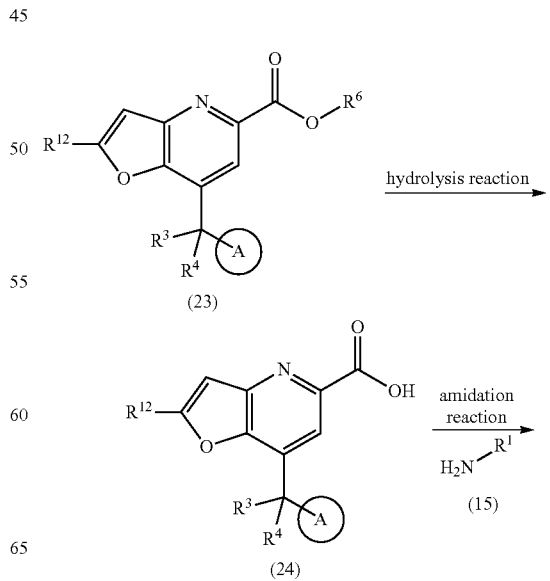

-continued

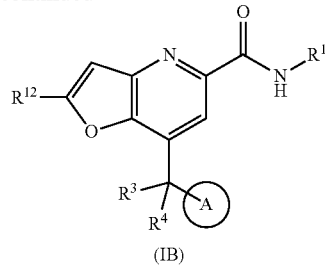

(IB)

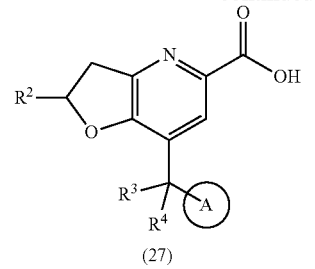

(27)

In the reaction formulas, $R^1$, $R^3$, $R^4$, $R^6$, $R^{12}$ and ring A mean the same as above.

Compound (24) can be produced by hydrolysis of compound (23).

Compound (IB) can be produced by an amidation reaction of compound (24) and compound (15).

Compound (I') can be produced from compound (25) by the following method.

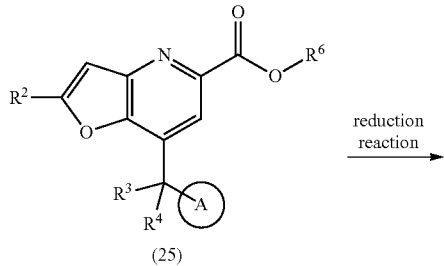

(25)

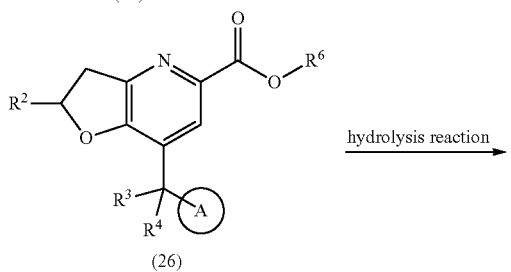

(26)

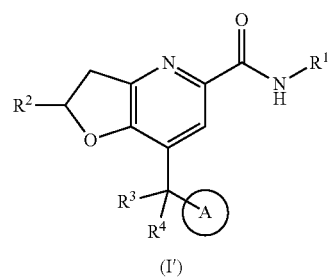

(I')

In the reaction formulas, $R^1$, $R^2$, $R^3$, $R^4$, $R^6$ and ring A mean the same as above.

Compound (26) can be produced by a reduction reaction of compound (25).

Compound (27) can be produced by hydrolysis of compound (26).

Compound (I') can be produced by an amidation reaction of compound (27) and compound (15).

Compound (26) in the above-mentioned scheme can also be produced from compound (28) by the following method.

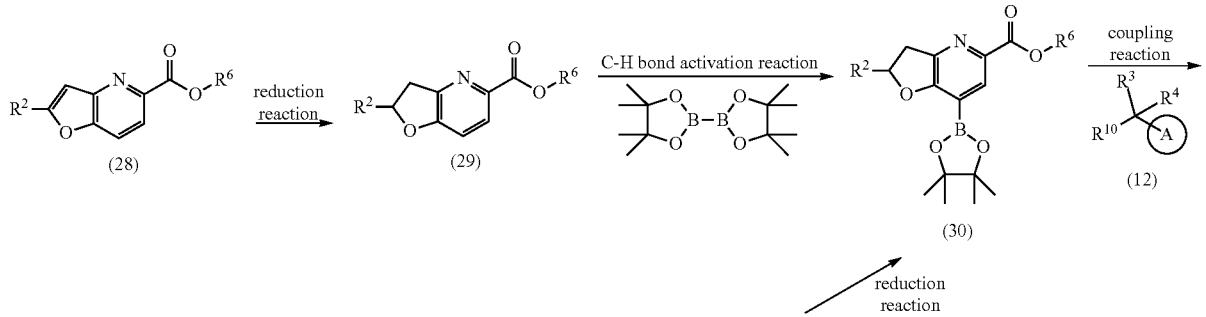

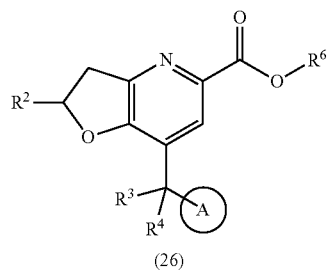 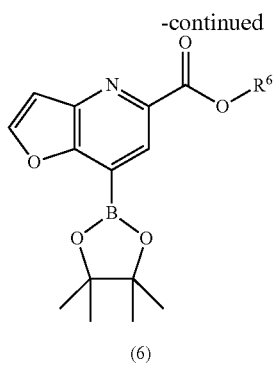 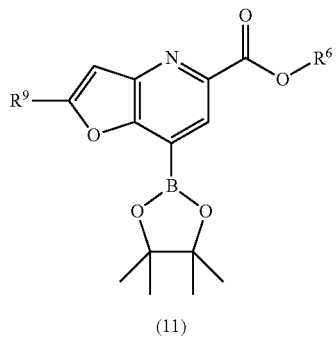

(26)  (6)  (11)

In the reaction formulas, $R^2$, $R^3$, $R^4$, $R^6$, $R^9$, $R^{10}$ and ring A mean the same as above.

Compound (29) can be produced by a reduction reaction of compound (28).

Compound (30) can be produced by a C—H bond activation reaction of compound (29) in the presence of a metal catalyst. As the metal catalyst, an iridium compound such as bis(1,5-cyclooctadiene)di-μ-methoxydiiridium(I), bis(1,5-cyclooctadiene)diiridium(I) dichloride and the like can be mentioned, which can be used with a ligand such as 2,2'-bipyridine, 4,4'-di-tert-butyl-2,2'-bipyridine and the like for the reaction. In addition, compound (30) can also be produced by a reduction reaction of compound (6) or (11).

Compound (26) can be produced by a coupling reaction of compound (30) and compound (12) in the presence of a metal catalyst.

Compound (II) which is compound (IA) wherein one of $R^3$ and $R^4$ is a fluorine atom, and the other is a hydrogen atom can be synthesized from compound (31) which is compound (13) or compound (23) wherein $R^3$ and $R^4$ are each a hydrogen atom by the following method.

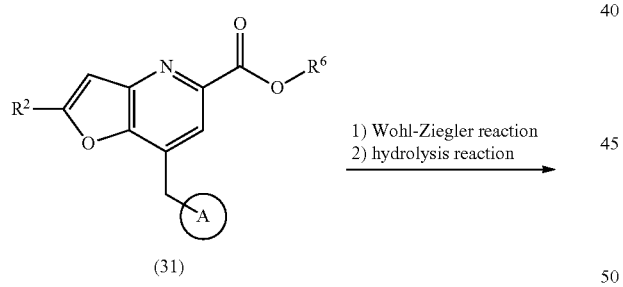

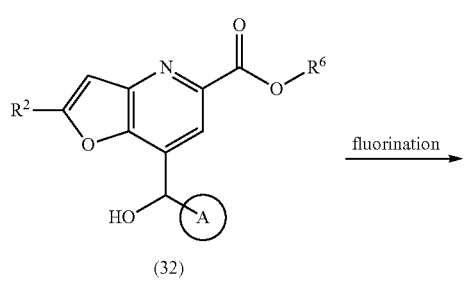

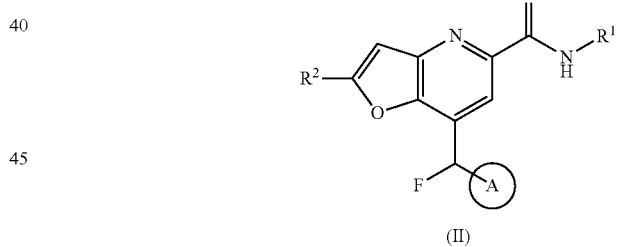

In the reaction formulas, $R^1$, $R^2$, $R^6$ and ring A mean the same as above.

Compound (32) can be produced by Wohl-Ziegler reaction of compound (31) followed by hydrolysis using acetone-water.

Compound (33) can be produced by fluorination of the hydroxy group of compound (32). As the fluorinating agent, (diethylamino)sulfur trifluoride and the like can be mentioned.

Compound (34) can be produced by hydrolysis of compound (33).

Compound (II) can be produced by an amidation reaction of compound (34) and compound (15).

Compounds (III) and (III') can be produced from compound (32) by the following method.

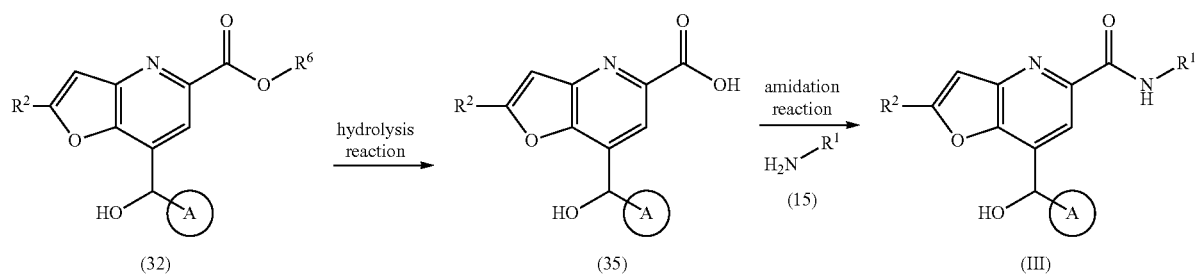

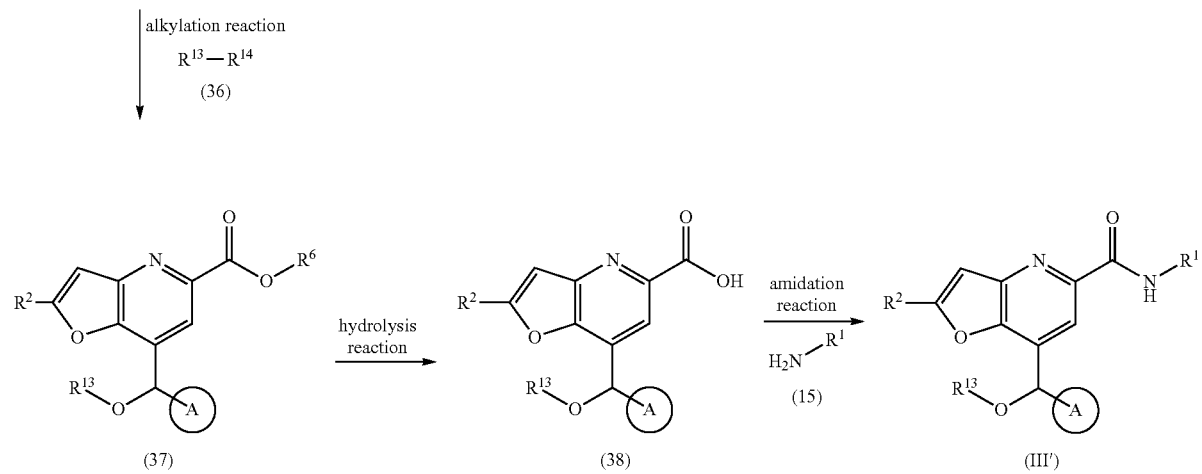

In the reaction formulas, $R^{13}$ is an optionally substituted $C_{1-6}$ alkyl group, $R^{14}$ is a halogen atom, and $R^1$, $R^2$, $R^6$ and ring A mean the same as above.

Compound (35) can be produced by hydrolysis of compound (32).

Compound (III) can be produced by an amidation reaction of compound (35) and compound (15).

Compound (37) can be produced by an alkylation reaction of compound (32) with alkyl halide (36).

Compound (38) can be produced by hydrolysis of compound (37).

Compound (III') can be produced by an amidation reaction of compound (38) and compound (15).

Of compound (I), compound (IV) wherein ring A has an optionally substituted carbamoyl group can be produced from compound (6), compound (11) or compound (30) by the following method.

-continued

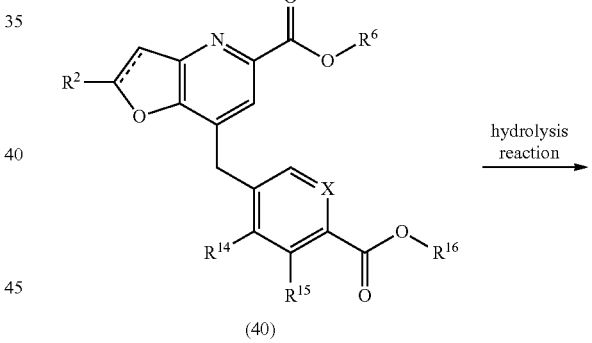

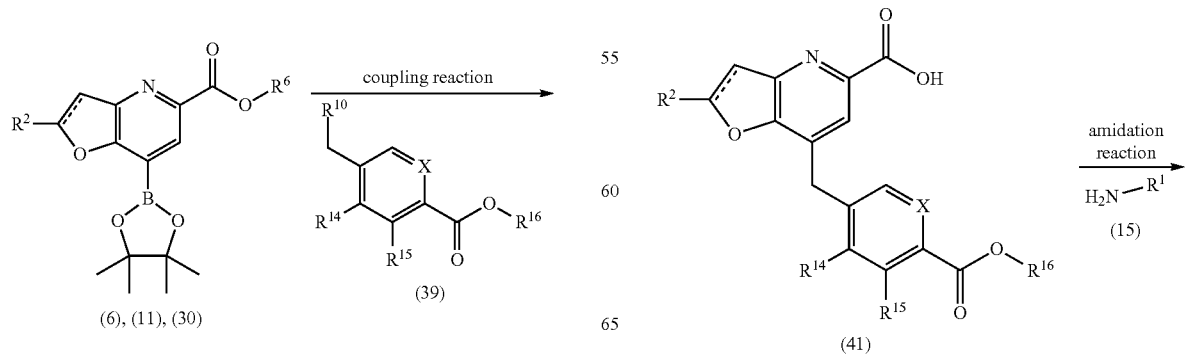

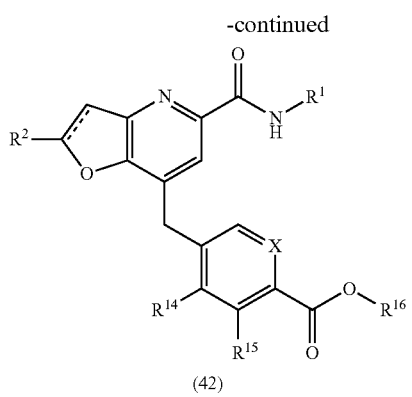

(42)

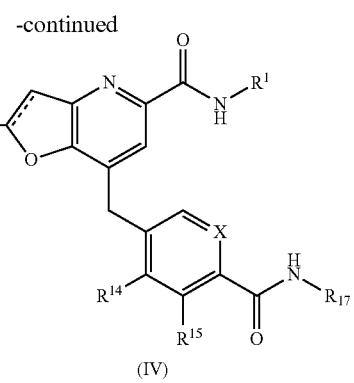

(IV)

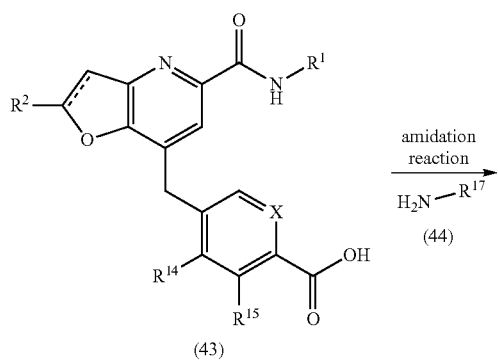

(43)

In the reaction formulas, X is $CR^{6A}$ or N, $R^{14}$ and $R^{15}$ are each independently a hydrogen atom, a halogen atom, an optionally substituted $C_{1-6}$ alkyl group, or an optionally substituted $C_{1-6}$ alkoxy group, $R^{16}$ is a protecting group of a carboxyl group, $R^{17}$ is a substituent, and $R^1$, $R^2$, $R^6$, $R^{10}$ and $R^{6A}$ mean the same as above.

Compound (40) can be produced by a coupling reaction of compound (6), compound (11) or compound (30) and compound (39) in the presence of a metal catalyst.

Compound (41) can be produced by hydrolysis of compound (40).

Compound (42) can be produced by an amidation reaction of compound (41) and compound (15).

Compound (43) can be produced by hydrolysis of compound (42).

Compound (IV) can be produced by an amidation reaction of compound (43) and compound (44).

Of compound (I), compound (V) and compounds (V') wherein one of $R^3$ and $R^4$ is a $C_{1-6}$ alkyl group, and the other is a hydrogen atom, and ring A has an optionally substituted carbamoyl group can be produced from compound (6) or (11) by the following method.

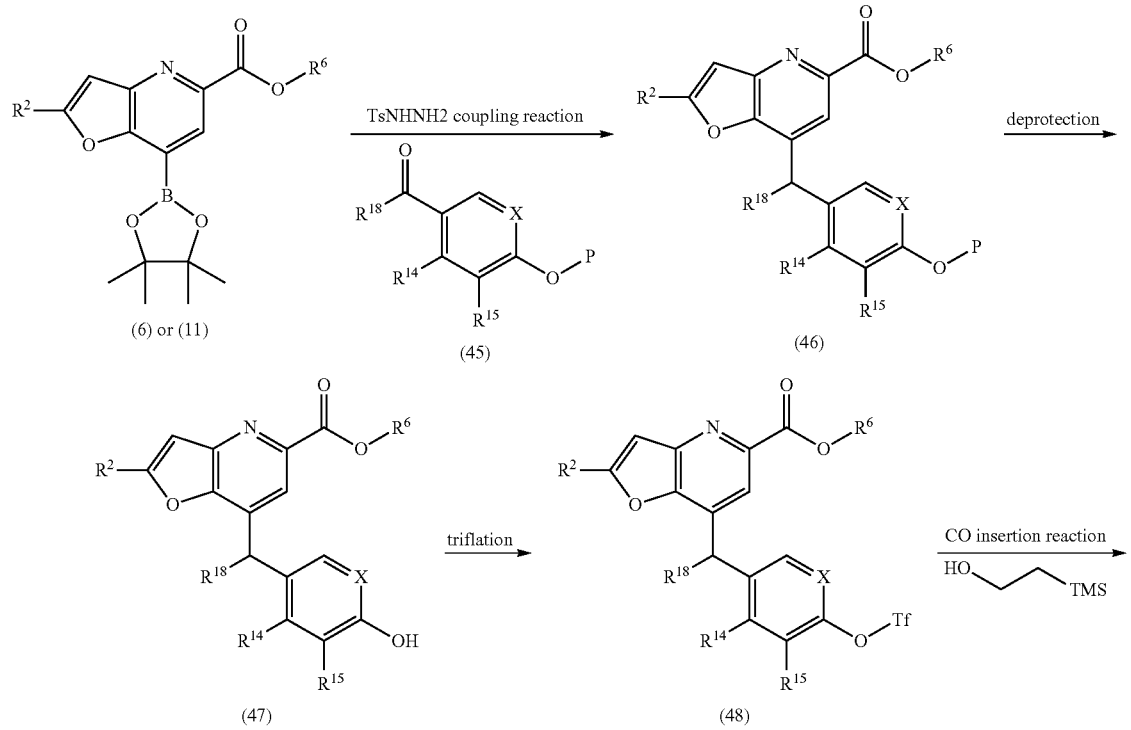

-continued

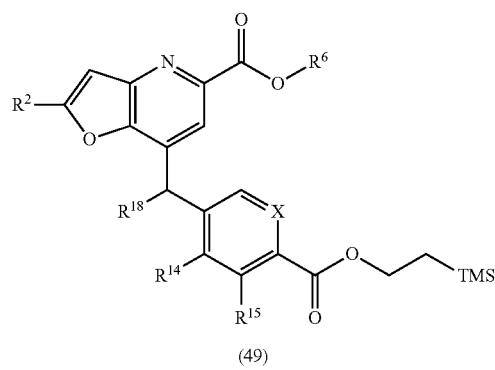
(49)

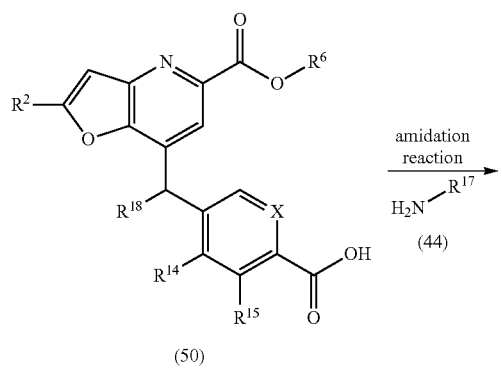
(50)

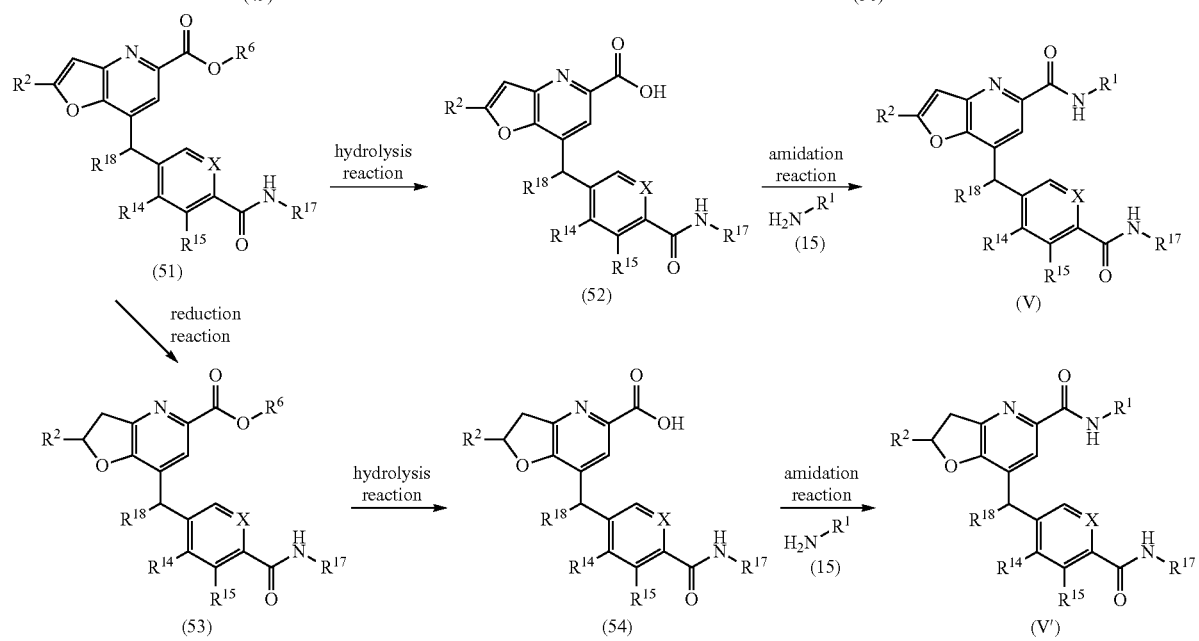

In the reaction formulas, $R^{18}$ is a $C_{1-6}$ alkyl group, P is a protecting group of the phenolic hydroxyl group, Tf is a trifluoromethylsulfonyl group, TMS is a trimethylsilyl group, and X, $R^1$, $R^2$, $R^6$, $R^{14}$, $R^{15}$ and $R^{17}$ mean the same as above.

Compound (46) can be produced by a coupling reaction of compound (6) or (11) and compound (45) in the presence of p-toluenesulfonylhydrazide and an inorganic base according to the method described in (literature) Tetrahedron, 73, 785-793 (2017). As the inorganic base, potassium carbonate, potassium phosphate and the like can be mentioned.

Compound (47) can be produced by deprotection of the protecting group of compound (46).

Compound (48) can be produced by sulfonic acid esterification of compound (47) using trifluoromethanesulfonic anhydride.

Compound (49) can be produced by a carbon monoxide insertion reaction of compound (48) in the presence of 2-(trimethylsilyl)ethanol, carbon monoxide, a base and a metal catalyst.

Compound (50) can be produced by deprotection of compound (49).

Compound (51) can be produced by an amidation reaction of compound (50) and compound (44).

Compound (52) can be produced by hydrolysis of compound (51).

Compound (V) can be produced by an amidation reaction of compound (52) and compound (15).

Compound (53) can be produced by a reduction reaction of compound (51).

Compound (54) can be produced by hydrolysis of compound (53).

Compound (V') can be produced by an amidation reaction of compound (54) and compound (15).

Compound (1), compound (8), compound (9), compound (12), compound (15), compound (16), compound (28), compound (39), compound (44), compound (45), alkyl halide (36), zinc cyanide, trimethylsilylacetylene, bis(pinacolato)diboron, p-toluenesulfonylhydrazide and 2-(trimethylsilyl)ethanol used as starting materials for the production of compounds (IA), (IB), (I'), (II), (III), (III'), (IV), (V) and (V') may be commercially available products or can be produced according to a method known per se.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from the compound is also encompassed in compound (I).

The optical isomer can be produced according to a method known per se. To be specific, an optically active synthetic intermediate is used, or the final racemate product is subjected to optical resolution according to a conventional method to give an optical isomer.

For example, the method of optical resolution may be a method known per se, such as a fractional recrystallization method, a chiral column method, a diastereomer method etc.

1) Fractional Recrystallization Method

A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series manufactured by Daicel Corporation and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis reaction and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis reaction.

When compound (I) is obtained as a free compound, the compound can be converted to an objective salt according to a method known per se or a method analogous thereto. Conversely, when it is obtained as a salt, the salt can be converted to a free form or other objective salt by a method known per se or a method analogous thereto.

compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, t-butylation and the like);

a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like);

a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be used for the prophylaxis or treatment of diseases, for example, (1) constipation, for example, neurogenic constipation (constipation associated with diseases such as Parkinson's disease, multiple sclerosis, spinal cord injury, Alzheimer's disease, Hirschsprung's syndrome, Chagas' disease, and the like), idiopathic constipation, functional constipation, flaccid constipation, irritable bowel syndrome with constipation, constipation possibly complicated by other disease (Parkinson's disease, spinal cord injury, multiple sclerosis, etc.), age-related constipation, various drug-induced constipation (opioid agonist-induced constipation and the like), primary chronic constipation, drug-induced constipation (opioid, anticholinergic agent, calcium antagonist, anticancer agent, heavy metal toxicosis, and the like), constipation associated with underlying diseases such as endocrine diseases or metabolic abnormality (hypopituitarism, hypothyroidism, pheochromocytoma, and the like), muscle abnormalities disease (familial visceral skeletal muscle atrophy, scleroderma, amyloidosis, progressive systemic sclerosis, and the like), metabolic diseases (diabetes, porphyria, uremia, hypokalemia, hypercalcemia, and the like) and the like, (2) digestive diseases [e.g., gastric ulcer, duodenal ulcer, gastric hypomotility such as gastroparalysis and the like, post-operative gastrointestinal paralysis, upper gastrointestinal motility disorder and discomfort, nausea, vomiting, erosive esophagitis, antiinflammatory agents (non-steroidal antiinflammatory agents)-induced gastrointestinal disorder, irritable bowel syndrome, inflammatory bowel disease, ulcerative colitis, Crohn's disease, stress gastrointestinal disorder, diarrhea, postoperative ileus], (3) psychiatric diseases [e.g., depression, major depression, bipolar depression, dysthymic disorder, emotional disorder (seasonal affective disorder and the like), recurrent depression, postpartum depression, stress disorder, depression symptom, mania, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autism spectrum syndrome, fragile X syndrome, Rett syndrome, adjustment disorder, bipolar disorder, neurosis, schizophrenia (e.g., positive symptom, negative symptom, and cognitive impairment), cognitive impairment associated with schizophrenia, chronic fatigue syndrome, anxiety neurosis, compulsive neurosis, epilepsy, anxiety symptom, anxious mental state, emotional abnormality, cyclothymia, nervous erethism, faint, addiction, low sex drive, attention deficit hyperactivity disorder (ADHD), psychotic major depression, intractable major depression, treatment-resistant depression], (4) neurodegenerative diseases [e.g., Alzheimer's disease, Alzheimer-type senile dementia, Parkinson's disease, Parkinson's disease dementia, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's syndrome, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, multiple sclerosis], (5) age-related cognition and memory disorders [e.g., age-related memory disorders, senile dementia], (6) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (7) respiratory depression caused by anesthetics, traumatic disease, or neurodegenerative disease and the like, (8) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular convulsion, Meniere's disease, autonomic ataxia, alopecia, glaucoma, hypertension, cardiac disease, tachycardia, congestive cardiac failure, hyperpnea, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, metabolic syndrome, osteoporosis, incontinence, dysuria, bladder functional disorder, (9) pain, and the like in mammals (e.g., mouse, rat, hamster, rabbit, cat, dog, bovine, sheep, monkey, human etc.). Particularly preferably, compound (I) may be used for the prophylaxis or treatment of neurogenic constipation (constipation associated with diseases such as Parkinson's disease, multiple sclerosis, spinal cord injury, Alzheimer's disease, Hirschsprung's syndrome, Chagas' disease, and the like), idiopathic constipation, functional constipation, flaccid constipation, irritable bowel syndrome with constipation, constipation possibly complicated by other disease (Parkinson's disease, spinal cord injury, multiple sclerosis, etc.), age-related constipation, various drug-induced constipation (opioid agonist-induced constipation and the like), primary chronic constipation, drug-induced constipation (opioid, anticholinergic agent, calcium antagonist, anticancer agent, heavy metal toxicosis, and the like), constipation associated with underlying diseases such as endocrine diseases or metabolic abnormality (hypopituitarism, hypothyroidism, pheochromocytoma, and the like), muscle abnormalities disease (familial visceral skeletal muscle atrophy, scleroderma, amyloidosis, progressive systemic sclerosis, and the like), metabolic diseases (diabetes, porphyria, uremia, hypokalemia, hypercalcemia, and the like) and the like.

Since compound (I) may have a cholinergic muscarinic M1 receptor positive allosteric modulator activity, it is expected to provide an excellent prophylactic or therapeutic effect for the above-mentioned diseases.

Generally, it is desirable that the therapeutic drugs for constipation exhibit effect promptly after administration and then the effect disappears quickly. Compound (I) is expected to show superior pharmacokinetics as a therapeutic drug for constipation and may be expected to exhibit effect within, for example, 3 hr after administration, preferably 2 hr after administration, further preferably 1 hr after administration, and the effect may be expected to disappear quickly thereafter.

Cholinergic muscarinic M1 receptor is known to express in the brain and gastrointestinal nerve plexus. Compound (I) is expected to show low central nervous system permeability, function efficiently in periphery and show excellent effect as a therapeutic drug for constipation. Regarding central nervous system permeability, for example, corrected efflux ratio of MDR1 in MDR1 membrane permeability test is preferably not less than 2.0, more preferably not less than 3.0, and furthermore preferably not less than 5.0.

Since compound (I) may be expected to be excellent in solubility in water, the Japanese Pharmacopoeia dissolution test 2nd fluid, or the Japanese Pharmacopoeia disintegration test 2nd fluid, excellent in pharmacokinetics (e.g., plasma drug half-life, metabolic stability, CYP inhibition), show low toxicity (e.g., more excellent as a medicament in terms of acute toxicity, chronic toxicity, genetic toxicity, reproductive toxicity, cardiotoxicity, drug interaction, carcinogenicity, phototoxicity and the like), and may also have excellent properties as a pharmaceutical product such as a few side effects and the like, it can be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

A medicament containing compound (I) (sometimes to be abbreviated as "medicament of the present invention" in the present specification) may have any form (preparation form) of a solid preparation such as powder, granule, tablet, capsule, orally disintegrable film and the like, or a liquid agent such as syrup, emulsion, injection and the like.

The medicament of the present invention may be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation can be produced according to the method described in JP-A-9-263545.

In the medicament of the present invention, the content of compound (I) varies depending on the form of the preparation, but is generally 0.01 to 100% by weight, preferably 0.1 to 50% by weight, more preferably 0.5 to 20% by weight, as the amount of compound (I) relative to the whole preparation (whole medicament).

Compound (I) may be used alone or in admixture with a suitable, pharmacologically acceptable carrier, for example, excipients (e.g., starch, lactose, white soft sugar, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and administered orally or parenterally. When compound (I) is formed as a preparation for topical administration, it can also be directly administered to the affected part of an articular disease. In this case, an injection is preferable. Compound (I) can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound together with vegetable oil such as sesame oil, corn oil and the like or a mixture thereof with a phospholipid such as lecithin and the like, or medium-chain fatty acid triglyceride (e.g., miglyol 812 etc.) to give an injection to be actually used.

The dose of compound (I) varies depending on the subject of administration, administration route and symptoms and is not particularly limited. For example, for oral administration to adult patients (body weight adult 40 to 80 kg, for example, 60 kg) with constipation, the dose may be, for example, 0.001 to 1000 mg/kg body weight/day, preferably 0.01 to 100 mg/kg body weight/day, more preferably 0.1 to 10 mg/kg body weight/day, as compound (I). This amount may be administered in one to three portions per day.

The medicament of the present invention may be able to use the compound (I) solely or as a pharmaceutical composition of compound (I) mixed with a pharmacologically acceptable carrier according to a method known per se (e.g., the method described in the Japanese Pharmacopoeia etc.) as the production method of a pharmaceutical preparation. The medicament of the present invention may be administered safely in the form of, for example, a pharmaceutical composition such as tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal, lesion and the like).

As the aforementioned "pharmacologically acceptable carrier", various organic or inorganic carriers conventionally used as preparation materials (starting materials) may be used. For example, excipient, lubricant, binder, disintegrant and the like may be used for solid preparations, and solvent, solubilizing agent, suspending agent, isotonic agent, buffer, soothing agent and the like may be used for liquid preparations. Where necessary, preparation additives such as preservative, antioxidant, colorant, sweetening agent and the like may also be used.

Examples of the excipient include lactose, white soft sugar, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white soft sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphate salts, acetate salts, carbonate salts, citrate salts and the like.

Examples of the soothing agent include benzyl alcohol and the like.

Examples of the preservative include p-oxybenzoate esters, chlorobutanol, benzyl alcohol, phenylethyl alcohol, dehydroacetic acid, sorbic acid and the like.

Examples of the antioxidant include sulfite salts, ascorbic acid, α-tocopherol and the like.

While the pharmaceutical composition varies according to the dosage form, administration method, carrier and the like, it may be produced according to a conventional method by adding compound (I) in a proportion of generally 0.01-100% (w/w), preferably 0.1-95% (w/w), of the total amount of the preparation.

Compound (I) may be used in combination with other active ingredients (hereinafter to be abbreviated as concomitant drug)

Examples of the concomitant drug include the following.

Prokinetic agent (cholinesterase inhibitor (neostigmine, physostigmine etc.), 5-HT$_4$ agonist, ghrelin agonist (capromorelin etc.), motilin receptor agonist (camicinal, erythromycin etc.), opioid antagonist (naltrexone, naloxegol etc.)), intestinal water secretion promoter (guanylate cyclase C agonist (linaclotide etc.), chloride channel 2 opener (lubiprostone etc.), sodium/proton exchanger 3 inhibitor (tenapanor etc.)), anti-constipation drug (sennoside, magnesium oxide, magnesium hydroxide, bisacodyl, polycarbophil calcium, laxative sugars (lactulose etc.), laxoberon, crude drug having an anti-constipation action (psyllium etc.) etc.), benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-HT$_{1A}$ agonist (buspirone hydrochloride, tandospirone citrate, osemozotan hydrochloride etc.), 5-HT$_3$ antagonist (cyamemazine etc.), non-cardioselective β blocker (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (aprepitant, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, combination of those drugs etc.), therapeutic drug for Parkinson's disease dementia (rivastigmine), therapeutic drug for Lewy body dementia (donepezil), therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for behavior abnormalities or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining compound (I) and a concomitant drug, a superior effect such as
(1) the dose may be reduced as compared to single administration of the compound (I) or a concomitant drug,
(2) the drug to be combined with the compound (I) may be selected according to the condition of patients (mild case, severe case and the like), (3) the period of treatment may be set longer by selecting a concomitant drug having different action and mechanism from the compound (I), (4) a sustained treatment effect may be designed by selecting a concomitant drug having different action and mechanism from the compound (I), (5) a synergistic effect may be afforded by a combined use of the compound (I) and a concomitant drug, and the like, can be achieved.

Hereinafter compound (I) and a concomitant drug used in combination are referred to as the "combination agent of the present invention".

When using the combination agent of the present invention, the administration time of compound (I) and the concomitant drug is not restricted, and compound (I) or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that compound (I) and the concomitant drug are combined in administration. Examples of the administration mode include the following methods:

(1) administration of a single preparation obtained by simultaneously processing compound (I) and the concomitant drug, (2) simultaneous administration of two kinds of preparations of compound (I) and the concomitant drug, which have been separately produced, by the same administration route, (3) administration of two kinds of preparations of compound (I) and the concomitant drug, which have been separately produced, by the same administration route in a staggered manner, (4) simultaneous administration of two kinds of preparations of compound (I) and the concomitant drug, which have been separately produced, by different administration routes, (5) administration of two kinds of preparations of compound (I) and the concomitant drug, which have been separately produced, by different administration routes in a staggered manner (e.g., administration in the order of compound (I) and the concomitant drug, or in the reverse order) and the like.

The combination agent of the present invention can be expected to show low toxicity. For example, compound (I) or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions may be administered safely orally or non-orally (e.g., topical, rectal, intravenous administration etc.) Injection may be administered intravenously, intramuscularly, subcutaneously, or by intraorgan administration or directly to the lesion.

As the pharmacologically acceptable carriers that may be used for the production of a combination agent in the present invention, various organic or inorganic carrier substances conventionally used as preparation materials may be used. For solid preparations, for example, excipient, lubricant, binder and disintegrant may be used. For liquid preparations, for example, solvent, solubilizing agent, suspending agent, isotonic agent, buffering agent, soothing agent and the like may be used. Where necessary, a suitable amount of conventional preservative, antioxidant, colorant, sweetening agent, adsorbent, wetting agent and the like may be used as appropriate.

Examples of the excipient include lactose, white soft sugar, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white soft sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphate salts, acetate salts, carbonate salts, citrate salts and the like.

Examples of the soothing agent include benzyl alcohol and the like.

Examples of the preservative include p-oxybenzoate esters, chlorobutanol, benzyl alcohol, phenylethyl alcohol, dehydroacetic acid, sorbic acid and the like.

Examples of the antioxidant include sulfite salts, ascorbic acid, α-tocopherol and the like.

The mixing ratio of compound (I) to the concomitant drug in the combination agent of the present invention can be appropriately selected depending on an administration subject, administration route, diseases and the like.

For example, the content of compound (I) in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of the concomitant drug in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of additives such as a carrier and the like in the combination agent of the present invention differs depending on the form of a preparation, and usually from about 1 to 99.99 wt %, preferably from about 10 to 90 wt %, based on the whole preparation.

When compound (I) and a concomitant drug are separately formulated into preparations, the contents thereof are similar to the above.

EXAMPLE

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

Elution in column chromatography in the Examples was performed under observation by TLC (Thin Layer Chromatography) unless particularly indicated. In the TLC observation, 60 $F_{254}$ manufactured by Merck was used as a TLC plate, and the solvent used as an eluent in the column chromatography was used as an elution solvent. For detection, a UV detector was employed. In silica gel column chromatography, the indication of NH means use of aminopropylsilane-bonded silica gel, and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio of elution solvents is, unless otherwise specified, a volume mixing ratio.

For the analysis of $^1$H NMR, ACD/SpecManager (trade name) software and the like were used. Very mild peaks for protons of a hydroxy group, an amino group and the like may not be described.

MS was measured by LC/MS. As ionization method, ESI method or APCI method was used. The data indicates those found. Generally, molecular ion peaks are observed but may sometimes be observed as a fragment ion. In the case of a salt, generally, a molecular ion peak or a fragment ion peak of a free form is observed.

The unit of the sample concentration (c) by optical rotation ($[α]_D$) is g/100 mL.

Elemental analytical value (Anal.) shows calculated value (Calcd) and measured value (Found).

The peak in powder X-ray diffraction in the Examples means a peak measured using Cu Kα ray as a radiation source and Ultima IV (Rigaku Corporation, Japan) at room temperature. The measurement conditions are as follows.

Electric pressure/Electric current: 40 kV/50 mA
Scan speed: 6 degree/min
Scan range of 2 Theta: 2-35 degree The crystallinity by powder X-ray diffraction in the Examples was calculated by the Hermans method.

In Examples, the following abbreviations are used.
mp: melting point
MS: mass spectrum
M: mol concentration
N: normality
CDCl$_3$: deuterochloroform
DMSO-d$_6$: hexadeuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
AIBN: 2,2'-azobis(isobutyronitrile)
DAST: (diethylamino)sulfur trifluoride
DCM: dichloromethane
DIPEA: N,N-diisopropylethylamine
DMA: N,N-dimethylacetamide
DME: 1,2-dimethoxyethane
DMF: N,N-dimethylformamide
DMSO: dimethyl sulfoxide
DMT-MM: 4-(4,6-dimethoxy-1,3,5-triazin-2-yl)-4-methylmorpholinium chloride n-hydrate
EtOH: ethanol
HATU: O-(7-azabenzotriazol-1-yl)-N,N,N',N'-tetramethyluronium hexafluorophosphate
HOBt: 1-hydroxybenzotriazole
HOBt·H$_2$O: 1-hydroxybenzotriazole hydrate
IPE: diisopropyl ether
LAH: lithium aluminum hydride
MeOH: methanol
MEK: methyl ethyl ketone
NBS: N-bromosuccinimide
Pd(PPh$_3$)$_4$: tetrakis (triphenylphosphine)palladium(0)
Pd$_2$(dba)$_3$: tris (dibenzylideneacetone)dipalladium(0)
PdCl$_2$(dppf): [1,1'-bis(diphenylphosphino)ferrocene]palladium(II) dichloride
PdCl$_2$(dppf)·DCM: [1,1'-bis(diphenylphosphino)ferrocene]palladium(II) dichloride dichloromethane complex
TEA: triethylamine
TFA: trifluoroacetic acid
THF: tetrahydrofuran
WSC: 1-ethyl-3-(3-dimethylaminopropyl)carbodiimide
WSC·HCl: 1-ethyl-3-(3-dimethylaminopropyl)carbodiimide hydrochloride
tRn(n=1-4): retention time by high performance liquid chromatography (number shows the order of elution)

Example 1

N-((1S,2S)-2-hydroxycyclopentyl)-7-(4-(1H-pyrazol-1-yl)benzyl)-2,3-dihydrofuro[3,2-b]pyridine-5-carboxamide A) methyl 4-chloro-5-hydroxypyridine-2-carboxylate To a mixture of methyl 4-chloro-5-methoxypyridine-2-carboxylate (3.85 g) and anhydrous DCM (200 mL) was added aluminum chloride (25.5 g) at room temperature, and the mixture was heated under reflux under a nitrogen atmosphere for 16 hr. The reaction mixture was added to ice water (150 mL) to terminate the reaction, and the mixture was extracted with DCM/THF (10:1). The organic layer was dried over anhydrous sodium sulfate and concentrated under reduced pressure to give the title compound (3.15 g).

$^1$H NMR (400 MHz, CDCl$_3$) δ 3.98 (3H, s), 5.61 (1H, brs), 8.18 (1H, s), 8.46 (1H, s).

B) methyl 4-chloro-5-hydroxy-6-iodopyridine-2-carboxylate

To a mixture of methyl 4-chloro-5-hydroxypyridine-2-carboxylate (15.1 g), potassium carbonate (11.1 g) and water (150 mL) was added iodine (30.8 g) at room temperature, and the mixture was stirred at 50° C. for 16 hr. The solid was filtered off, and the filtrate was washed with ethyl acetate. To the aqueous layer was added saturated aqueous sodium thiosulfate solution, and the mixture was adjusted to pH 1 with concentrated hydrochloric acid and extracted with ethyl acetate/THF (1/1). The organic layer was dried over anhydrous sodium sulfate and concentrated under reduced pressure to give the title compound (23.5 g).
$^1$H NMR (400 MHz, CDCl$_3$) δ 3.95 (3H, s), 5.90 (1H, brs), 8.06 (1H, s).

C) methyl 7-chloro-2-(trimethylsilyl)furo[3,2-b]pyridine-5-carboxylate

A mixture of methyl 4-chloro-5-hydroxy-6-iodopyridine-2-carboxylate (24.5 g), trimethylsilylacetylene (8.05 g), PdCl$_2$(dppf) (2.75 g), copper(I) iodide (745 mg), TEA (31.6 mL) and dehydrated THF (300 mL) was stirred under a nitrogen atmosphere at 10° C. for 16 hr. The solvent was evaporated under reduced pressure, and the residue was purified by silica gel column chromatography (ethyl acetate/petroleum ether) to give the title compound (14.4 g).
$^1$H NMR (400 MHz, CDCl$_3$) δ 0.41 (9H, s), 4.04 (3H, s), 7.25 (1H, s), 8.14 (1H, s).

D) methyl 7-chlorofuro[3,2-b]pyridine-5-carboxylate

To a mixture of methyl 7-chloro-2-(trimethylsilyl)furo[3,2-b]pyridine-5-carboxylate (14.4 g) and dehydrating MeOH (200 mL) was added potassium fluoride (8.85 g), and the mixture was stirred at 10° C. for 16 hr. The solvent was evaporated under reduced pressure, water was added to the residue, and the mixture was extracted with ethyl acetate/THF (1/1). The organic layer was washed with saturated brine, dried over anhydrous sodium sulfate, and concentrated under reduced pressure to give the title compound (9.12 g).
MS: [M+H]$^+$ 211.8.

E) methyl 7-(4,4,5,5-tetramethyl-1,3,2-dioxaborolan-2-yl)furo[3,2-b]pyridine-5-carboxylate To a mixture of bis(pinacolato)diboron (9.00 g), methyl 7-chlorofuro[3,2-b]pyridine-5-carboxylate (5.00 g), 2-dicyclohexylphosphino-2',4',6'-triisopropyl-1,1'-biphenyl (0.811 g), potassium acetate (4.64 g) and dehydrated THF (100 mL) was added Pd$_2$(dba)$_3$ (0.782 g) at room temperature. The mixture was stirred under a nitrogen atmosphere at 65° C. for 3 hr and cooled to room temperature. The mixture was diluted with ethyl acetate and added to water, and the precipitated solid was filtered off. The filtrate was washed with water and saturated brine, dried over anhydrous sodium sulfate, and concentrated under reduced pressure. To the residue was added IPE, and the solid was collected by filtration and washed with IPE to give the title compound (3.77 g).
$^1$H NMR (300 MHz, CDCl$_3$) δ 1.43 (12H, s), 4.04 (3H, s), 7.11 (1H, d, J=2.6 Hz), 8.02 (1H, d, J=2.3 Hz), 8.50 (1H, s).

F) methyl 7-(4-(1H-pyrazol-1-yl)benzyl)furo[3,2-b]pyridine-5-carboxylate

To a mixture of methyl 7-(4,4,5,5-tetramethyl-1,3,2-dioxaborolan-2-yl)furo[3,2-b]pyridine-5-carboxylate (150 mg), 1-(4-(chloromethyl)phenyl)-1H-pyrazole (95 mg), sodium carbonate (105 mg), DME (3.0 mL) and water (1.0 mL) was added PdCl$_2$(dppf) (18.1 mg) at room temperature. Under an argon atmosphere, the mixture was stirred at 80° C. for 1 hr, diluted with ethyl acetate at room temperature, and added to water. The organic layer was washed with water and saturated brine, dried over anhydrous sodium sulfate, and concentrated under reduced pressure. The residue was purified by silica gel column chromatography (ethyl acetate/hexane) to give the title compound (114 mg).
MS: [M+H]$^+$ 334.2.

G) methyl 7-(4-(1H-pyrazol-1-yl)benzyl)-2,3-dihydrofuro[3,2-b]pyridine-5-carboxylate A mixture of methyl 7-(4-(1H-pyrazol-1-yl)benzyl)furo[3,2-b]pyridine-5-carboxylate (2.55 g), 10% palladium-carbon (1.25 g) and EtOH (150 mL) was stirred under a hydrogen atmosphere of 55 psi (3.79 kPa) at 20° C. for 3 days. The catalyst was filtered off, and the filtrate was concentrated under reduced pressure to give the title compound (2.04 g).
$^1$H NMR (400 MHz, CDCl$_3$) δ 3.42 (2H, t, J=8.8 Hz), 3.91-3.96 (5H, m), 4.76 (2H, t, J=8.8 Hz), 6.45 (1H, t, J=2.0 Hz), 7.30 (2H, d, J=8.4 Hz), 7.62 (2H, d, J=8.4 Hz), 7.71 (1H, d, J=1.2 Hz), 7.79 (1H, s), 7.89 (1H, d, J=2.4 Hz).

H) 7-(4-(1H-pyrazol-1-yl)benzyl)-2,3-dihydrofuro[3,2-b]pyridine-5-carboxylic acid A mixture of methyl 7-(4-(1H-pyrazol-1-yl)benzyl)-2,3-dihydrofuro[3,2-b]pyridine-5-carboxylate (2.04 g), lithium hydroxide monohydrate (1.28 g) and THF/MeOH/water (3/1/1, 35 mL) was stirred at 10° C. for 16 hr. The solvent was evaporated under reduced pressure. To a mixture of the residue and water (50 mL) was added concentrated hydrochloric acid to adjust pH to 1, and the mixture was stirred at 10° C. for 0.5 hr. The precipitated solid was collected by filtration and dried to give the title compound (1.50 g).
MS: [M+H]$^+$ 321.9.

I) N-((1S,2S)-2-hydroxycyclopentyl)-7-(4-(1H-pyrazol-1-yl)benzyl)-2,3-dihydrofuro[3,2-b]pyridine-5-carboxamide A mixture of 7-(4-(1H-pyrazol-1-yl)benzyl)-2,3-dihydrofuro[3,2-b]pyridine-5-carboxylic acid (360 mg), (1S,2S)-2-aminocyclopentanol hydrochloride (232 mg), WSC·HCl (439 mg), HOBt (151 mg), DIPEA (433 mg) and DMF (10 mL) was stirred under a nitrogen atmosphere at 10° C. for 16 hr. The mixture was added to water and extracted with ethyl acetate. The organic layer was washed with saturated brine, dried over anhydrous sodium sulfate, and concentrated under reduced pressure. The residue was purified by preparative thin layer chromatography (petroleum ether/ethyl acetate) to give the title compound (310 mg).

Example 4

N-((1S,2S)-2-hydroxycyclohexyl)-7-(4-(1H-pyrazol-1-yl)benzyl)furo[3,2-b]pyridine-5-carboxamide

A) 7-(4-(1H-pyrazol-1-yl)benzyl)furo[3,2-b]pyridine-5-carboxylic acid

The title compound was obtained by a method similar to that in step H of Example 1.
MS: [M+H]$^+$ 320.2.

B) N-((1S,2S)-2-hydroxycyclohexyl)-7-(4-(1H-pyrazol-1-yl)benzyl)furo[3,2-b]pyridine-5-carboxamide The title compound was obtained by a method similar to that in step I of Example 1.

Example 5

N-((1S,2S)-2-hydroxycyclohexyl)-7-(4-(1-methyl-1H-pyrazol-3-yl)benzyl)furo[3,2-b]pyridine-5-carboxamide A) methyl 7-(4-(1-methyl-1H-pyrazol-3-yl)benzyl)furo[3,2-b]pyridine-5-carboxylate The title compound was obtained by a method similar to that in step F of Example 1.
MS: [M+H]$^+$ 348.1.

B) 7-(4-(1-methyl-1H-pyrazol-3-yl)benzyl)furo[3,2-b]pyridine-5-carboxylic acid

The title compound was obtained by a method similar to that in step H of Example 1.
MS: [M+H]$^+$ 334.1.

C) N-((1S,2S)-2-hydroxycyclohexyl)-7-(4-(1-methyl-1H-pyrazol-3-yl)benzyl)furo[3,2-b]pyridine-5-carboxamide The title compound was obtained by a method similar to that in step I of Example 1.

Example 8

1,5-anhydro-2,4-dideoxy-2-(((7-(4-(1-methyl-1H-pyrazol-3-yl)benzyl)-2,3-dihydrofuro[3,2-b]pyridin-5-yl)carbonyl)amino)-L-threo-pentitol A) methyl 7-(4-(1-methyl-1H-pyrazol-3-yl)benzyl)-2,3-dihydrofuro[3,2-b]pyridine-5-carboxylate The title compound was obtained by a method similar to that in step G of Example 1.
MS: [M+H]$^+$ 350.1.

B) 7-(4-(1-methyl-1H-pyrazol-3-yl)benzyl)-2,3-dihydrofuro[3,2-b]pyridine-5-carboxylic acid The title compound was obtained by a method similar to that in step H of Example 1.
MS: [M+H]$^+$ 336.1.

C) 1,5-anhydro-2,4-dideoxy-2-(((7-(4-(1-methyl-1H-pyrazol-3-yl)benzyl)-2,3-dihydrofuro[3,2-b]pyridin-5-yl)carbonyl)amino)-L-threo-pentitol The title compound was obtained by a method similar to that in step I of Example 1.

Example 10

N-((1S,2S)-2-hydroxycyclohexyl)-7-((6-methoxypyridin-3-yl)methyl)-2,3-dihydrofuro[3,2-b]pyridine-5-carboxamide A) methyl 7-((6-methoxypyridin-3-yl)methyl)furo[3,2-b]pyridine-5-carboxylate The title compound was obtained by a method similar to that in step F of Example 1.
MS: [M+H]$^+$ 299.1.

B) methyl 7-((6-methoxypyridin-3-yl)methyl)-2,3-dihydrofuro[3,2-b]pyridine-5-carboxylate The title compound was obtained by a method similar to that in step G of Example 1.
MS: [M+H]$^+$ 301.1.

C) 7-((6-methoxypyridin-3-yl)methyl)-2,3-dihydrofuro[3,2-b]pyridine-5-carboxylic acid The title compound was obtained by a method similar to that in step H of Example 1.
MS: [M+H]$^+$ 287.2.

D) N-((1S,2S)-2-hydroxycyclohexyl)-7-((6-methoxypyridin-3-yl)methyl)-2,3-dihydrofuro[3,2-b]pyridine-5-carboxamide The title compound was obtained by a method similar to that in step I of Example 1.

Example 12

N-((1S,2S)-2-hydroxycyclohexyl)-7-(4-methoxybenzyl)-2,3-dihydrofuro[3,2-b]pyridine-5-carboxamide A) methyl 7-(4-methoxybenzyl)furo[3,2-b]pyridine-5-carboxylate The title compound was obtained by a method similar to that in step F of Example 1.
MS: [M+H]$^+$ 298.0.

B) methyl 7-(4-methoxybenzyl)-2,3-dihydrofuro[3,2-b]pyridine-5-carboxylate

The title compound was obtained by a method similar to that in step G of Example 1.
MS: [M+H]$^+$ 300.0.

C) 7-(4-methoxybenzyl)-2,3-dihydrofuro[3,2-b]pyridine-5-carboxylic acid

The title compound was obtained by a method similar to that in step H of Example 1.
MS: [M+H]$^+$ 286.1.

D) N-((1S,2S)-2-hydroxycyclohexyl)-7-(4-methoxybenzyl)-2,3-dihydrofuro[3,2-b]pyridine-5-carboxamide The title compound was obtained by a method similar to that in step I of Example 1.

Example 14

N-((1S,2S)-2-hydroxycyclohexyl)-7-(4-(5-methyl-1,3-thiazol-2-yl)benzyl)-2,3-dihydrofuro[3,2-b]pyridine-5-carboxamide A) (4-(5-methyl-1,3-thiazol-2-yl)phenyl)methanol The title compound was obtained from (4-(hydroxymethyl)phenyl)boronic acid and 2-bromo-5-methyl-1,3-thiazole by a method similar to that in step F of Example 1.
MS: [M+H]$^+$ 206.1.

B) 2-(4-(chloromethyl)phenyl)-5-methyl-1,3-thiazole

To a mixture of (4-(5-methyl-1,3-thiazol-2-yl)phenyl)methanol (3.3 g) and DCM (120 mL) was added thionyl chloride (3.83 g) at 0° C. After stirring at room temperature for 3 hr, saturated aqueous sodium hydrogen carbonate solution was added to the mixture, and the mixture was extracted with DCM. The organic layer was washed with water and saturated brine, dried over anhydrous sodium sulfate, and concentrated under reduced pressure. The residue was purified by silica gel column chromatography (ethyl acetate/petroleum ether) to give the title compound (2.8 g).
MS: [M+H]$^+$ 224.1.

C) methyl 7-(4-(5-methyl-1,3-thiazol-2-yl)benzyl)furo[3,2-b]pyridine-5-carboxylate The title compound was obtained by a method similar to that in step F of Example 1.
MS: [M+H]$^+$ 365.0.

D) methyl 7-(4-(5-methyl-1,3-thiazol-2-yl)benzyl)-2,3-dihydrofuro[3,2-b]pyridine-5-carboxylate The title compound was obtained by a method similar to that in step G of Example 1.
MS: [M+H]$^+$ 367.1.

E) 7-(4-(5-methyl-1,3-thiazol-2-yl)benzyl)-2,3-dihydrofuro[3,2-b]pyridine-5-carboxylic acid The title compound was obtained by a method similar to that in step H of Example 1.
MS: [M+H]$^+$ 353.0.

F) N-((1S,2S)-2-hydroxycyclohexyl)-7-(4-(5-methyl-1,3-thiazol-2-yl)benzyl)-2,3-dihydrofuro[3,2-b]pyridine-5-carboxamide The title compound was obtained by a method similar to that in step I of Example 1.

Example 16

N-((1S,2S)-2-hydroxycyclohexyl)-7-(4-(4-methyl-1,3-thiazol-2-yl)benzyl)-2,3-dihydrofuro[3,2-b]pyridine-5-carboxamide A) (4-(4-methyl-1,3-thiazol-2-yl)phenyl)methanol The title compound was obtained from (4-(hydroxymethyl)phenyl)boronic acid and 2-bromo-4-methyl-1,3-thiazole by a method similar to that in step F of Example 1.
MS: [M+H]$^+$ 206.1.

B) 2-(4-(chloromethyl)phenyl)-4-methyl-1,3-thiazole

The title compound was obtained by a method similar to that in step B of Example 14.
MS: [M+H]$^+$ 224.1.

C) methyl 7-(4-(4-methyl-1,3-thiazol-2-yl)benzyl)furo[3,2-b]pyridine-5-carboxylate The title compound was obtained by a method similar to that in step F of Example 1.
MS: [M+H]$^+$ 365.0.

D) methyl 7-(4-(4-methyl-1,3-thiazol-2-yl)benzyl)-2,3-dihydrofuro[3,2-b]pyridine-5-carboxylate The title compound was obtained by a method similar to that in step G of Example 1.
MS: [M+H]$^+$ 367.0.

E) 7-(4-(4-methyl-1,3-thiazol-2-yl)benzyl)-2,3-dihydrofuro[3,2-b]pyridine-5-carboxylic acid The title compound was obtained by a method similar to that in step H of Example 1.
MS: [M+H]$^+$ 353.1.

F) N-((1S,2S)-2-hydroxycyclohexyl)-7-(4-(4-methyl-1,3-thiazol-2-yl)benzyl)-2,3-dihydrofuro[3,2-b]pyridine-5-carboxamide The title compound was obtained by a method similar to that in step I of Example 1.

Example 18

N-((1S,2S)-2-hydroxycyclohexyl)-7-(4-(2-methyl-1,3-thiazol-5-yl)benzyl)-2,3-dihydrofuro[3,2-b]pyridine-5-carboxamide A) methyl 4-(2-methyl-1,3-thiazol-5-yl)benzoate A mixture of methyl 4-iodobenzoate (1.75 g), 2-methyl-1,3-thiazole (0.99 g), potassium acetate (1.96 g), Pd(PPh$_3$)$_4$ (35 mg) and DMA (60 mL) was stirred at 100° C. overnight. After cooling to room temperature, water was added, and the mixture was extracted with ethyl acetate. The organic layer was dried over anhydrous magnesium sulfate and concentrated under reduced pressure. The residue was purified by silica gel column chromatography (ethyl acetate/DCM) to give the title compound (500 mg).
MS: [M+H]$^+$ 234.1.

B) (4-(2-methyl-1,3-thiazol-5-yl)phenyl)methanol

To a mixture of methyl 4-(2-methyl-1,3-thiazol-5-yl)benzoate (450 mg) and THF (30 mL) was added LAH (147 mg) at 0° C., and the mixture was stirred at room temperature for 2 hr. Water (0.15 mL), 30% aqueous sodium hydroxide solution (0.15 mL) and water (0.45 mL) were successively added dropwise to the mixture. The insoluble material was filtered off, and the filtrate was concentrated under reduced pressure. The residue was purified by silica gel column chromatography (ethyl acetate/petroleum ether) to give the title compound (330 mg).
MS: [M+H]$^+$ 206.1.

C) 5-(4-(chloromethyl)phenyl)-2-methyl-1,3-thiazole

The title compound was obtained by a method similar to that in step B of Example 14.
MS: [M+H]$^+$ 224.1.

D) methyl 7-(4-(2-methyl-1,3-thiazol-5-yl)benzyl)furo[3,2-b]pyridine-5-carboxylate The title compound was obtained by a method similar to that in step F of Example 1.
MS: [M+H]$^+$ 365.1.

E) methyl 7-(4-(2-methyl-1,3-thiazol-5-yl)benzyl)-2,3-dihydrofuro[3,2-b]pyridine-5-carboxylate The title compound was obtained by a method similar to that in step G of Example 1.
MS: [M+H]+ 367.1.

F) 7-(4-(2-methyl-1,3-thiazol-5-yl)benzyl)-2,3-dihydrofuro[3,2-b]pyridine-5-carboxylic acid The title compound was obtained by a method similar to that in step H of Example 1.
MS: [M+H]+ 353.1.

G) N-((1S,2S)-2-hydroxycyclohexyl)-7-(4-(2-methyl-1,3-thiazol-5-yl)benzyl)-2,3-dihydrofuro[3,2-b]pyridine-5-carboxamide The title compound was obtained by a method similar to that in step I of Example 1.

Example 20

1,5-anhydro-2,3-dideoxy-3-(((7-(4-(1-methyl-1H-1,2,3-triazol-4-yl)benzyl)furo[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-1,2,3-triazol-4-yl)benzyl)furo[3,2-b]pyridine-5-carboxamide

A) 5-hydroxy-6-iodopyridine-2-carboxylic acid

To a mixture of 5-hydroxypyridine-2-carboxylic acid (10.0 g), sodium carbonate (15.68 g), potassium iodide (17.54 g) and water (100 mL) was added iodine (17.88 g) at 0° C. The mixture was stirred at 0° C. for 3 hr, the reaction temperature was raised to room temperature, and the mixture was stirred at room temperature overnight. To the mixture was added citric acid monohydrate (32.6 g) at room temperature, and the mixture was stirred at room temperature for 1 hr. The precipitated solid was collected by filtration to give the title compound (13.1 g)
MS: [M+H]+ 266.0.

B) methyl 5-hydroxy-6-iodopyridine-2-carboxylate

To a mixture of 5-hydroxy-6-iodopyridine-2-carboxylic acid (20.0 g) and MeOH (100 mL) was added concentrated sulfuric acid (8.05 mL) at room temperature. The mixture was stirred at 50° C. for 3 hr, and a solution of sodium citrate (39.0 g) in water (100 mL) was added dropwise at 0° C. The precipitated solid was collected by filtration and washed with water to give the title compound (17.7 g).
MS: [M+H]+ 280.0.

C) methyl 2-(trimethylsilyl)furo[3,2-b]pyridine-5-carboxylate

To a mixture of methyl 5-hydroxy-6-iodopyridine-2-carboxylate (10.0 g), TEA (36.3 g) and ethyl acetate (150 mL) were added PdCl$_2$(dppf) (1.31 g) and copper(I) iodide (0.341 g) at room temperature. The mixture was stirred under an argon atmosphere at 15° C. for 5 min. While the internal temperature was maintained at 15-18° C., to the mixture was added dropwise trimethylsilylacetylene (9.93 mL), and the mixture was stirred at room temperature overnight. The insoluble material was filtered off, and the filtrate was concentrated under reduced pressure. The residue was purified by silica gel column chromatography (ethyl acetate/hexane) to give the title compound (6.0 g).
MS: [M+H]+ 250.1.

D) methyl 7-(4,4,5,5-tetramethyl-1,3,2-dioxaborolan-2-yl)-2-(trimethylsilyl)furo[3,2-b]pyridine-5-carboxylate To a mixture of bis(1,5-cyclooctadiene)di-p-methoxy-diiridium(I) (0.052 g), 4,4'-di-tert-butyl-2,2'-bipyridine (0.042 g) and tert-butyl methyl ether (40 mL) was added bis(pinacolato)diboron (4.17 g), and the mixture was stirred under an argon atmosphere at room temperature for 5 min. To the mixture was added methyl 2-(trimethylsilyl)furo[3,2-b]pyridine-5-carboxylate (3.90 g), and the mixture was stirred at 80° C. for 4 hr. After cooling the reaction mixture to room temperature, the solvent was evaporated under reduced pressure. The residue was purified by silica gel column chromatography (ethyl acetate/hexane) to give the title compound (5.87 g).
$^1$H NMR (300 MHz, CDCl$_3$) δ 0.40 (9H, s), 1.42 (12H, s), 4.03 (3H, s), 7.23 (1H, s), 8.41 (1H, s).

E) methyl 7-(4-(1-methyl-1H-1,2,3-triazol-4-yl)benzyl)-2-(trimethylsilyl)furo[3,2-b]pyridine-5-carboxylate A mixture of methyl 7-(4,4,5,5-tetramethyl-1,3,2-dioxaborolan-2-yl)-2-(trimethylsilyl)furo[3,2-b]pyridine-5-carboxylate (5.87 g), 4-(4-(bromomethyl)phenyl)-1-methyl-1H-1,2,3-triazole (4.13 g), PdCl$_2$(dppf) (0.114 g), sodium carbonate (2.486 g), DME (50 mL) and water (10 mL) was stirred under an argon atmosphere at 80° C. for 1 hr. After cooling the reaction mixture to room temperature, water was added to the reaction mixture, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (4.2 g).
MS: [M+H]+ 421.1.

F) methyl 7-(4-(1-methyl-1H-1,2,3-triazol-4-yl)benzyl)furo[3,2-b]pyridine-5-carboxylate To a solution of methyl 7-(4-(1-methyl-1H-1,2,3-triazol-4-yl)benzyl)-2-(trimethylsilyl)furo[3,2-b]pyridine-5-carboxylate (4.2 g) in MeOH (50 mL) was added potassium fluoride (0.87 g) at room temperature, and the mixture was stirred at 80° C. for 4 hr. Water (100 mL) was added to the reaction mixture under stirring at room temperature. The precipitated solid was collected by filtration, washed with water and IPE, and dried under reduced pressure to give the title compound (3.14 g).
MS: [M+H]+ 349.2.

G) 7-(4-(1-methyl-1H-1,2,3-triazol-4-yl)benzyl)furo[3,2-b]pyridine-5-carboxylic acid To a mixture of methyl 7-(4-(1-methyl-1H-1,2,3-triazol-4-yl)benzyl)furo[3,2-b]pyridine-5-carboxylate (13.6 g), water (180 mL) and MeOH (30 mL) was added 2 M aqueous sodium hydroxide solution (39.0 mL) at room temperature.

After stirring at 60° C. for 1 hr, the reaction mixture was filtered through celite to remove the insoluble material. To the filtrate were added water (80 mL) and 2 M hydrochloric acid (50 mL). The mixture was stirred at room temperature for 30 min, and the precipitated solid was collected by filtration. The solid was washed with water and dried under reduced pressure to give the title compound (13.30 g).

MS: [M+H]$^+$ 335.1.

H) 1,5-anhydro-2,3-dideoxy-3-(((7-(4-(1-methyl-1H-1,2,3-triazol-4-yl)benzyl)furo[3,2-b]pyridin-5-yl)carbonyl)amino)-L-threo-pentitol (synonym) 7-(4-(1H-pyrazol-1-yl)benzyl)-N-((3R,4S)-3-hydroxytetrahydro-2H-pyran-4-yl)-2,3-dihydrofuro[3,2-b]pyridine-5-carboxamide To a mixture of 7-(4-(1-methyl-1H-1,2,3-triazol-4-yl)benzyl)furo[3,2-b]pyridine-5-carboxylic acid (14.1 g), (3R,4S)-4-aminotetrahydro-2H-pyran-3-ol hydrochloride (7.13 g), TEA (8.82 mL) and EtOH (200 mL) was added DMT-MM (20.36 g) at room temperature. After stirring at room temperature for 3 hr, water was added to the mixture. The precipitated solid was collected by filtration, washed with water (20 mL), and dried under reduced pressure to give the title compound (14.2 g).

$^1$H NMR (300 MHz, DMSO-d$_6$) δ 1.64 (1H, qd, J=12.1, 4.5 Hz), 1.84 (1H, dd, J=13.0, 4.3 Hz), 3.03 (1H, t, J=10.4 Hz), 3.26-3.41 (1H, m), 3.59 (1H, tt, J=9.8, 5.1 Hz), 3.72-3.89 (3H, m), 4.07 (3H, s), 4.37 (2H, s), 4.96 (1H, d, J=5.7 Hz), 7.23 (1H, d, J=2.3 Hz), 7.39 (2H, d, J=8.3 Hz), 7.78 (2H, d, J=8.3 Hz), 7.92 (1H, s), 8.43-8.50 (2H, m), 8.55 (1H, d, J=8.3 Hz).

Example 22

1,5-anhydro-2,3-dideoxy-3-(((7-(4-(1H-pyrazol-1-yl)benzyl)-2,3-dihydrofuro[3,2-b]pyridin-5-yl)carbonyl)amino)-L-threo-pentitol (synonym) 7-(4-(1H-pyrazol-1-yl)benzyl)-N-((3R,4S)-3-hydroxytetrahydro-2H-pyran-4-yl)-2,3-dihydrofuro[3,2-b]pyridine-5-carboxamide A mixture of 7-(4-(1H-pyrazol-1-yl)benzyl)-2,3-dihydrofuro[3,2-b]pyridine-5-carboxylic acid (106 mg), (3R,4S)-4-aminotetrahydro-2H-pyran-3-ol hydrochloride (60.8 mg), HATU (163 mg), TEA (0.115 mL) and DMF (3.0 mL) was stirred at room temperature overnight. To the reaction mixture was added 5% aqueous sodium hydrogen carbonate solution at room temperature. The mixture was extracted with ethyl acetate, and the organic layer was concentrated under reduced pressure. The residue was purified by silica gel column chromatography (ethyl acetate/hexane) to give the title compound (75 mg).

$^1$H NMR (300 MHz, DMSO-d$_6$) δ 1.59 (1H, qd, J=12.3, 4.7 Hz), 1.81 (1H, dd, J=13.0, 4.3 Hz), 3.01 (1H, t, J=10.4 Hz), 3.25-3.40 (3H, m), 3.46-3.61 (1H, m), 3.66-3.85 (3H, m), 3.97 (2H, s), 4.76 (2H, t, J=8.9 Hz), 4.92 (1H, d, J=5.7 Hz), 6.48-6.56 (1H, m), 7.36 (2H, d, J=8.7 Hz), 7.65-7.80 (4H, m), 8.25 (1H, d, J=8.3 Hz), 8.44 (1H, d, J=2.3 Hz).

Example 25

N-(trans-5,5-difluoro-2-hydroxycyclohexyl)-7-(4-(1H-pyrazol-1-yl)benzyl)-2,3-dihydrofuro[3,2-b]pyridine-5-carboxamide The title compound was obtained by a method similar to that in step I of Example 1.

Example 26

N-(trans-5,5-difluoro-2-hydroxycyclohexyl)-7-(4-(1H-pyrazol-1-yl)benzyl)-2,3-dihydrofuro[3,2-b]pyridine-5-carboxamide (Optical Isomer: Retention Time Short)

N-(trans-5,5-Difluoro-2-hydroxycyclohexyl)-7-(4-(1H-pyrazol-1-yl)benzyl)-2,3-dihydrofuro[3,2-b]pyridine-5-carboxamide (71 mg) obtained in Example 25 was optically resolved by HPLC (CHIRALPAK AD, 50 mmID×500 mmL, mobile phase: hexane/EtOH=200/800), and the material having a shorter retention time (tR1) was triturated with ethyl acetate-IPE to give the title compound (30 mg).

Example 27

N-(trans-5,5-difluoro-2-hydroxycyclohexyl)-7-(4-(1H-pyrazol-1-yl)benzyl)-2,3-dihydrofuro[3,2-b]pyridine-5-carboxamide (Optical Isomer: Retention Time Long)

N-(trans-5,5-Difluoro-2-hydroxycyclohexyl)-7-(4-(1H-pyrazol-1-yl)benzyl)-2,3-dihydrofuro[3,2-b]pyridine-5-carboxamide (71 mg) obtained in Example 25 was optically resolved by HPLC (CHIRALPAK AD, 50 mmID×500 mmL, mobile phase: hexane/EtOH=200/800), and the material having a longer retention time (tR2) was triturated with ethyl acetate-IPE to give the title compound (33 mg).

Example 29

1,5-anhydro-2,3-dideoxy-3-(((7-((6-(1-methyl-1H-pyrazol-3-yl)pyridin-3-yl)methyl)-2,3-dihydrofuro[3,2-b]pyridin-5-yl)carbonyl)amino)-L-threo-pentitol A) 6-(1-methyl-1H-pyrazol-3-yl)nicotinaldehyde The title compound was obtained from 6-chloronicotinaldehyde and 1-methyl-3-(4,4,5,5-tetramethyl-1,3,2-dioxaborolan-2-yl)-1H-pyrazole by a method similar to that in step F of Example 1.

$^1$H NMR (400 MHz, CDCl$_3$) δ 4.01 (3H, s), 6.97 (1H, d, J=2.45 Hz), 7.45 (1H, d, J=2.45 Hz), 8.08 (1H, d, J=8.4 Hz), 8.19 (1H, dd, J=8.31, 1.96 Hz), 9.05 (1H, d, J=1.47 Hz), 10.09 (1H, s).

B) (6-(1-methyl-1H-pyrazol-3-yl)pyridin-3-yl)methanol

To a mixture of 6-(1-methyl-1H-pyrazol-3-yl)nicotinaldehyde (25.0 g) and MeOH (375 mL) was added sodium borohydride (10.16 g) at 0° C., and the mixture was stirred at room temperature for 16 hr. To the reaction mixture was added water, and the mixture was extracted with ethyl acetate. The organic layer was washed with saturated brine and dried over anhydrous magnesium sulfate, and the solvent was evaporated under reduced pressure. The residue was purified by silica gel column chromatography (ethyl acetate/hexane) to give the title compound (18.0 g).

$^1$H NMR (500 MHz, CDCl$_3$) δ1.81 (1H, brs), 3.98 (3H, s), 4.74 (2H, d, J=4.88 Hz), 6.85 (1H, d, J=2.44 Hz), 7.41 (1H, d, J=2.44 Hz), 7.74 (1H, dd, J=8.09, 2.29 Hz), 7.90 (1H, d, J=7.93 Hz), 8.59 (1H, d, J=1.83 Hz).

C) 5-(chloromethyl)-2-(1-methyl-1H-pyrazol-3-yl)pyridine

To a mixture of (6-(1-methyl-1H-pyrazol-3-yl)pyridin-3-yl)methanol (18.0 g), TEA (11.16 mL) and DCM (270 mL) was added dropwise methanesulfonyl chloride (7.3 mL) at 0° C. The mixture was stirred at room temperature for 16 hr, water was added, and the mixture was extracted with DCM. The organic layer was washed with saturated brine and dried over anhydrous sodium sulfate, and the solvent was evaporated under reduced pressure. The residue was purified by silica gel column chromatography (ethyl acetate/hexane) to give the title compound (13.0 g).

$^1$H NMR (500 MHz, CDCl$_3$) δ 3.98 (3H, s), 4.61 (2H, s), 6.86 (1H, d, J=2.44 Hz), 7.41 (1H, d, J=2.14 Hz), 7.75 (1H, dd, J=8.09, 2.29 Hz), 7.91 (1H, d, J=8.24 Hz), 8.60 (1H, d, J=2.14 Hz).

D) methyl 7-((6-(1-methyl-1H-pyrazol-3-yl)pyridin-3-yl)methyl)furo[3,2-b]pyridine-5-carboxylate The title compound was obtained by a method similar to that in step F of Example 1.

MS: [M+H]$^+$ 349.1.

E) methyl 7-((6-(1-methyl-1H-pyrazol-3-yl)pyridin-3-yl)methyl)-2,3-dihydrofuro[3,2-b]pyridine-5-carboxylate The title compound was obtained by a method similar to that in step G of Example 1.

MS: [M+H]$^+$ 351.1.

F) 7-((6-(1-methyl-1H-pyrazol-3-yl)pyridin-3-yl)methyl)-2,3-dihydrofuro[3,2-b]pyridine-5-carboxylic acid The title compound was obtained by a method similar to that in step H of Example 1.

MS: [M+H]$^+$ 337.1.

G) 1,5-anhydro-2,3-dideoxy-3-(((7-((6-(1-methyl-1H-pyrazol-3-yl)pyridin-3-yl)methyl)-2,3-dihydrofuro[3,2-b]pyridin-5-yl)carbonyl)amino)-L-threo-pentitol The title compound was obtained by a method similar to that in step I of Example 1.

Example 31

1,5-anhydro-2,3-dideoxy-3-(((7-(4-(1-methyl-1H-1,2,3-triazol-4-yl)benzyl)-2,3-dihydrofuro[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-1,2,3-triazol-4-yl)benzyl)-2,3-dihydrofuro[3,2-b]pyridine-5-carboxamide

A) methyl 7-(4-(1-methyl-1H-1,2,3-triazol-4-yl)benzyl)furo[3,2-b]pyridine-5-carboxylate A mixture of methyl 7-(4-(1-methyl-1H-1,2,3-triazol-4-yl)benzyl)furo[3,2-b]pyridine-5-carboxylate (1.92 g), 10% palladium-carbon (NX type, 50% wet with water, 400 mg) and MeOH (400 mL) was stirred under a hydrogen atmosphere of 5 MPa at 50° C. for 3 hr. The catalyst was filtered off, and the filtrate was concentrated under reduced pressure. A mixture of the residue, 10% palladium-carbon (NX type, 50% wet with water, 400 mg) and MeOH (400 mL) was stirred under a hydrogen atmosphere of 5 MPa at 50° C. for 2 hr. The catalyst was filtered off, and the filtrate was concentrated to give the title compound (1.90 g)

MS: [M+H]$^+$ 351.2.

B) 7-(4-(1-methyl-1H-1,2,3-triazol-4-yl)benzyl)-2,3-dihydrofuro[3,2-b]pyridine-5-carboxylic acid To a mixture of methyl 7-(4-(1-methyl-1H-1,2,3-triazol-4-yl)benzyl)-2,3-dihydrofuro[3,2-b]pyridine-5-carboxylate (2.72 g), MeOH (27 mL) and THF (13 mL) was added 2 M aqueous sodium hydroxide solution (23.29 mL) at room temperature. After stirring at room temperature overnight, 1 M hydrochloric acid (55 mL) was added, and the precipitated solid was collected by filtration to give the title compound (2.31 g).

MS: [M+H]$^+$ 337.2.

C) 1,5-anhydro-2,3-dideoxy-3-(((7-(4-(1-methyl-1H-1,2,3-triazol-4-yl)benzyl)-2,3-dihydrofuro[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-1,2,3-triazol-4-yl)benzyl)-2,3-dihydrofuro[3,2-b]pyridine-5-carboxamide To a mixture of 7-(4-(1-methyl-1H-1,2,3-triazol-4-yl)benzyl)-2,3-dihydrofuro[3,2-b]pyridine-5-carboxylic acid (350 mg), (3R,4S)-4-aminotetrahydro-2H-pyran-3-ol hydrochloride (192 mg), WSC·HCl (299 mg), HOBt·H$_2$O (191 mg) and DMF (7.0 mL) was added TEA (0.653 mL) at room temperature. After stirring at room temperature overnight, water was added to the reaction mixture. The precipitated solid was collected by filtration and washed with water. The solid was recrystallized from MEK/heptane to give the title compound (277 mg).

$^1$H NMR (300 MHz, DMSO-d$_6$) δ 1.49-1.69 (1H, m), 1.75-1.87 (1H, m), 3.00 (1H, t, J=10.4 Hz), 3.34-3.40 (3H, m), 3.54 (1H, tt, J=9.8, 5.1 Hz), 3.67-3.85 (3H, m), 3.95 (2H, s), 4.08 (3H, s), 4.76 (2H, t, J=8.9 Hz), 4.92 (1H, d, J=5.7 Hz), 7.31 (2H, d, J=8.3 Hz), 7.67 (1H, s), 7.76 (2H, d, J=8.3 Hz), 8.26 (1H, d, J=8.3 Hz), 8.46 (1H, s).

Example 33

N-((1S,2S)-2-hydroxycyclohexyl)-7-((6-(1-methyl-1H-1,2,3-triazol-4-yl)pyridin-3-yl)methyl)furo[3,2-b]pyridine-5-carboxamide

A) methyl 7-((6-(1-methyl-1H-1,2,3-triazol-4-yl)pyridin-3-yl)methyl)furo[3,2-b]pyridine-5-carboxylate The title compound was obtained by a method similar to that in step F of Example 1.

MS: [M+H]$^+$ 350.1.

B) 7-((6-(1-methyl-1H-1,2,3-triazol-4-yl)pyridin-3-yl)methyl)furo[3,2-b]pyridine-5-carboxylic acid The title compound was obtained by a method similar to that in step H of Example 1.

MS: [M+H]$^+$ 336.1.

C) N-((1S,2S)-2-hydroxycyclohexyl)-7-((6-(1-methyl-1H-1,2,3-triazol-4-yl)pyridin-3-yl)methyl)furo[3,2-b]pyridine-5-carboxamide The title compound was obtained by a method similar to that in step I of Example 1.
$^1$H NMR (300 MHz, CDCl$_3$) δ 1.18-1.51 (4H, m), 1.78 (2H, d, J=7.9 Hz), 2.01-2.23 (2H, m), 3.44-3.59 (2H, m), 3.85 (1H, brs.), 4.15 (3H, s), 4.31 (2H, s), 6.99 (1H, d, J=2.3 Hz), 7.67 (1H, dd, J=8.1, 2.1 Hz), 7.93 (1H, d, J=2.3 Hz), 8.01-8.13 (4H, m), 8.56 (1H, d, J=1.9 Hz).

Example 35

N-((1S,2S)-2-hydroxycyclohexyl)-7-((6-(1-methyl-1H-pyrazol-4-yl)pyridin-3-yl)methyl)furo[3,2-b]pyridine-5-carboxamide A) methyl 7-((6-(1-methyl-1H-pyrazol-4-yl)pyridin-3-yl)methyl)furo[3,2-b]pyridine-5-carboxylate To a mixture of methyl 7-(4,4,5,5-tetramethyl-1,3,2-dioxaborolan-2-yl)furo[3,2-b]pyridine-5-carboxylate (800 mg), 5-(chloromethyl)-2-(1-methyl-1H-pyrazol-4-yl)pyridine (603 mg), sodium carbonate (559 mg), DME (13 mL) and water (4.0 mL) was added PdCl$_2$(dppf) (97 mg) at room temperature, and the mixture was stirred under an argon atmosphere at 80° C. for 1 hr. To the mixture was added water, and the mixture was extracted with ethyl acetate. The organic layer was washed with water and saturated brine and dried over anhydrous sodium sulfate, and the solvent was evaporated under reduced pressure. The residue was purified by silica gel column chromatography (NH, ethyl acetate/hexane) to give the title compound (543.6 mg).
MS: [M+H]$^+$ 349.1.

B) 7-((6-(1-methyl-1H-pyrazol-4-yl)pyridin-3-yl)methyl)furo[3,2-b]pyridine-5-carboxylic acid To a mixture of methyl 7-((6-(1-methyl-1H-pyrazol-4-yl)pyridin-3-yl)methyl)furo[3,2-b]pyridine-5-carboxylate (150 mg), MeOH (3.0 mL) and THF (1.0 mL) was added 2 M aqueous sodium hydroxide solution (1.0 mL) at room temperature. After stirring at room temperature for 19 hr, the solvent was evaporated under reduced pressure. To the residue was added water (6.0 mL), and the mixture was neutralized with 1 M hydrochloric acid (2.0 mL). The mixture was stirred at room temperature for 3 hr, and the precipitated solid was collected by filtration to give the title compound (143 mg).
MS: [M+H]$^+$ 335.1.

C) N-((1S,2S)-2-hydroxycyclohexyl)-7-((6-(1-methyl-1H-pyrazol-4-yl)pyridin-3-yl)methyl)furo[3,2-b]pyridine-5-carboxamide The title compound was obtained by a method similar to that in step I of Example 1.

Example 36

1,5-anhydro-2,3-dideoxy-3-(((7-((6-(1-methyl-1H-pyrazol-4-yl)pyridin-3-yl)methyl)furo[3,2-b]pyridin-5-yl)carbonyl)amino)-L-threo-pentitol (synonym) N-((3R,4S)-3-hydroxytetrahydro-2H-pyran-4-yl)-7-((6-(1-methyl-1H-pyrazol-4-yl)pyridin-3-yl)methyl)furo[3,2-b]pyridine-5-carboxamide To a mixture of 7-((6-(1-methyl-1H-pyrazol-4-yl)pyridin-3-yl)methyl)furo[3,2-b]pyridine-5-carboxylic acid (50 mg), (3R,4S)-4-aminotetrahydro-2H-pyran-3-ol hydrochloride (27.6 mg), WSC·HCl (43 mg), HOBt·H$_2$O (27.5 mg) and DMF (1.0 mL) was added TEA (0.073 mL), and the mixture was stirred at room temperature for 22 hr. To the mixture was added ethyl acetate. The mixture was washed with water and saturated brine and dried over anhydrous sodium sulfate, and the solvent was evaporated under reduced pressure. The precipitate was washed with IPE and dried under reduced pressure to give the title compound (32.5 mg).
$^1$H NMR (300 MHz, CDCl$_3$) δ 1.74-1.92 (1H, m), 2.06 (1H, s), 3.23 (1H, dd, J=11.3, 9.8 Hz), 3.42-3.53 (1H, m), 3.65 (1H, td, J=9.1, 4.2 Hz), 3.91-4.17 (6H, m), 4.25-4.32 (3H, m), 6.99 (1H, d, J=2.6 Hz), 7.37 (1H, d, J=8.7 Hz), 7.55 (1H, dd, J=8.1, 2.5 Hz), 7.89 (2H, d, J=6.8 Hz), 7.94 (1H, d, J=2.3 Hz), 8.07 (1H, s), 8.14 (1H, d, J=7.2 Hz), 8.54 (1H, d, J=2.6 Hz).

Example 37

1,5-anhydro-2,3-dideoxy-3-(((7-((6-methoxypyridin-3-yl)methyl)furo[3,2-b]pyridin-5-yl)carbonyl)amino)-L-threo-pentitol A) 7-((6-methoxypyridin-3-yl)methyl)furo[3,2-b]pyridine-5-carboxylic acid The title compound was obtained by a method similar to that in step H of Example 1.
MS: [M+H]$^+$ 285.1.

B) 1,5-anhydro-2,3-dideoxy-3-(((7-((6-methoxypyridin-3-yl)methyl)furo[3,2-b]pyridin-5-yl)carbonyl)amino)-L-threo-pentitol The title compound was obtained by a method similar to that in step I of Example 1.

Example 38

1,5-anhydro-2,3-dideoxy-3-(((7-((6-oxo-1,6-dihydropyridin-3-yl)methyl)furo[3,2-b]pyridin-5-yl)carbonyl)amino)-L-threo-pentitol To a mixture of 1,5-anhydro-2,3-dideoxy-3-(((7-((6-methoxypyridin-3-yl)methyl)furo[3,2-b]pyridin-5-yl)carbonyl)amino)-L-threo-pentitol (115.8 mg) and acetonitrile (3.0 mL) were added sodium iodide (91 mg) and trimethylchlorosilane (0.116 mL) at room temperature. The mixture was stirred at 80° C. for 1.5 hr and concentrated under reduced pressure. To the residue was added water, and the precipitated solid was collected by filtration. The solid was washed with water and dried to give the title compound (109 mg).

Example 39

1,5-anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol A) methyl 7-(hydroxy(6-(1-methyl-1H-pyrazol-4-yl)pyridin-3-yl)methyl)furo[3,2-b]pyridine-5-carboxylate To a mixture of methyl 7-((6-(1-methyl-1H-pyrazol-4-yl)pyridin-3-yl)methyl)furo[3,2-b]pyridine-5-carboxylate (346.8 mg) and benzotrifluoride (7.0 mL) were added NBS (177 mg) and AIBN (32.7 mg) at room temperature. Under a nitrogen atmosphere, the reaction mixture was stirred under irradiation with a 60 W lamp at 80° C. for 1 hr. The reaction mixture was concentrated under reduced pressure, acetone (6.0 mL) and water (3.0 mL) were added to the residue, and the mixture was stirred at 50° C. for 5 hr. After ethyl acetate was added to the mixture, the mixture was added to water, and the mixture was extracted with ethyl acetate. The organic layer was washed with water and saturated brine, dried over anhydrous sodium sulfate, and concentrated under reduced pressure. The residue was purified by silica gel column chromatography (NH, MeOH/ethyl acetate) to give the title compound (65.8 mg).
MS: [M+H]$^+$ 365.1.

B) methyl 7-(fluoro(6-(1-methyl-1H-pyrazol-4-yl)pyridin-3-yl)methyl)furo[3,2-b]pyridine-5-carboxylate To a mixture of methyl 7-(hydroxy(6-(1-methyl-1H-pyrazol-4-yl)pyridin-3-yl)methyl)furo[3,2-b]pyridine-5-carboxylate (65 mg) and THF (5.0 mL) was added DAST (0.03 mL) at 0° C., and the mixture was stirred at room temperature for 0.5 hr and then at 60° C. for 0.5 hr. To the mixture was added DAST (0.03 mL) at 60° C., and mixture was stirred at the same temperature for 10 min. To the mixture was added ethyl acetate, and the mixture was added to saturated aqueous sodium hydrogen carbonate. The organic layer was washed with water and saturated brine and dried over anhydrous sodium sulfate, and the solvent was evaporated under reduced pressure. The residue was purified by silica gel column chromatography (NH, ethyl acetate/hexane) to give the title compound (22.7 mg).
MS: [M+H]$^+$ 367.1.

C) 1,5-anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol The title compound was obtained by a method similar to that in steps H and I of Example 1.

Example 40

1,5-anhydro-2,3-dideoxy-3-(((7-(4-(1-methyl-1H-pyrazol-4-yl)benzyl)furo[3,2-b]pyridin-5-yl)carbonyl)amino)-L-threo-pentitol A) methyl 7-(4-(1-methyl-1H-pyrazol-4-yl)benzyl)furo[3,2-b]pyridine-5-carboxylate To a mixture of methyl 7-(4,4,5,5-tetramethyl-1,3,2-dioxaborolan-2-yl)furo[3,2-b]pyridine-5-carboxylate (1000 mg), 4-(4-(chloromethyl)phenyl)-1-methyl-1H-pyrazole (750 mg), potassium carbonate (699 mg), DME (15 mL) and water (5.0 mL) was added PdCl$_2$(dppf) (121 mg) at room temperature. The mixture was stirred under an argon atmosphere at 80° C. for 1 hr. The mixture was diluted with ethyl acetate at room temperature and added to water, and the mixture was extracted with ethyl acetate. The organic layer was washed with water and saturated brine, dried over anhydrous sodium sulfate, and concentrated under reduced pressure. The residue was purified by silica gel column chromatography (NH, ethyl acetate/hexane) to give the title compound (729.0 mg).
MS: [M+H]$^+$ 348.2.

B) 7-(4-(1-methyl-1H-pyrazol-4-yl)benzyl)furo[3,2-b]pyridine-5-carboxylic acid

To a mixture of methyl 7-(4-(1-methyl-1H-pyrazol-4-yl)benzyl)furo[3,2-b]pyridine-5-carboxylate (294.2 mg), MeOH (6.0 mL) and THF (3.0 mL) was added 2 M aqueous sodium hydroxide solution (2.0 mL) at room temperature. The mixture was stirred at room temperature for 3 hr, and the solvent was evaporated under reduced pressure. To the residue was added water (8.0 mL), and the mixture was neutralized with 1 M hydrochloric acid (4.0 mL). The precipitated solid was collected by filtration, washed with water, and dried under reduced pressure to give the title compound (306 mg).
MS: [M+H]$^+$ 334.1.

C) 1,5-anhydro-2,3-dideoxy-3-(((7-(4-(1-methyl-1H-pyrazol-4-yl)benzyl)furo[3,2-b]pyridin-5-yl)carbonyl)amino)-L-threo-pentitol The title compound was obtained by a method similar to that in step I of Example 1.

Example 42

N-(trans-4,4-difluoro-2-hydroxycyclohexyl)-7-(4-(1H-pyrazol-1-yl)benzyl)-2,3-dihydrofuro[3,2-b]pyridine-5-carboxamide The title compound was obtained by a method similar to that in step I of Example 1.

Example 43

1,5-anhydro-2,3-dideoxy-3-(((7-(4-(6-methylpyridazin-4-yl)benzyl)furo[3,2-b]pyridin-5-yl)carbonyl)amino)-L-threo-pentitol A) methyl 7-(4-(6-methylpyridazin-4-yl)benzyl)furo[3,2-b]pyridine-5-carboxylate The title compound was obtained by a method similar to that in step F of Example 1.
MS: [M+H]$^+$ 360.1.

B) 7-(4-(6-methylpyridazin-4-yl)benzyl)furo[3,2-b]pyridine-5-carboxylic acid

The title compound was obtained by a method similar to that in step H of Example 1.
$^1$H NMR (300 MHz, DMSO-d$_6$) 52.66 (3H, s), 4.42 (2H, s), 7.26 (1H, d, J=2.3 Hz), 7.52 (2H, d, J=8.3 Hz), 7.81-7.91 (3H, m), 7.94 (1H, s), 8.48 (1H, d, J=2.6 Hz), 9.44 (1H, d, J=2.3 Hz), 13.12 (1H, brs.).

C) 1,5-anhydro-2,3-dideoxy-3-(((7-(4-(6-methylpyridazin-4-yl)benzyl)furo[3,2-b]pyridin-5-yl)carbonyl)amino)-L-threo-pentitol The title compound was obtained by a method similar to that in step I of Example 1.

Example 44

1,5-anhydro-2,3-dideoxy-3-(((7-(4-(1-methyl-1H-pyrazol-4-yl)benzyl)-2,3-dihydrofuro[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-pyrazol-4-yl)benzyl)-2,3-dihydrofuro[3,2-b]pyridine-5-carboxamide

A) methyl 7-(4-(1-methyl-1H-pyrazol-4-yl)benzyl)-2,3-dihydrofuro[3,2-b]pyridine-5-carboxylate A mixture of methyl 7-(4-(1-methyl-1H-pyrazol-4-yl)benzyl)furo[3,2-b]pyridine-5-carboxylate (466 mg), 10% palladium-carbon (50% wet with water, 93 mg) and MeOH (30 ml) was stirred under a hydrogen atmosphere of 5 MPa at 50° C. for 6 hr. The catalyst was filtered off, and the filtrate was concentrated under reduced pressure. The residue was purified by silica gel column chromatography (NH, ethyl acetate/hexane) to give the title compound (389.1 mg).
MS: [M+H]$^+$ 350.2.

B) 7-(4-(1-methyl-1H-pyrazol-4-yl)benzyl)-2,3-dihydrofuro[3,2-b]pyridine-5-carboxylic acid To a mixture of methyl 7-(4-(1-methyl-1H-pyrazol-4-yl)benzyl)-2,3-dihydrofuro[3,2-b]pyridine-5-carboxylate (389 mg), MeOH (8.0 mL) and THF (3.0 mL) was added 2 M aqueous sodium hydroxide solution (3.0 mL) at room temperature. After stirring at room temperature for 4 hr, the mixture was concentrated under reduced pressure. To the residue was added water (12 mL), and the mixture was neutralized with 1 M hydrochloric acid (6.0 mL). The precipitated solid was collected by filtration, washed with water, and dried under reduced pressure to give the title compound (364 mg).
MS: [M+H]$^+$ 336.1.

C) 1,5-anhydro-2,3-dideoxy-3-(((7-(4-(1-methyl-1H-pyrazol-4-yl)benzyl)-2,3-dihydrofuro[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-pyrazol-4-yl)benzyl)-2,3-dihydrofuro[3,2-b]pyridine-5-carboxamide To a mixture of 7-(4-(1-methyl-1H-pyrazol-4-yl)benzyl)-2,3-dihydrofuro[3,2-b]pyridine-5-carboxylic acid (55.9 mg), (3R,4S)-4-aminotetrahydro-2H-pyran-3-ol hydrochloride (51.2 mg), WSC·HCl (128 mg), HOBt·H$_2$O (51.1 mg) and DMF (1.0 mL) was added TEA (0.163 mL) at room temperature. After stirring at room temperature for 3 days, water was added to the mixture. The precipitated solid was collected by filtration, washed with water, and dried under reduced pressure to give the title compound (67.7 mg).
$^1$H NMR (300 MHz, CDCl$_3$) δ 1.70-1.87 (1H, m), 1.93-2.08 (1H, m), 3.20 (1H, dd, J=11.3, 9.8 Hz), 3.33 (2H, t, J=8.9 Hz), 3.45 (1H, td, J=11.9, 2.3 Hz), 3.52-3.69 (1H, m), 3.81-4.03 (7H, m), 4.07 (1H, dd, J=11.3, 4.9 Hz), 4.53 (1H, d, J=3.0 Hz), 4.76 (2H, t, J=9.1 Hz), 7.22 (2H, d, J=7.9 Hz), 7.38 (2H, d, J=8.3 Hz), 7.57 (1H, s), 7.71 (1H, d, J=0.8 Hz), 7.85 (1H, s), 7.90 (1H, d, J=5.7 Hz).

Example 45

N-(trans-4,4-difluoro-2-hydroxycyclohexyl)-7-(4-(1H-pyrazol-1-yl)benzyl)-2,3-dihydrofuro[3,2-b]pyridine-5-carboxamide (Optical Isomer: Retention Time Short)

N-(trans-4,4-Difluoro-2-hydroxycyclohexyl)-7-(4-(1H-pyrazol-1-yl)benzyl)-2,3-dihydrofuro[3,2-b]pyridine-5-carboxamide (114 mg) produced in Example 42 was optically resolved by HPLC (CHIRALPAK IC, 50 mmID×500 mmL, mobile phase: hexane/EtOH=400/600), and the material having a shorter retention time (tR1) was triturated with IPE to give the title compound (49.1 mg).

Example 46

N-(trans-4,4-difluoro-2-hydroxycyclohexyl)-7-(4-(1H-pyrazol-1-yl)benzyl)-2,3-dihydrofuro[3,2-b]pyridine-5-carboxamide (Optical Isomer: Retention Time Long)

N-(trans-4,4-Difluoro-2-hydroxycyclohexyl)-7-(4-(1H-pyrazol-1-yl)benzyl)-2,3-dihydrofuro[3,2-b]pyridine-5-carboxamide (114 mg) produced in Example 42 was optically resolved by HPLC (CHIRALPAK IC, 50 mmID×500 mmL, mobile phase: hexane/EtOH=400/600), and the material having a longer retention time (tR2) was triturated with IPE to give the title compound (52.0 mg).

Example 49

1,5-anhydro-2,3-dideoxy-3-(((7-(4-(2-methylpyrimidin-4-yl)benzyl)furo[3,2-b]pyridin-5-yl)carbonyl)amino)-L-threo-pentitol

A) (4-(2-methylpyrimidin-4-yl)phenyl)methanol

The title compound was obtained from (4-(hydroxymethyl)phenyl)boronic acid and 4-chloro-2-methylpyrimidine by a method similar to that in step F of Example 1.
MS: [M+H]$^+$ 201.1.

B) 4-(4-(chloromethyl)phenyl)-2-methylpyrimidine

The title compound was obtained by a method similar to that in step B of Example 14.
MS: [M+H]$^+$ 219.1.

C) methyl 7-(4-(2-methylpyrimidin-4-yl)benzyl)furo[3,2-b]pyridine-5-carboxylate The title compound was obtained by a method similar to that in step F of Example 1.
MS: [M+H]$^+$ 360.2.

D) 7-(4-(2-methylpyrimidin-4-yl)benzyl)furo[3,2-b]pyridine-5-carboxylic acid The title compound was obtained by a method similar to that in step H of Example 1.
MS: [M+H]$^+$ 346.2.

E) 1,5-anhydro-2,3-dideoxy-3-(((7-(4-(2-methylpyrimidin-4-yl)benzyl)furo[3,2-b]pyridin-5-yl)carbonyl)amino)-L-threo-pentitol The title compound was obtained by a method similar to that in step I of Example 1.

Example 51

1,5-anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol (Stereoisomer: Retention Time Short)

1,5-Anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol (21.1 mg) produced in Example 39 was resolved by HPLC (CHIRALCEL OJ, 50 mmID×500 mmL, mobile phase: hexane/EtOH=150/850), and the material having a shorter retention time (tR1) was triturated with IPE to give the title compound (3.1 mg).

Example 52

1,5-anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol (Stereoisomer: Retention Time Long)

1,5-Anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol (21.1 mg) produced in Example 39 was resolved by HPLC (CHIRALCEL OJ, 50 mmID×500 mmL, mobile phase: hexane/EtOH=150/850), and the material having a longer retention time (tR2) was triturated with IPE to give the title compound (3.7 mg).

Example 53

1,5-anhydro-2,3-dideoxy-3-(((7-(fluoro(4-(1-methyl-1H-1,2,3-triazol-4-yl)phenyl)methyl)furo[3,2-b]pyridin-5-yl)carbonyl)amino)-L-threo-pentitol A) methyl 7-(hydroxy(4-(1-methyl-1H-1,2,3-triazol-4-yl)phenyl)methyl)furo[3,2-b]pyridine-5-carboxylate To a mixture of methyl 7-(4-(1-methyl-1H-1,2,3-triazol-4-yl)benzyl)furo[3,2-b]pyridine-5-carboxylate (100 mg) and trifluorotoluene (3.0 mL) were added NBS (53.6 mg) and AIBN (4.71 mg) at room temperature. The mixture was stirred under a nitrogen atmosphere at 80° C. for 5 hr. After concentration under reduced pressure, acetone (3.0 mL) and water (10 mL) were added to the residue, and the mixture was stirred at 50° C. for 16 hr. The mixture was added to water at room temperature, and the mixture was extracted with ethyl acetate. The organic layer was washed with saturated brine, dried over anhydrous sodium sulfate, and concentrated under reduced pressure. The residue was purified by silica gel column chromatography (NH, ethyl acetate/hexane) to give the title compound (55.1 mg).
MS: [M+H]⁺ 365.2.

B) methyl 7-(fluoro(4-(1-methyl-1H-1,2,3-triazol-4-yl)phenyl)methyl)furo[3,2-b]pyridine-5-carboxylate To a mixture of methyl 7-(hydroxy(4-(1-methyl-1H-1,2,3-triazol-4-yl)phenyl)methyl)furo[3,2-b]pyridine-5-carboxylate (212.6 mg) and dehydrated THF (12 mL) was added DAST (0.154 mL) at room temperature. After stirring the mixture at room temperature for 15 min, the mixture was added to saturated aqueous sodium hydrogen carbonate, and the mixture was extracted with ethyl acetate. The organic layer was washed with water and saturated brine, dried over anhydrous sodium sulfate, and concentrated under reduced pressure. The precipitate was collected by filtration, washed with IPE, and dried under reduced pressure to give the title compound (185 mg).
MS: [M+H]⁺ 367.2.

C) 7-(fluoro (4-(1-methyl-1H-1,2,3-triazol-4-yl) phenyl)methyl)furo[3,2-b]pyridine-5-carboxylic acid To a mixture of methyl 7-(fluoro(4-(1-methyl-1H-1,2,3-triazol-4-yl)phenyl)methyl)furo[3,2-b]pyridine-5-carboxylate (236 mg), MeOH (5.0 mL) and THF (3.0 mL) was added 2 M aqueous sodium hydroxide solution (2.0 mL) at room temperature. The mixture was stirred at room temperature for 1 hr and concentrated under reduced pressure. To the residue was added water (6.0 mL), and the mixture was neutralized with 1 M hydrochloric acid (4.0 mL). The precipitated solid was collected by filtration, washed with water, and dried under reduced pressure to give the title compound (219 mg).
MS: [M+H]⁺ 353.2.

D) 1,5-anhydro-2,3-dideoxy-3-(((7-(fluoro(4-(1-methyl-1H-1,2,3-triazol-4-yl)phenyl)methyl)furo[3,2-b]pyridin-5-yl)carbonyl)amino)-L-threo-pentitol To a mixture of 7-(fluoro(4-(1-methyl-1H-1,2,3-triazol-4-yl)phenyl)methyl)furo[3,2-b]pyridine-5-carboxylic acid (160 mg), (3R,4S)-4-aminotetrahydro-2H-pyran-3-ol (91 mg), WSC·HCl (174 mg), HOBt·H₂O (90 mg) and DMF (3.0 mL) was added TEA (0.253 mL) at room temperature. The mixture was stirred at room temperature for 18 hr. The reaction mixture was added to water, and the mixture was extracted with ethyl acetate. The organic layer was washed with water and saturated brine, dried over anhydrous sodium sulfate, and concentrated under reduced pressure. To the residue was added IPE, and the precipitated solid was collected by filtration. The solid was washed with IPE and dried under reduced pressure to give the title compound (200.6 mg).

Example 54

7-(fluoro(4-(1-methyl-1H-1,2,3-triazol-4-yl)phenyl)methyl)-N-((1S,2S)-2-hydroxycyclohexyl)furo[3,2-b]pyridine-5-carboxamide The title compound was obtained by a method similar to that in step I of Example 1.

Example 55

1,5-anhydro-2,3-dideoxy-3-(((7-(fluoro(4-(1-methyl-1H-1,2,3-triazol-4-yl)phenyl)methyl)furo[3,2-b]pyridin-5-yl)carbonyl)amino)-L-threo-pentitol (Stereoisomer: Retention Time Short)

(synonym) 7-(fluoro(4-(1-methyl-1H-1,2,3-triazol-4-yl)phenyl)methyl)-N-((3R,4S)-3-hydroxytetrahydro-2H-pyran-4-yl)furo[3,2-b]pyridine-5-carboxamide (Stereoisomer: Retention Time Short)

1,5-Anhydro-2,3-dideoxy-3-(((7-(fluoro(4-(1-methyl-1H-1,2,3-triazol-4-yl)phenyl)methyl)furo[3,2-b]pyridin-5- yl)carbonyl)amino)-L-threo-pentitol (194.6 mg) produced in Example 53 was resolved by HPLC (CHIRALPAK IA, 50 mmID×500 mmL, mobile phase: EtOH), and the material having a shorter retention time (tR1) was triturated with IPE to give the title compound (70 mg).

$^1$H NMR (300 MHz, CDCl$_3$) δ 1.76-1.92 (1H, m), 2.03-2.14 (1H, m), 3.25 (1H, dd, J=11.3, 9.9 Hz), 3.50 (1H, td, J=12.0, 2.5 Hz), 3.57-3.75 (1H, m), 3.95-4.06 (2H, m), 4.06-4.18 (4H, m), 4.23 (1H, dd, J=3.5, 0.6 Hz), 6.84-7.05 (2H, m), 7.53 (2H, d, J=7.4 Hz), 7.75 (1H, s), 7.84 (2H, d, J=8.0 Hz), 7.94 (1H, d, J=2.3 Hz), 8.14 (1H, d, J=5.9 Hz), 8.38 (1H, d, J=1.8 Hz).

Example 56

1,5-anhydro-2,3-dideoxy-3-(((7-(fluoro(4-(1-methyl-1H-1,2,3-triazol-4-yl)phenyl)methyl)furo[3,2-b]pyridin-5-yl)carbonyl)amino)-L-threo-pentitol (Stereoisomer: Retention Time Long)

1,5-Anhydro-2,3-dideoxy-3-(((7-(fluoro(4-(1-methyl-1H-1,2,3-triazol-4-yl)phenyl)methyl)furo[3,2-b]pyridin-5-yl)carbonyl)amino)-L-threo-pentitol (194.6 mg) produced in Example 53 was resolved by HPLC (CHIRALPAK IA, 50 mmID×500 mmL, mobile phase: EtOH), and the material having a longer retention time (tR2) was triturated with IPE to give the title compound (80.2 mg).

Example 57

7-(fluoro(4-(1-methyl-1H-1,2,3-triazol-4-yl)phenyl)methyl)-N-((1S,2S)-2-hydroxycyclohexyl)furo[3,2-b]pyridine-5-carboxamide (Stereoisomer: Retention Time Short)

7-(Fluoro(4-(1-methyl-1H-1,2,3-triazol-4-yl)phenyl)methyl)-N-((1S,2S)-2-hydroxycyclohexyl)furo[3,2-b]pyridine-5-carboxamide (63 mg) produced in Example 54 was resolved by HPLC (CHIRALPAK AD, 50 mmID×500 mmL, mobile phase: EtOH), and the material having a shorter retention time (tR1) was triturated with IPE to give the title compound (20.9 mg).

Example 58

7-(fluoro(4-(1-methyl-1H-1,2,3-triazol-4-yl)phenyl)methyl)-N-((1S,2S)-2-hydroxycyclohexyl)furo[3,2-b]pyridine-5-carboxamide (Stereoisomer: Retention Time Long)

7-(Fluoro(4-(1-methyl-1H-1,2,3-triazol-4-yl)phenyl)methyl)-N-((1S,2S)-2-hydroxycyclohexyl)furo[3,2-b]pyridine-5-carboxamide (63 mg) produced in Example 54 was resolved by HPLC (CHIRALPAK AD, 50 mmID×500 mmL, mobile phase: EtOH), and the material having a longer retention time (tR2) was triturated with IPE to give the title compound (23.0 mg).

Example 60

1,5-anhydro-2,3-dideoxy-3-(((7-((6-(1-methyl-1H-pyrazol-4-yl)pyridin-3-yl)methyl)-2,3-dihydrofuro[3,2-b]pyridin-5-yl)carbonyl)amino)-L-threo-pentitol A) methyl 7-((6-(1-methyl-1H-pyrazol-4-yl)pyridin-3-yl)methyl)-2,3-dihydrofuro[3,2-b]pyridine-5-carboxylate The title compound was obtained by a method similar to that in step G of Example 1.
MS: [M+H]$^+$ 351.2.

B) 7-((6-(1-methyl-1H-pyrazol-4-yl)pyridin-3-yl)methyl)-2,3-dihydrofuro[3,2-b]pyridine-5-carboxylic acid The title compound was obtained by a method similar to that in step H of Example 1.
MS: [M+H]$^+$ 337.1.

C) 1,5-anhydro-2,3-dideoxy-3-(((7-((6-(1-methyl-1H-pyrazol-4-yl)pyridin-3-yl)methyl)-2,3-dihydrofuro[3,2-b]pyridin-5-yl)carbonyl)amino)-L-threo-pentitol The title compound was obtained by a method similar to that in step I of Example 1.

Example 62

1,5-anhydro-2,3-dideoxy-3-(((7-(3-fluoro-4-(methylcarbamoyl)benzyl)furo[3,2-b]pyridin-5-yl)carbonyl)amino)-L-threo-pentitol A) methyl 7-(3-fluoro-4-(methylcarbamoyl)benzyl)furo[3,2-b]pyridine-5-carboxylate The title compound was obtained by a method similar to that in step F of Example 1.
MS: [M+H]$^+$ 343.2.

B) 7-(3-fluoro-4-(methylcarbamoyl)benzyl)furo[3,2-b]pyridine-5-carboxylic acid

The title compound was obtained by a method similar to that in step H of Example 1.
MS: [M+H]$^+$ 329.1.

C) 1,5-anhydro-2,3-dideoxy-3-(((7-(3-fluoro-4-(methylcarbamoyl)benzyl)furo[3,2-b]pyridin-5-yl)carbonyl)amino)-L-threo-pentitol The title compound was obtained by a method similar to that in step I of Example 1.

Example 63

1,5-anhydro-2,3-dideoxy-3-(((7-(3-fluoro-4-(methylcarbamoyl)benzyl)-2,3-dihydrofuro[3,2-b]pyridin-5-yl)carbonyl)amino)-L-threo-pentitol A) methyl 2,3-dihydrofuro[3,2-b]pyridine-5-carboxylate The title compound was obtained by a method similar to that in step G of Example 1.
$^1$H NMR (300 MHz, CDCl$_3$) δ 3.42 (2H, t, J=8.9 Hz), 3.98 (3H, s), 4.76 (2H, t, J=8.9 Hz), 7.07 (1H, d, J=8.7 Hz), 7.97 (1H, d, J=8.3 Hz).

B) methyl 7-(4,4,5,5-tetramethyl-1,3,2-dioxaborolan-2-yl)-2,3-dihydrofuro[3,2-b]pyridine-5-carboxylate The title compound was obtained by a method similar to that in step D of Example 20.
$^1$H NMR (300 MHz, DMSO-d$_6$) δ 1.29 (12H, s), 3.24-3.32 (2H, m), 3.83 (3H, s), 4.75 (2H, t, J=8.9 Hz), 7.98 (1H, s).

C) methyl 7-(3-fluoro-4-(methylcarbamoyl)benzyl)-2,3-dihydrofuro[3,2-b]pyridine-5-carboxylate The title compound was obtained by a method similar to that in step F of Example 1.
MS: [M+H]+ 345.2.

D) 7-(3-fluoro-4-(methylcarbamoyl)benzyl)-2,3-dihydrofuro[3,2-b]pyridine-5-carboxylic acid The title compound was obtained by a method similar to that in step H of Example 1.
MS: [M+H]+ 331.1.

E) 1,5-anhydro-2,3-dideoxy-3-(((7-(3-fluoro-4-(methylcarbamoyl)benzyl)-2,3-dihydrofuro[3,2-b]pyridin-5-yl)carbonyl)amino)-L-threo-pentitol The title compound was obtained by a method similar to that in step H of Example 20.
$^1$H NMR (300 MHz, DMSO-$d_6$) δ 1.51-1.68 (1H, m), 1.75-1.86 (1H, m), 2.75 (3H, d, J=4.5 Hz), 2.96-3.06 (1H, m), 3.32 (3H, s), 3.49-3.61 (1H, m), 3.70-3.83 (3H, m), 3.99 (2H, s), 4.75 (2H, t, J=8.9 Hz), 4.92 (1H, d, J=5.7 Hz), 7.10-7.20 (2H, m), 7.55 (1H, t, J=7.7 Hz), 7.68 (1H, s), 8.14-8.22 (1H, m), 8.26 (1H, d, J=8.3 Hz).

Example 64

1,5-anhydro-2,3-dideoxy-3-(((2-methyl-7-(4-(1-methyl-1H-1,2,3-triazol-4-yl)benzyl)furo[3,2-b]pyridin-5-yl)carbonyl)amino)-L-threo-pentitol A) methyl 7-chloro-2-iodofuro[3,2-b]pyridine-5-carboxylate To a solution of methyl 7-chloro-2-(trimethylsilyl)furo[3,2-b]pyridine-5-carboxylate (9.0 g) in acetonitrile (450 mL) were added N-iodosuccinimide (71.55 g) and potassium fluoride (7.38 g) at room temperature, and the mixture was stirred at 50° C. for 4 hr. The reaction mixture was concentrated under reduced pressure, an aqueous solution of sodium thiosulfate was added to the residue, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/petroleum ether) to give the title compound (8.0 g).
MS: [M+H]+ 338.05.

B) methyl 7-chloro-2-methylfuro[3,2-b]pyridine-5-carboxylate

A mixture of methyl 7-chloro-2-iodofuro[3,2-b]pyridine-5-carboxylate (8.00 g), methylboronic acid (2.84 g), tripotassium phosphate (15.1 g), tricyclohexylphosphine (1.99 g), palladium(II) acetate (1.06 g) and toluene (240 mL) was stirred under an argon atmosphere at 120° C. for 18 hr. After cooling the reaction mixture to room temperature, water was added, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/petroleum ether) to give the title compound (3.10 g).
MS: [M+H]+ 225.9.

C) methyl 2-methyl-7-(4,4,5,5-tetramethyl-1,3,2-dioxaborolan-2-yl)furo[3,2-b]pyridine-5-carboxylate To a mixture of bis(pinacolato)diboron (5.84 g), methyl 7-chloro-2-methylfuro[3,2-b]pyridine-5-carboxylate (2.60 g), 2-dicyclohexylphosphino-2',4',6'-triisopropyl-1,1'-biphenyl (0.550 g), potassium acetate (3.39 g) and 1,4-dioxane (78 mL) was added Pd$_2$(dba)$_3$ (0.528 g) at room temperature. The mixture was stirred under an argon atmosphere at 80° C. for 2 hr and cooled to room temperature. The reaction mixture was diluted with THF and heated at 60° C. The insoluble material was removed by celite filtration. The filtrate was concentrated, and the obtained solid was washed with pentane to give the title compound (2.60 g).
$^1$H NMR (400 MHz, DMSO-$d_6$) δ 1.36 (12H, s), 2.58 (3H, s), 3.90 (3H, s), 6.91 (1H, s), 8.13 (1H, s).

D) 2-methyl-7-(4-(1-methyl-1H-1,2,3-triazol-4-yl)benzyl)furo[3,2-b]pyridine-5-carboxylic acid A mixture of methyl 2-methyl-7-(4,4,5,5-tetramethyl-1,3,2-dioxaborolan-2-yl)furo[3,2-b]pyridine-5-carboxylate (428 mg), 4-(4-(chloromethyl)phenyl)-1-methyl-1H-1,2,3-triazole (278 mg), Pd(PPh$_3$)$_4$ (35 mg), potassium carbonate (372 mg), 1,4-dioxane (12 mL) and water (4.0 mL) was subjected to microwave irradiation at 110° C. for 1 hr. The solvent was concentrated under reduced pressure. The residue was washed with ethyl acetate, 1 M hydrochloric acid was added to adjust pH to 2, and the mixture was stirred. The precipitated solid was collected by filtration and purified by silica gel column chromatography (MeOH/dichloromethane) to give the title compound (200 mg).
MS: [M+H]+ 349.41.

E) 1,5-anhydro-2,3-dideoxy-3-(((2-methyl-7-(4-(1-methyl-1H-1,2,3-triazol-4-yl)benzyl)furo[3,2-b]pyridin-5-yl)carbonyl)amino)-L-threo-pentitol The title compound was obtained by a method similar to that in step I of Example 1.
$^1$H NMR (500 MHz, DMSO-$d_6$) δ 1.62-1.65 (1H, m), 1.81-1.84 (1H, m), 2.57 (3H, d, J=0.92 Hz), 3.02 (1H, t, J=10.5 Hz), 3.30-3.34 (1H, m), 3.57-3.61 (1H, m), 3.76-3.82 (3H, m), 4.07 (3H, s), 4.32 (2H, s), 4.95 (1H, d, J=5.80 Hz), 6.87 (1H, d, J=1.22 Hz), 7.38 (2H, d, J=8.24 Hz), 7.77-7.80 (3H, m), 8.47 (1H, s), 8.51 (1H, d, J=8.54 Hz).

Example 65

1,5-anhydro-2,3-dideoxy-3-(((7-(3-fluoro-4-(methylcarbamoyl)benzyl)-2-methylfuro[3,2-b]pyridin-5-yl)carbonyl)amino)-L-threo-pentitol A) 7-(3-fluoro-4-(methylcarbamoyl)benzyl)-2-methylfuro[3,2-b]pyridine-5-carboxylic acid The title compound was obtained by a method similar to that in step D of Example 64.
MS: [M+H]+ 343.33.

B) 1,5-anhydro-2,3-dideoxy-3-(((7-(3-fluoro-4-(methylcarbamoyl)benzyl)-2-methylfuro[3,2-b]pyridin-5-yl)carbonyl)amino)-L-threo-pentitol The title compound was obtained by a method similar to that in step I of Example 1.

$^1$H NMR (400 MHz, DMSO-$d_6$) δ 1.62-1.68 (1H, m), 1.76-1.84 (1H, m), 2.56 (3H, s), 2.75 (3H, d, J=4.40 Hz), 3.02 (1H, t, J=10.51 Hz), 3.34-3.35 (1H, m), 3.59 (1H, brs), 3.77-3.82 (3H, m), 4.35 (2H, s), 4.94 (1H, brs), 6.87 (1H, s), 7.19-7.28 (2H, m), 7.56 (1H, t, J=7.83 Hz), 7.79 (1H, s), 8.18 (1H, brs), 8.51 (1H, d, J=8.31 Hz).

Example 66

1,5-anhydro-2,3-dideoxy-3-(((2-methyl-7-(4-(1-methyl-1H-pyrazol-4-yl)benzyl)furo[3,2-b]pyridin-5-yl)carbonyl)amino)-L-threo-pentitol A) 2-methyl-7-(4-(1-methyl-1H-pyrazol-4-yl)benzyl)furo[3,2-b]pyridine-5-carboxylic acid The title compound was obtained by a method similar to that in step D of Example 64.
MS: [M+H]$^+$ 348.37.

B) 1,5-anhydro-2,3-dideoxy-3-(((2-methyl-7-(4-(1-methyl-1H-pyrazol-4-yl)benzyl)furo[3,2-b]pyridin-5-yl)carbonyl)amino)-L-threo-pentitol The title compound was obtained by a method similar to that in step I of Example 1.

$^1$H NMR (500 MHz, DMSO-$d_6$) δ 1.62-1.67 (1H, m), 1.81-1.84 (1H, m), 2.57 (3H, s), 3.02 (1H, t, J=10.53 Hz), 3.33-3.34 (1H, s), 3.55-3.61 (1H, m), 3.75-3.82 (3H, m), 3.84 (3H, s), 4.27 (2H, s), 4.94 (1H, d, J=5.80 Hz), 6.86 (1H, d, J=0.92 Hz), 7.29 (2H, d, J=8.24 Hz), 7.50 (2H, d, J=7.93 Hz), 7.78 (1H, s), 7.80 (1H, s), 8.07 (1H, s), 8.49 (1H, d, J=8.24 Hz).

Example 67

1,5-anhydro-2,3-dideoxy-3-(((2-methyl-7-(4-(1H-pyrazol-1-yl)benzyl)furo[3,2-b]pyridin-5-yl)carbonyl)amino)-L-threo-pentitol A) 2-methyl-7-(4-(1H-pyrazol-1-yl)benzyl)furo[3,2-b]pyridine-5-carboxylic acid The title compound was obtained by a method similar to that in step D of Example 64.
MS: [M+H]$^+$ 334.27.

B) 1,5-anhydro-2,3-dideoxy-3-(((2-methyl-7-(4-(1H-pyrazol-1-yl)benzyl)furo[3,2-b]pyridin-5-yl)carbonyl)amino)-L-threo-pentitol The title compound was obtained by a method similar to that in step I of Example 1.

$^1$H NMR (500 MHz, DMSO-$d_6$) δ 1.62-1.65 (1H, m), 1.81-1.84 (1H, m), 2.57 (3H, d, J=0.92 Hz), 3.02 (1H, t, J=10.53 Hz), 3.29-3.31 (1H, m), 3.57-3.62 (1H, m), 3.75-3.82 (3H, m), 4.34 (2H, s), 4.94 (1H, d, J=5.80 Hz), 6.52 (1H, dd, J=2.44, 1.83 Hz), 6.87 (1H, d, J=1.22 Hz), 7.43 (2H, d, J=9.0 Hz), 7.72 (1H, d, J=1.83 Hz), 7.77-7.80 (3H, m), 8.45 (1H, dd, J=2.44, 0.61 Hz), 8.51 (1H, d, J=8.54 Hz).

Example 68

1,5-anhydro-2,3-dideoxy-3-(((2-methyl-7-((6-(1-methyl-1H-1,2,3-triazol-4-yl)pyridin-3-yl)methyl)furo[3,2-b]pyridin-5-yl)carbonyl)amino)-L-threo-pentitol A) 2-methyl-7-((6-(1-methyl-1H-1,2,3-triazol-4-yl)pyridin-3-yl)methyl)furo[3,2-b]pyridine-5-carboxylic acid The title compound was obtained by a method similar to that in step D of Example 64.
MS: [M+H]$^+$ 350.35.

B) 1,5-anhydro-2,3-dideoxy-3-(((2-methyl-7-((6-(1-methyl-1H-1,2,3-triazol-4-yl)pyridin-3-yl)methyl)furo[3,2-b]pyridin-5-yl)carbonyl)amino)-L-threo-pentitol The title compound was obtained by a method similar to that in step I of Example 1.

$^1$H NMR (500 MHz, DMSO-$d_6$) δ 1.63-1.67 (1H, m), 1.81-1.84 (1H, m), 2.57 (3H, s), 3.02 (1H, t, J=10.38 Hz), 3.35-3.37 (1H, m), 3.57-3.62 (1H, m), 3.77-3.82 (3H, m), 4.10 (3H, s), 4.36 (2H, s), 4.94 (1H, d, J=5.80 Hz), 6.88 (1H, d, J=0.92 Hz), 7.80 (1H, dd, J=8.24, 2.14 Hz), 7.83 (1H, s), 7.97 (1H, d, J=7.93 Hz), 8.51-8.52 (2H, m), 8.62 (1H, d, J=1.83 Hz).

Example 74

1,5-anhydro-2,3-dideoxy-3-(((7-(4-(1-methyl-1H-imidazol-4-yl)benzyl)-2,3-dihydrofuro[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-imidazol-4-yl)benzyl)-2,3-dihydrofuro[3,2-b]pyridine-5-carboxamide A) (4-(1-methyl-1H-imidazol-4-yl)phenyl)methanol To a mixture of 4-bromo-1-methyl-1H-imidazole (25 g), (4-(hydroxymethyl)phenyl)boronic acid (47.2 g), DME (250 mL) and water (50 mL) were added cesium carbonate (100.93 g) and PdCl$_2$(dppf)·DCM (6.33 g) under an argon atmosphere at room temperature, and the mixture was stirred under an argon atmosphere at 120° C. for 6 hr. The reaction mixture was diluted with ethyl acetate, and the insoluble material was removed by celite filtration. The filtrate was washed with water and saturated brine, dried over anhydrous sodium sulfate, and concentrated under reduced pressure. The residue was purified by silica gel column chromatography (ethyl acetate) to give the title compound (18.0 g).
MS: [M+H]$^+$ 189.1.

B) 4-(4-(chloromethyl)phenyl)-1-methyl-1H-imidazole

To a mixture of (4-(1-methyl-1H-imidazol-4-yl)phenyl)methanol (15 g), DMF (2.5 mL) and DCM (400 mL) was added thionyl chloride (17.36 mL) under ice-cooling, and the mixture was stirred at room temperature for 2 hr. The reaction mixture was concentrated, saturated aqueous sodium hydrogen carbonate solution was added, and the mixture was extracted with DCM. The organic layer was dried over anhydrous sodium sulfate and concentrated under reduced pressure. The residue was purified by silica gel column chromatography (ethyl acetate/petroleum ether) to give the title compound (11 g).

MS: M+H 207.06.

C) 7-(4-(1-methyl-1H-imidazol-4-yl)benzyl)-2,3-dihydrofuro[3,2-b]pyridine-5-carboxylic acid A mixture of methyl 7-(4,4,5,5-tetramethyl-1,3,2-dioxaborolan-2-yl)-2,3-dihydrofuro[3,2-b]pyridine-5-carboxylate (400 mg), 4-(4-(chloromethyl)phenyl)-1-methyl-1H-imidazole (325 mg), Pd(PPh$_3$)$_4$ (76 mg), potassium carbonate (725 mg), DME (7.5 mL) and water (4.5 mL) was subjected to microwave irradiation at 150° C. for 30 min. The reaction mixture was diluted by adding ethyl acetate and water, and the mixture was extracted with 1 M sodium hydroxide. The obtained aqueous layer was neutralized by adding 1 M hydrochloric acid. The precipitated solid was collected by filtration and dried under reduced pressure to give the title compound (164.2 mg).

MS: [M+H]$^+$ 336.1.

D) 1,5-anhydro-2,3-dideoxy-3-(((7-(4-(1-methyl-1H-imidazol-4-yl)benzyl)-2,3-dihydrofuro[3,2-b]pyridin-5-yl)carbonyl)amino)-L-threo-pentitol

(synonym) N-((3R,4S)-3-hydroxytetrahydro-2H-pyran-4-yl)-7-(4-(1-methyl-1H-imidazol-4-yl)benzyl)-2,3-dihydrofuro[3,2-b]pyridine-5-carboxamide To a mixture of 7-(4-(1-methyl-1H-imidazol-4-yl)benzyl)-2,3-dihydrofuro[3,2-b]pyridine-5-carboxylic acid (100 mg), (3R,4S)-4-aminotetrahydro-2H-pyran-3-ol hydrochloride (55.0 mg), TEA (0.062 mL), HOBt (60.4 mg) and DMF (3.0 mL) was added WSC (0.078 mL) under ice-cooling. The mixture was stirred at room temperature overnight, and the solvent was evaporated under reduced pressure. To the residue was added water, and the mixture was extracted with ethyl acetate. The organic layer was separated, washed with saturated aqueous sodium hydrogen carbonate and saturated brine, dried over anhydrous sodium sulfate, and concentrated under reduced pressure. The obtained solid was crystallized from ethyl acetate/hexane to give the title compound (81 mg).

$^1$H NMR (400 MHz, DMSO-d$_6$) δ 1.59 (1H, qd, J=12.3, 4.5 Hz), 1.77-1.85 (1H, m), 3.01 (1H, t, J=10.5 Hz), 3.24-3.39 (3H, m), 3.54 (1H, tt, J=9.8, 5.1 Hz), 3.67 (3H, s), 3.69-3.83 (3H, m), 3.90 (2H, s), 4.76 (2H, t, J=8.9 Hz), 4.93 (1H, d, J=5.4 Hz), 7.20 (2H, d, J=8.3 Hz), 7.54 (1H, d, J=1.2 Hz), 7.60 (1H, d, J=1.0 Hz), 7.63-7.68 (3H, m), 8.25 (1H, d, J=8.3 Hz).

Example 76

1,5-anhydro-2,3-dideoxy-3-(((7-(3-fluoro-4-((2-methoxyethyl)carbamoyl)benzyl)-2,3-dihydrofuro[3,2-b]pyridin-5-yl)carbonyl)amino)-L-threo-pentitol

(synonym) 7-(3-fluoro-4-((2-methoxyethyl)carbamoyl)benzyl)-N-((3R,4S)-3-hydroxytetrahydro-2H-pyran-4-yl)-2,3-dihydrofuro[3,2-b]pyridine-5-carboxamide

A) tert-butyl 2-fluoro-4-methylbenzoate

A mixture of 2-fluoro-4-methylbenzoic acid (10 g) and toluene (160 mL) was stirred under an argon atmosphere at 80° C. for 30 min. A mixture of 1,1-di-tert-butoxy-N,N-dimethylmethanamine (31.1 mL) and toluene (40 mL) was added dropwise at 80° C., and the mixture was stirred at 100° C. for 2 hr. To the reaction mixture was added dropwise a mixture of 1,1-di-tert-butoxy-N,N-dimethylmethanamine (15.56 mL) and toluene (20 mL) at 80° C., and the mixture was stirred at 100° C. for 2 hr. The reaction mixture was purified by silica gel column chromatography (NH, ethyl acetate) to give the title compound (11.19 g). The compound was used in the next step without further purification.

$^1$H NMR (400 MHz, DMSO-d$_6$) δ 1.53 (9H, s), 2.36 (3H, s), 7.06-7.20 (2H, m), 7.64-7.75 (1H, m).

B) tert-butyl 4-(bromomethyl)-2-fluorobenzoate

To a mixture of tert-butyl 2-fluoro-4-methylbenzoate (11.1 g), NBS (9.40 g) and trifluorotoluene (140 mL) was added AIBN (0.867 g) at room temperature. The mixture was stirred under an argon atmosphere at 80° C. for 1 hr. The reaction mixture was cooled to room temperature and partitioned between ethyl acetate and water. The organic layer was washed with saturated brine, dried over anhydrous sodium sulfate, and concentrated under reduced pressure. The residue was purified by silica gel column chromatography (ethyl acetate/hexane) to give the title compound (12.37 g).

$^1$H NMR (400 MHz, DMSO-d$_6$) δ 1.53-1.57 (9H, m), 4.73 (2H, s), 7.34-7.45 (2H, m), 7.80 (1H, t, J=7.8 Hz).

C) methyl 7-(4,4,5,5-tetramethyl-1,3,2-dioxaborolan-2-yl)-2,3-dihydrofuro[3,2-b]pyridine-5-carboxylate A mixture of methyl 7-(4,4,5,5-tetramethyl-1,3,2-dioxaborolan-2-yl)furo[3,2-b]pyridine-5-carboxylate (9.56 g), 10% palladium-carbon (NX type, 50% wet with water, 1.92 g) and MeOH (300 mL) was stirred under a hydrogen atmosphere of 0.5-0.8 MPa at 30° C. for 4 hr. To the reaction mixture was added THF (300 mL), and the mixture was stirred under a hydrogen atmosphere of 0.5-0.8 MPa at room temperature overnight. The catalyst was filtered off, and the filtrate was concentrated under reduced pressure to give the title compound (9.52 g).

$^1$H NMR (400 MHz, DMSO-d$_6$) δ 1.23-1.36 (12H, m), 3.26-3.32 (2H, m), 3.83 (3H, s), 4.72-4.79 (2H, m), 7.98 (1H, s).

D) methyl 7-(4-(tert-butoxycarbonyl)-3-fluorobenzyl)-2,3-dihydrofuro[3,2-b]pyridine-5-carboxylate A mixture of methyl 7-(4,4,5,5-tetramethyl-1,3,2-dioxaborolan-2-yl)-2,3-dihydrofuro[3,2-b]pyridine-5-carboxylate (2.0 g), tert-butyl 4-(bromomethyl)-2-fluorobenzoate (2.09 g), Pd(PPh$_3$)$_4$ (379 mg), potassium carbonate (3.62 g), DME (20 mL) and water (12 mL) was subjected to microwave irradiation at 70° C. for 10 min. Water was added to the reaction mixture, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (1.96 g).

MS: [M+H]$^+$ 388.2.

E) 1,5-anhydro-3-(((7-(4-(tert-butoxycarbonyl)-3-fluorobenzyl)-2,3-dihydrofuro[3,2-b]pyridin-5-yl)carbonyl)amino)-2,3-dideoxy-L-threo-pentitol To a mixture of methyl 7-(4-(tert-butoxycarbonyl)-3-fluorobenzyl)-2,3-dihydrofuro[3,2-b]pyridine-5-carboxylate (1.1 g) and THF (10 mL) was added 1 M aqueous sodium hydroxide solution (5.68 mL) at room temperature, and the mixture was stirred at room temperature for 4 hr. After neutralization with 1 M hydrochloric acid, the reaction mixture was concentrated under reduced pressure to give 7-(4-(tert-butoxycarbonyl)-3-fluorobenzyl)-2,3-dihydrofuro[3,2-b]pyridine-5-carboxylic acid as a solid. A mixture of the obtained solid, (3R,4S)-4-aminotetrahydro-2H-pyran-3-ol hydrochloride (0.567 mg), HATU (1.62 g), TEA (1.19 mL) and DMF (10 mL) was stirred at room temperature for 5 hr. To the reaction mixture was added water at room temperature, and the precipitated solid was collected by filtration and dried under reduced pressure to give the title compound (1.22 g).

MS: [M+H]$^+$ 473.2.

F) 1,5-anhydro-3-(((7-(4-carboxy-3-fluorobenzyl)-2, 3-dihydrofuro[3,2-b]pyridin-5-yl)carbonyl)amino)-2, 3-dideoxy-L-threo-pentitol A mixture of 1,5-anhydro-3-(((7-(4-(tert-butoxycarbonyl)-3-fluorobenzyl)-2,3-dihydrofuro[3,2-b]pyridin-5-yl) carbonyl)amino)-2,3-dideoxy-L-threo-pentitol (1.44 g) and 4 M hydrochloric acid-ethyl acetate solution (50 mL) was stirred at room temperature for 3 hr. The reaction mixture was concentrated under reduced pressure, and the obtained residue was partitioned between ethyl acetate-1 M sodium hydroxide. The aqueous layer was neutralized by adding 1 M hydrochloric acid under ice-cooling, and the precipitated solid was collected by filtration and dried under reduced pressure to give the title compound (1.12 g).

MS: [M+H]$^+$ 417.2.

G) 1,5-anhydro-2,3-dideoxy-3-(((7-(3-fluoro-4-((2-methoxyethyl)carbamoyl)benzyl)-2,3-dihydrofuro[3, 2-b]pyridin-5-yl)carbonyl)amino)-L-threo-pentitol (synonym) 7-(3-fluoro-4-((2-methoxyethyl)carbamoyl)benzyl)-N-((3R,4S)-3-hydroxytetrahydro-2H-pyran-4-yl)-2,3-dihydrofuro[3,2-b]pyridine-5-carboxamide To a mixture of 1,5-anhydro-3-(((7-(4-carboxy-3-fluorobenzyl)-2,3-dihydrofuro[3,2-b]pyridin-5-yl)carbonyl) amino)-2,3-dideoxy-L-threo-pentitol (1.1 g), 2-methoxyethanamine (0.344 mL), HOBt (535 mg) and DMF (30 mL) was added WSC (0.695 mL) at 0° C. After stirring at room temperature overnight, the reaction mixture was concentrated under reduced pressure. The obtained residue was diluted with ethyl acetate, washed with saturated aqueous sodium hydrogen carbonate solution and saturated brine, dried over anhydrous sodium sulfate, and concentrated under reduced pressure. The obtained solid was recrystallized from ethyl acetate/heptane to give the title compound (858 mg).

$^1$H NMR (400 MHz, DMSO-d$_6$) δ 1.59 (1H, qd, J=12.3, 4.6 Hz), 1.81 (1H, dd, J=13.0, 4.4 Hz), 3.01 (1H, t, J=10.5 Hz), 3.26 (3H, s), 3.30-3.43 (7H, m), 3.54 (1H, tt, J=10.0, 5.0 Hz), 3.69-3.84 (3H, m), 3.99 (2H, s), 4.75 (2H, t, J=8.8 Hz), 4.92 (1H, d, J=5.6 Hz), 7.07-7.21 (2H, m), 7.54 (1H, t, J=7.7 Hz), 7.69 (1H, s), 8.20-8.31 (2H, m).

Example 77

1,5-anhydro-2,3-dideoxy-3-(((7-(3-fluoro-4-(((2S)-tetrahydrofuran-2-ylmethyl)carbamoyl)benzyl)-2,3-dihydrofuro[3,2-b]pyridin-5-yl)carbonyl)amino)-L-threo-pentitol (synonym) 7-(3-fluoro-4-((((S)-tetrahydrofuran-2-yl)methyl)carbamoyl)benzyl)-N-((3R,4S)-3-hydroxytetrahydro-2H-pyran-4-yl)-2,3-dihydrofuro[3,2-b]pyridine-5-carboxamide A mixture of 1,5-anhydro-3-(((7-(4-carboxy-3-fluorobenzyl)-2,3-dihydrofuro[3,2-b]pyridin-5-yl)carbonyl)amino)-2, 3-dideoxy-L-threo-pentitol (100 mg), 1-((2S)-tetrahydrofuran-2-yl)methanamine (36.4 mg), WSC (0.085 mL), HOBt·H$_2$O (73.6 mg), TEA (0.100 mL) and DMF (2.0 mL) was stirred at room temperature overnight. To the reaction mixture was added saturated brine, and the mixture was extracted with ethyl acetate. The organic layer was dried over anhydrous magnesium sulfate and concentrated under reduced pressure. The residue was purified by silica gel column chromatography (NH, ethyl acetate/hexane). The obtained solid was crystallized from ethyl acetate/hexane to give the title compound (91 mg).

$^1$H NMR (400 MHz, DMSO-d$_6$) δ 1.47-1.68 (2H, m), 1.69-1.95 (4H, m), 3.01 (1H, t, J=10.5 Hz), 3.21-3.32 (3H, m), 3.33-3.40 (2H, m), 3.48-3.57 (1H, m), 3.58-3.65 (1H, m), 3.68-3.84 (4H, m), 3.89-3.96 (1H, m), 3.99 (2H, s), 4.75 (2H, t, J=8.9 Hz), 4.92 (1H, d, J=5.6 Hz), 7.09-7.24 (2H, m), 7.53 (1H, t, J=7.8 Hz), 7.69 (1H, s), 8.16-8.36 (2H, m).

Example 95 methyl ((2-fluoro-4-((5-(((3R,4S)-3-hydroxytetrahydro-2H-pyran-4-yl)carbamoyl)-2,3-dihydrofuro[3, 2-b]pyridin-7-yl)methyl)benzoyl)amino)acetate A mixture of 1,5-anhydro-3-(((7-(4-carboxy-3-fluorobenzyl)-2,3-dihydrofuro[3,2-b]pyridin-5-yl)carbonyl)amino)-2, 3-dideoxy-L-threo-pentitol (200 mg), glycine methyl ester hydrochloride (90 mg), WSC (112 mg), HOBt (97 mg), TEA (0.201 mL) and DMF (3.0 mL) was stirred at 50° C. for 3 hr. To the reaction mixture was added saturated brine, and the mixture was extracted with ethyl acetate. The organic layer was dried over anhydrous magnesium sulfate and concentrated under reduced pressure. The residue was purified by silica gel column chromatography (NH, ethyl acetate/hexane). The obtained solid was crystallized from ethyl acetate/hexane to give the title compound (183 mg).

$^1$H NMR (400 MHz, DMSO-d$_6$) δ 1.51-1.68 (1H, m), 1.75-1.86 (1H, m), 3.01 (2H, t, J=10.5 Hz), 3.26-3.32 (1H, m), 3.33-3.39 (2H, m), 3.49-3.60 (1H, m), 3.68-3.86 (4H, m), 3.93-4.06 (5H, m), 4.75 (2H, t, J=8.9 Hz), 4.92 (1H, d, J=5.9 Hz), 7.12-7.25 (2H, m), 7.61 (1H, t, J=7.8 Hz), 7.70 (1H, s), 8.27 (1H, d, J=8.1 Hz), 8.52-8.73 (1H, m).

Example 96

((2-fluoro-4-((5-(((3R,4S)-3-hydroxytetrahydro-2H-pyran-4-yl)carbamoyl)-2,3-dihydrofuro[3,2-b]pyridin-7-yl)methyl)benzoyl)amino)acetic acid To a mixture of methyl 2-(2-fluoro-4-((5-(((3R,4S)-3-hydroxytetrahydro-2H-pyran-4-yl)carbamoyl)-2,3-dihydrofuro[3,2-b]pyridin-7-yl)methyl)benzamido)acetate (220 mg), MeOH (2.0 mL) and THF (2.0 mL) was added 1 M aqueous sodium hydroxide solution (2.0 mL) at room temperature, and the mixture was stirred at 50° C. for 1 hr. The reaction mixture was neutralized with 1 M hydrochloric acid, and the mixture was extracted with ethyl acetate. The organic layer was washed with saturated brine, dried over anhydrous magnesium sulfate, and concentrated under reduced pressure. The obtained solid was crystallized from ethyl acetate/hexane to give the title compound (179 mg).

$^1$H NMR (400 MHz, DMSO-$d_6$) δ 1.47-1.68 (1H, m), 1.74-1.86 (1H, m), 2.94-3.08 (1H, m), 3.26-3.32 (1H, m), 3.33-3.39 (2H, m), 3.47-3.61 (1H, m), 3.67-3.84 (3H, m), 3.88-3.94 (2H, m), 4.01 (2H, s), 4.75 (2H, t, J=8.8 Hz), 4.92 (1H, d, J=5.6 Hz), 7.10-7.26 (2H, m), 7.62 (1H, t, J=7.8 Hz), 7.70 (1H, s), 8.27 (1H, d, J=8.1 Hz), 8.39-8.55 (1H, m), 12.60 (1H, s).

Example 99

1,5-anhydro-2,3-dideoxy-3-(((7-(4-((2-(diethylamino)-2-oxoethyl)carbamoyl)-3-fluorobenzyl)-2,3-dihydrofuro[3,2-b]pyridin-5-yl)carbonyl)amino)-L-threo-pentitol A mixture of 2-(2-fluoro-4-((5-(((3R,4S)-3-hydroxytetrahydro-2H-pyran-4-yl)carbamoyl)-2,3-dihydrofuro[3,2-b]pyridin-7-yl)methyl)benzamido)acetic acid (50 mg), N-ethylethanamine (23.17 mg), WSC (49.2 mg), HOBt·H$_2$O (24.26 mg), TEA (0.044 mL) and DMF (2.0 mL) was stirred at room temperature overnight. To the reaction mixture was added HATU (80 mg), and the mixture was stirred at room temperature for 3 hr. To the reaction mixture was added saturated brine, and the mixture was extracted with ethyl acetate. The organic layer was washed with saturated brine, dried over anhydrous magnesium sulfate, and concentrated under reduced pressure. The residue was purified by silica gel column chromatography (NH, ethyl acetate/hexane) to give the title compound (18.0 mg).

$^1$H NMR (300 MHz, DMSO-$d_6$) δ 0.93-1.08 (3H, m), 1.09-1.22 (3H, m), 1.45-1.68 (1H, m), 1.68-1.92 (1H, m), 2.94-3.08 (1H, m), 3.24-3.31 (4H, m), 3.33-3.39 (3H, m), 3.46-3.64 (1H, m), 3.69-3.86 (3H, m), 4.01 (2H, s), 4.11 (2H, d, J=5.3 Hz), 4.75 (2H, t, J=8.7 Hz), 4.92 (1H, d, J=6.0 Hz), 7.07-7.28 (2H, m), 7.60-7.76 (2H, m), 8.11-8.23 (1H, m), 8.26 (1H, d, J=8.3 Hz).

Example 102

1,5-anhydro-2,3-dideoxy-3-(((7-(3-fluoro-4-(((2S)-tetrahydrofuran-2-ylmethyl)carbamoyl)benzyl)furo[3,2-b]pyridin-5-yl)carbonyl)amino)-L-threo-pentitol (synonym) 7-(3-fluoro-4-(((((S)-tetrahydrofuran-2-yl)methyl)carbamoyl)benzyl)-N-((3R,4S)-3-hydroxytetrahydro-2H-pyran-4-yl)furo[3,2-b]pyridine-5-carboxamide A) methyl 7-(4-(tert-butoxycarbonyl)-3-fluorobenzyl)furo[3,2-b]pyridine-5-carboxylate A mixture of methyl 7-(4,4,5,5-tetramethyl-1,3,2-dioxaborolan-2-yl)furo[3,2-b]pyridine-5-carboxylate (2.6 g), tert-butyl 4-(bromomethyl)-2-fluorobenzoate (2.8 g), Pd(PPh$_3$)$_4$ (466 mg), potassium carbonate (4.46 g), DME (12 mL) and water (2 mL) was subjected to microwave irradiation at 80° C. for 20 min. To the reaction mixture was added saturated brine, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (2.30 g).

MS: [M+H]$^+$ 386.2.

B) 7-(4-(tert-butoxycarbonyl)-3-fluorobenzyl)furo[3,2-b]pyridine-5-carboxylic acid To a mixture of methyl 7-(4-(tert-butoxycarbonyl)-3-fluorobenzyl)furo[3,2-b]pyridine-5-carboxylate (1.63 g), THF (30 mL) and MeOH (30 mL) was added 1 M aqueous sodium hydroxide solution (8.46 mL) at room temperature, and the mixture was stirred at room temperature for 2 hr. The reaction mixture was concentrated under reduced pressure, ice water was added to the residue, and the mixture was washed with ethyl acetate. The aqueous layer was neutralized by adding 1 M hydrochloric acid under ice-cooling and stirred for a while, and the precipitated solid was collected by filtration to give the title compound (1.53 g).

MS: [M+H]$^+$ 372.2.

C) 1,5-anhydro-3-(((7-(4-(tert-butoxycarbonyl)-3-fluorobenzyl)furo[3,2-b]pyridin-5-yl)carbonyl)amino)-2,3-dideoxy-L-threo-pentitol To a mixture of 7-(4-(tert-butoxycarbonyl)-3-fluorobenzyl)furo[3,2-b]pyridine-5-carboxylic acid (1.53 g), (3R,4S)-4-aminotetrahydro-2H-pyran-3-ol hydrochloride (759 mg), HOBt (835 mg) and DMF (20 mL) was added WSC (1.084 mL). The mixture was stirred at room temperature overnight. Water was added to the reaction mixture, and the mixture was extracted with ethyl acetate. The organic layer was separated, washed with saturated aqueous sodium hydrogen carbonate and saturated brine, dried over anhydrous sodium sulfate, and concentrated under reduced pressure. The obtained solid was crystallized from ethyl acetate/ethanol to give the title compound (1.81 g).

MS: [M+H]$^+$ 471.3.

D) 1,5-anhydro-3-(((7-(4-carboxy-3-fluorobenzyl)furo[3,2-b]pyridin-5-yl)carbonyl)amino)-2,3-dideoxy-L-threo-pentitol A mixture of 1,5-anhydro-3-(((7-(4-(tert-butoxycarbonyl)-3-fluorobenzyl)furo[3,2-b]pyridin-5-yl)carbonyl)amino)-2,3-dideoxy-L-threo-pentitol (1.91 g) and 4 M hydrochloric acid-ethyl acetate solution (50 mL) was stirred at room temperature for 3 hr. The reaction mixture was concentrated under reduced pressure, and the obtained residue was partitioned between ethyl acetate-1 M sodium hydroxide. The aqueous layer was neutralized by adding 1 M hydrochloric acid under ice-cooling, and the precipitated solid was collected by filtration and dried under reduced pressure to give the title compound (1.32 g)

MS: [M+H]$^+$ 415.2.

E) 1,5-anhydro-2,3-dideoxy-3-(((7-(3-fluoro-4-(((2S)-tetrahydrofuran-2-ylmethyl)carbamoyl)benzyl)furo[3,2-b]pyridin-5-yl)carbonyl)amino)-L-threo-pentitol (synonym) 7-(3-fluoro-4-(((((S)-tetrahydrofuran-2-yl)methyl)carbamoyl)benzyl)-N-((3R,4S)-3-hydroxytetrahydro-2H-pyran-4-yl)furo[3,2-b]pyridine-5-carboxamide To a mixture of 1,5-anhydro-3-(((7-(4-carboxy-3-fluorobenzyl)furo[3,2-b]pyridin-5-yl)carbonyl)amino)-2,3- dideoxy-L-threo-pentitol (1.31 g), 1-((2S)-tetrahydrofuran-2-yl)methanamine (0.480 g), HOBt (641 mg) and DMF (30 mL) was added WSC (0.832 mL) under ice-cooling. The mixture was stirred at room temperature overnight. To the reaction mixture was added water, and the mixture was extracted with ethyl acetate. The organic layer was washed with saturated aqueous sodium hydrogen carbonate and saturated brine, dried over anhydrous sodium sulfate, and concentrated under reduced pressure. The residue was crystallized from ethyl acetate/heptane to give the title compound (1.21 g). $^1$H NMR (400 MHz, DMSO-d$_6$) δ 1.49-1.71 (2H, m), 1.73-1.96 (4H, m), 3.03 (1H, t, J=10.5 Hz), 3.19-3.40 (3H, m), 3.52-3.67 (2H, m), 3.70-3.85 (4H, m), 3.93 (1H, quin, J=6.2 Hz), 4.41 (2H, s), 4.96 (1H, d, J=5.6 Hz), 7.12-7.32 (3H, m), 7.54 (1H, t, J=7.8 Hz), 7.92 (1H, s), 8.16-8.35 (1H, m), 8.47 (1H, d, J=2.4 Hz), 8.56 (1H, d, J=8.3 Hz).

Example 109

1,5-anhydro-2,3-dideoxy-3-(((7-(3-fluoro-4-((2-methoxyethyl)carbamoyl)benzyl)furo[3,2-b]pyridin-5-yl)carbonyl)amino)-L-threo-pentitol (synonym) 7-(3-fluoro-4-((2-methoxyethyl)carbamoyl)benzyl)-N-((3R,4S)-3-hydroxytetrahydro-2H-pyran-4-yl)furo[3,2-b]pyridine-5-carboxamide A mixture of 1,5-anhydro-3-(((7-(4-carboxy-3-fluorobenzyl)furo[3,2-b]pyridin-5-yl)carbonyl)amino)-2,3-dideoxy-L-threo-pentitol (70 mg), 2-methoxyethanamine (38.1 mg), WSC (0.089 mL), HOBt·H$_2$O (51.7 mg), TEA (0.071 mL) and DMF (2.0 mL) was stirred at room temperature overnight. To the reaction mixture was added HATU (128 mg), and the mixture was stirred at room temperature for 1 hr. To the reaction mixture was added saturated brine, and the mixture was extracted with ethyl acetate. The organic layer was washed with saturated brine, dried over anhydrous magnesium sulfate, and concentrated under reduced pressure. The residue was purified by silica gel column chromatography (NH, ethyl acetate/hexane), and the obtained solid was crystallized from ethyl acetate/hexane to give the title compound (31.3 mg).
$^1$H NMR (400 MHz, DMSO-d$_6$) δ 1.55-1.70 (1H, m), 1.77-1.90 (1H, m), 3.03 (1H, s), 3.23-3.27 (3H, m), 3.28-3.31 (1H, m), 3.35-3.47 (4H, m), 3.51-3.68 (1H, m), 3.80 (3H, td, J=10.2, 4.3 Hz), 4.41 (2H, s), 4.96 (1H, d, J=5.9 Hz), 7.17-7.24 (2H, m), 7.28 (1H, d, J=11.5 Hz), 7.55 (1H, t, J=7.8 Hz), 7.92 (1H, s), 8.19-8.31 (1H, m), 8.45-8.49 (1H, m), 8.51-8.63 (1H, m).

Example 111

1,5-anhydro-2,3-dideoxy-3-(((7-(1-(3-fluoro-4-((2-methoxyethyl)carbamoyl)phenyl)ethyl)furo[3,2-b]pyridin-5-yl)carbonyl)amino)-L-threo-pentitol A) 1-(3-fluoro-4-(methoxymethoxy)phenyl)ethanone A mixture of 1-(3-fluoro-4-hydroxyphenyl)ethanone (5.0 g), chloro(methoxy)methane (2.96 mL), potassium carbonate (5.38 g) and DMF (50 mL) was stirred at room temperature for 2 hr. To the reaction mixture was added saturated aqueous sodium hydrogen carbonate solution at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/petroleum ether) to give the title compound (6.09 g).
MS: [M+H]$^+$ 199.0.

B) methyl 7-(1-(3-fluoro-4-(methoxymethoxy)phenyl)ethyl)furo[3,2-b]pyridine-5-carboxylate A mixture of 1-(3-fluoro-4-(methoxymethoxy)phenyl)ethanone (1.70 g), 4-methylbenzenesulfonohydrazide (2.40 g) and toluene (34.3 mL) was stirred at 80° C. for 2 hr. To the reaction mixture were added methyl 7-(4,4,5,5-tetramethyl-1,3,2-dioxaborolan-2-yl)furo[3,2-b]pyridine-5-carboxylate (3.12 g) and potassium carbonate (2.37 g), and the mixture was stirred at 110° C. for 4 hr. After cooling the reaction mixture to room temperature, saturated brine was added, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (1.6 g).
MS: [M+H]$^+$ 360.0.

C) methyl 7-(1-(3-fluoro-4-hydroxyphenyl)ethyl)furo[3,2-b]pyridine-5-carboxylate A mixture of methyl 7-(1-(3-fluoro-4-(methoxymethoxy)phenyl)ethyl)furo[3,2-b]pyridine-5-carboxylate (2.1 g) and 2 M hydrochloric acid methanol solution (4.26 g) was stirred at room temperature overnight. To the reaction mixture was added saturated brine at room temperature, and the mixture was extracted with ethyl acetate. The organic layer was separated, washed with saturated brine, dried over anhydrous magnesium sulfate, and concentrated under reduced pressure to give the title compound (960 mg). The compound was used in the next step without further purification.
MS: [M+H]$^+$ 316.0.

D) methyl 7-(1-(3-fluoro-4-(((trifluoromethyl)sulfonyl)oxy)phenyl)ethyl)furo[3,2-b]pyridine-5-carboxylate To a mixture of methyl 7-(1-(3-fluoro-4-hydroxyphenyl)ethyl)furo[3,2-b]pyridine-5-carboxylate (860 mg) and pyridine (3 mL) was added trifluoromethanesulfonic anhydride (5.46 mL) under ice-cooling, and the mixture was stirred under ice-cooling for 3 hr. To the reaction mixture was added saturated brine, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (1.01 g).
MS: [M+H]$^+$ 448.0.

E) methyl 7-(1-(3-fluoro-4-((2-(trimethylsilyl)ethoxy)carbonyl)phenyl)ethyl)furo[3,2-b]pyridine-5-carboxylate A mixture of methyl 7-(1-(3-fluoro-4-(((trifluoromethyl)sulfonyl)oxy)phenyl)ethyl)furo[3,2-b]pyridine-5-carboxylate (1.01 g), 2-(trimethylsilyl)ethanol (0.971 mL), palladium(II) acetate (76 mg), 1,3-bis(diphenylphosphino)propane (140 mg), TEA (0.629 mL) and DMF (10 mL) was stirred under a carbon monoxide atmosphere at 70° C. for 4 hr. The reaction mixture was concentrated, and the residue was purified by silica gel column chromatography (ethyl acetate/hexane) to give the title compound (801 mg).
MS: [M+H]+ 444.1.

F) 2-fluoro-4-(1-(5-(methoxycarbonyl)furo[3,2-b]pyridin-7-yl)ethyl)benzoic acid To a mixture of methyl 7-(1-(3-fluoro-4-((2-(trimethylsilyl)ethoxy)carbonyl)phenyl)ethyl)furo[3,2-b]pyridine-5-carboxylate (810 mg) and THF (20 mL) was added 1 M tetra-n-butylammonium fluoride THF solution (3.65 mL) under ice-cooling, and the mixture was stirred at room temperature for 3 hr. To the reaction mixture was added 1 N hydrochloric acid at 0° C., and the mixture was extracted with ethyl acetate. The organic layer was separated, washed with saturated brine, dried over anhydrous magnesium sulfate, and concentrated under reduced pressure. The obtained solid was crystallized from ethyl acetate/hexane to give the title compound (361 mg).
MS: [M+H]+ 344.0.

G) methyl 7-(1-(3-fluoro-4-((2-methoxyethyl)carbamoyl)phenyl)ethyl)furo[3,2-b]pyridine-5-carboxylate A mixture of 2-fluoro-4-(1-(5-(methoxycarbonyl)furo[3,2-b]pyridin-7-yl)ethyl)benzoic acid (300 mg), 2-methoxyethanamine (131 mg), HATU (665 mg), TEA (0.487 mL) and DMF (3.0 mL) was stirred at room temperature for 2 hr. To the reaction mixture was added saturated brine, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (162 mg).
MS: [M+H]+ 401.1.

H) 1,5-anhydro-2,3-dideoxy-3-(((7-(1-(3-fluoro-4-((2-methoxyethyl)carbamoyl)phenyl)ethyl)furo[3,2-b]pyridin-5-yl)carbonyl)amino)-L-threo-pentitol To a mixture of methyl 7-(1-(3-fluoro-4-((2-methoxyethyl)carbamoyl)phenyl)ethyl)furo[3,2-b]pyridine-5-carboxylate (52 mg), MeOH (1 mL) and THF (1 mL) was added 4 M aqueous lithium hydroxide solution (0.097 mL) at room temperature. After stirring at room temperature for 2 hr, 6 M hydrochloric acid (0.065 mL) was added, and the mixture was concentrated to give 7-(1-(3-fluoro-4-((2-methoxyethyl)carbamoyl)phenyl)ethyl)furo[3,2-b]pyridine-5-carboxylic acid as a solid. A mixture of the obtained solid, (3R,4S)-4-aminotetrahydro-2H-pyran-3-ol hydrochloride (30 mg), HATU (74.1 mg), TEA (0.036 mL) and DMF (1.0 mL) was stirred at room temperature for 2 hr. To the reaction mixture was added saturated brine, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (52.0 mg).
$^1$H NMR (400 MHz, DMSO-$d_6$) δ 1.59-1.69 (1H, m), 1.71-1.79 (3H, m), 1.80-1.90 (1H, m), 2.95-3.11 (1H, m), 3.25 (3H, s), 3.33-3.44 (5H, m), 3.52-3.67 (1H, m), 3.72-3.89 (3H, m), 4.80 (1H, q, J=7.1 Hz), 4.97 (1H, dd, J=5.5, 4.3 Hz), 7.16-7.26 (2H, m), 7.31 (1H, dd, J=11.7, 1.5 Hz), 7.54 (1H, t, J=7.8 Hz), 7.98 (1H, s), 8.26 (1H, brs), 8.44 (1H, d, J=2.2 Hz), 8.57 (1H, d, J=8.3 Hz).

Example 112

1,5-anhydro-2,3-dideoxy-3-(((7-(1-(3-fluoro-4-((2-methoxyethyl)carbamoyl)phenyl)ethyl)-2,3-dihydrofuro[3,2-b]pyridin-5-yl)carbonyl)amino)-L-threo-pentitol

A) methyl 7-(1-(3-fluoro-4-((2-methoxyethyl)carbamoyl)phenyl)ethyl)-2,3-dihydrofuro[3,2-b]pyridine-5-carboxylate A mixture of methyl 7-(1-(3-fluoro-4-((2-methoxyethyl)carbamoyl)phenyl)ethyl)furo[3,2-b]pyridine-5-carboxylate (160 mg), 10% palladium-carbon (NX type, 50% wet with water, 32 mg) and MeOH (30 mL) was stirred under a hydrogen atmosphere of 5 MPa at 50° C. for 4.5 hr. The catalyst was filtered off, and the filtrate was concentrated under reduced pressure to give the title compound (140 mg). The compound was used in the next step without further purification.
MS: [M+H]+ 403.2.

B) 7-(1-(3-fluoro-4-((2-methoxyethyl)carbamoyl)phenyl)ethyl)-2,3-dihydrofuro[3,2-b]pyridine-5-carboxylic acid The title compound was obtained by a method similar to that in step H of Example 111.
MS: [M+H]+ 389.1.

C) 1,5-anhydro-2,3-dideoxy-3-(((7-(1-(3-fluoro-4-((2-methoxyethyl)carbamoyl)phenyl)ethyl)-2,3-dihydrofuro[3,2-b]pyridin-5-yl)carbonyl)amino)-L-threo-pentitol The title compound was obtained by a method similar to that in step H of Example 111.
$^1$H NMR (400 MHz, DMSO-$d_6$) δ 1.49-1.66 (4H, m), 1.75-1.85 (1H, m), 2.94-3.07 (2H, m), 3.25 (3H, s), 3.28-3.31 (1H, m), 3.35-3.47 (5H, m), 3.49-3.61 (1H, m), 3.68-3.87 (3H, m), 4.34 (1H, q, J=7.0 Hz), 4.72 (2H, t, J=9.0 Hz), 4.92 (1H, t, J=5.4 Hz), 7.08-7.30 (2H, m), 7.48-7.59 (1H, m), 7.72 (1H, s), 8.12-8.37 (2H, m).

Example 113

1,5-anhydro-2,3-dideoxy-3-(((7-((2-methyl-1-oxo-2,3-dihydro-1H-isoindol-5-yl)methyl)-2,3-dihydrofuro[3,2-b]pyridin-5-yl)carbonyl)amino)-L-threo-pentitol

A) 2-methyl-1-oxoisoindoline-5-carbaldehyde

A mixture of 5-bromo-2-methylisoindolin-1-one (1030 mg), 2-isocyano-2-methylpropane (947 mg), sodium carbonate (579 mg), palladium(II) acetate (102 mg), biphenyl-2-yl(di-tert-butyl)phosphine (272 mg), triethylsilane (2.18 mL) and DMF (20 mL) was stirred under a nitrogen atmosphere at 75° C. for 2.5 hr. After cooling the reaction mixture to room temperature, water was added, and the mixture was extracted with ethyl acetate. The organic layer was washed with saturated brine, dried over anhydrous magnesium sulfate, and concentrated under reduced pressure. The residue was purified by silica gel column chromatography (MeOH/ethyl acetate) to give the title compound (690 mg).
MS: M+H 176.4.

B) 5-(hydroxymethyl)-2-methylisoindolin-1-one

To a mixture of 2-methyl-1-oxoisoindoline-5-carbaldehyde (660 mg) and THF (20 mL) was added sodium borohydride (285 mg) at 0° C., and the mixture was stirred at room temperature for 1 hr. To the reaction mixture was added water, and the mixture was extracted with ethyl acetate. The organic layer was washed with saturated brine, dried over anhydrous magnesium sulfate solvent, and concentrated under reduced pressure. The residue was purified by silica gel column chromatography (MeOH/ethyl acetate) to give the title compound (576 mg).
MS: [M+H]$^+$ 178.4.

C) 5-(chloromethyl)-2-methylisoindolin-1-one

To a mixture of 5-(hydroxymethyl)-2-methylisoindolin-1-one (576 mg), toluene (5 mL) and acetonitrile (10 mL) was added thionyl chloride (0.475 mL) at 0° C. After stirring at room temperature for 1 hr, aqueous sodium hydrogen carbonate solution was added to the reaction mixture, and the mixture was extracted with ethyl acetate. The organic layer was washed with saturated brine, dried over anhydrous magnesium sulfate, and concentrated under reduced pressure. The residue was purified by silica gel column chromatography (MeOH/ethyl acetate) to give the title compound (126 mg).
MS: [M+H]$^+$ 196.4.

D) methyl 7-((2-methyl-1-oxo-2,3-dihydro-1H-isoindol-5-yl)methyl)-2,3-dihydrofuro[3,2-b]pyridine-5-carboxylate The title compound was obtained by a method similar to that in step A of Example 102.
MS: [M+H]$^+$ 339.4.

E) 7-((2-methyl-1-oxo-2,3-dihydro-1H-isoindol-5-yl)methyl)-2,3-dihydrofuro[3,2-b]pyridine-5-carboxylic acid The title compound was obtained by a method similar to that in step B of Example 31.
MS: [M+H]$^+$ 325.3.

F) 1,5-anhydro-2,3-dideoxy-3-(((7-((2-methyl-1-oxo-2,3-dihydro-1H-isoindol-5-yl)methyl)-2,3-dihydrofuro[3,2-b]pyridin-5-yl)carbonyl)amino)-L-threo-pentitol The title compound was obtained by a method similar to that in Example 22.
$^1$H NMR (400 MHz, DMSO-d$_6$) δ 1.59 (1H, qd, J=12.3, 4.4 Hz), 1.80 (1H, dd, J=13.2, 4.4 Hz), 2.98-3.05 (4H, m), 3.26-3.31 (1H, m), 3.33-3.38 (2H, m), 3.55 (1H, d, J=5.1 Hz), 3.77 (3H, td, J=10.8, 4.4 Hz), 4.04 (2H, s), 4.42 (2H, s), 4.75 (2H, t, J=8.9 Hz), 4.92 (1H, d, J=5.6 Hz), 7.35 (1H, d, J=8.1 Hz), 7.43 (1H, s), 7.59 (1H, d, J=7.8 Hz), 7.67 (1H, s), 8.26 (1H, d, J=8.1 Hz).

The compounds of Examples are shown in the following Tables. In the Tables, MS means measured values. The compounds of Examples 2, 3, 6, 7, 9, 11, 13, 15, 17, 19, 21, 23, 24, 28, 30, 32, 34, 41, 47, 48, 50, 59, 61, 69-73, 75, 78-94, 97, 98, 100, 101, 103-108 and 110 in the following Tables were produced by the methods shown in the above-mentioned Examples or a method analogous thereto.

TABLE 1

| Ex. No. | IUPAC name | structural formula | salt | MS |
|---|---|---|---|---|
| 1 | N-((1S,2S)-2-hydroxycyclopentyl)-7-(4-(1H-pyrazol-1-yl)benzyl)-2,3-dihydrofuro[3,2-b]pyridine-5-carboxamide | | | 405.2 |
| 2 | N-((1S,2S)-2-hydroxycyclohexyl)-7-(4-(1H-pyrazol-1-yl)benzyl)-2,3-dihydrofuro[3,2-b]pyridine-5-carboxamide | | | 419.2 |

TABLE 1-continued

| Ex. No. | IUPAC name | structural formula | salt | MS |
|---|---|---|---|---|
| 3 | 1,5-anhydro-2,4-dideoxy-2-(((7-(4-(1H-pyrazol-1-yl)benzyl)-2,3-dihydrofuro[3,2-b]pyridin-5-yl)carbonyl)amino)-L-threo-pentitol | | | 421.2 |
| 4 | N-(1S,2S)-2-hydroxycyclohexyl)-7-(4-(1H-pyrazol-1-yl)benzyl)furo[3,2-b]pyridine-5-carboxamide | | | 417.2 |
| 5 | N-((1S,2S)-2-hydroxycyclohexyl)-7-(4-(1-methyl-1H-pyrazol-3-yl)benzyl)furo[3,2-b]pyridine-5-carboxamide | | | 431.2 |
| 6 | 1,5-anhydro-2,4-dideoxy-2-(((7-(4-(1H-pyrazol-1-yl)benzyl)furo[3,2-b]pyridin-5-yl)carbonyl)amino)-L-threo-pentitol | | | 419.1 |

TABLE 1-continued

| Ex. No. | IUPAC name | structural formula | salt | MS |
|---|---|---|---|---|
| 7 | 1,5-anhydro-2,4-dideoxy-2-(((7-(4-(1-methyl-1H-pyrazol-3-yl)benzyl)furo[3,2-b]pyridin-5-yl)carbonyl)amino)-L-threo-pentitol | | | 433.1 |
| 8 | 1,5-anhydro-2,4-dideoxy-2-(((7-(4-(1-methyl-1H-pyrazol-3-yl)benzyl)-2,3-dihydrofuro[3,2-b]pyridin-5-yl)carbonyl)amino)-L-threo-pentitol | | | 435.2 |
| 9 | N-((1S,2S)-2-hydroxycyclohexyl)-7-(4-(1-methyl-1H-pyrazol-3-yl)benzyl)-2,3-dihydrofuro[3,2-b]pyridine-5-carboxamide | | | 433.2 |

TABLE 1-continued

| Ex. No. | IUPAC name | structural formula | salt | MS |
|---|---|---|---|---|
| 10 | N-((1S,2S)-2-hydroxycyclohexyl)-7-((6-methoxypyridin-3-yl)methyl)-2,3-dihydrofuro[3,2-b]pyridine-5-carboxamide | | | 384.3 |
| 11 | N-((1S,2S)-2-hydroxycyclopentyl)-7-((6-methoxypyridin-3-yl)methyl)-2,3-dihydrofuro[3,2-b]pyridine-5-carboxamide | | | 370.3 |
| 12 | N-((1S,2S)-2-hydroxycyclohexyl)-7-(4-methoxybenzyl)-2,3-dihydrofuro[3,2-b]pyridine-5-carboxamide | | | 383.2 |
| 13 | N-((1S,2S)-2-hydroxycyclopentyl)-7-(4-methoxybenzyl)-2,3-dihydrofuro[3,2-b]pyridine-5-carboxamide | | | 369.2 |

TABLE 1-continued

| Ex. No. | IUPAC name | structural formula | salt | MS |
|---|---|---|---|---|
| 14 | N-((1S,2S)-2-hydroxycyclohexyl)-7-(4-(5-methyl-1,3-thiazol-2-yl)benzyl)-2,3-dihydrofuro[3,2-b]pyridine-5-carboxamide | | | 450.2 |
| 15 | N-((1S,2S)-2-hydroxycyclopentyl)-7-(4-(5-methyl-1,3-thiazol-2-yl)benzyl)-2,3-dihydrofuro[3,2-b]pyridine-5-carboxamide | | | 436.2 |
| 16 | N-((1S,2S)-2-hydroxycyclohexyl)-7-(4-(4-methyl-1,3-thiazol-2-yl)benzyl)-2,3-dihydrofuro[3,2-b]pyridine-5-carboxamide | | | 450.2 |

TABLE 1-continued

| Ex. No. | IUPAC name | structural formula | salt | MS |
|---|---|---|---|---|
| 17 | N-((1S,2S)-2-hydroxycyclopentyl)-7-(4-(4-methyl-1,3-thiazol-2-yl)benzyl)-2,3-dihydrofuro[3,2-b]pyridine-5-carboxamide | | | 436.2 |
| 18 | N-((1S,2S)-2-hydroxycyclohexyl)-7-(4-(2-methyl-1,3-thiazol-5-yl)benzyl)-2,3-dihydrofuro[3,2-b]pyridine-5-carboxamide | | | 450.2 |
| 19 | N-((1S,2S)-2-hydroxycyclopentyl)-7-(4-(2-methyl-1,3-thiazol-5-yl)benzyl)-2,3-dihydrofuro[3,2-b]pyridine-5-carboxamide | | | 436.2 |

TABLE 1-continued

| Ex. No. | IUPAC name | structural formula | salt | MS |
|---|---|---|---|---|
| 20 | 1,5-anhydro-2,3-dideoxy-3-(((7-(4-(1-methyl-1H-1,2,3-triazol-4-yl)benzyl)furo[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-1,2,3-triazol-4-yl)benzyl)furo[3,2-b]pyridine-5-carboxamide | | | 434.1 |
| 21 | 1,5-anhydro-2,4-dideoxy-2-(((7-(4-(1-methyl-1H-1,2,3-triazol-4-yl)benzyl)furo[3,2-b]pyridin-5-yl)carbonyl)amino)-L-threo-pentitol | | | 434.1 |
| 22 | 1,5-anhydro-2,3-dideoxy-3-(((7-(4-(1H-pyrazol-1-yl)benzyl)-2,3-dihydrofuro[3,2-b]pyridin-5-yl)carbonyl)amino)-L-threo-pentitol (synonym) 7-(4-(1H-pyrazol-1-yl)benzyl)-N-((3R,4S)-3-hydroxytetrahydro-2H-pyran-4-yl)-2,3-dihydrofuro[3,2-b]pyridine-5-carboxamide | | | 421.2 |

TABLE 1-continued

| Ex. No. | IUPAC name | structural formula | salt | MS |
|---|---|---|---|---|
| 23 | N-((1S,2S)-2-hydroxycyclohexyl)-7-(4-(1-methyl-1H-1,2,3-triazol-4-yl)benzyl)furo[3,2-b]pyridine-5-carboxamide | | | 432.2 |
| 24 | N-(trans-5,5-difluoro-2-hydroxycyclohexyl)-7-(4-(1H-pyrazol-1-yl)benzyl)furo[3,2-b]pyridine-5-carboxamide | | | 453.2 |
| 25 | N-(trans-5,5-difluoro-2-hydroxycyclohexyl)-7-(4-(1H-pyrazol-1-yl)benzyl)-2,3-dihydrofuro[3,2-b]pyridine-5-carboxamide | | | 455.2 |

TABLE 1-continued

| Ex. No. | IUPAC name | structural formula | salt | MS |
|---|---|---|---|---|
| 26 | N-(trans-5,5-difluoro-2-hydroxycyclohexyl)-7-(4-(1H-pyrazol-1-yl)benzyl)-2,3-dihydrofuro[3,2-b]pyridine-5-carboxamide (optical isomer: retention time short) | | | 455.2 |
| 27 | N-(trans-5,5-difluoro-2-hydroxycyclohexyl)-7-(4-(1H-pyrazol-1-yl)benzyl)-2,3-dihydrofuro[3,2-b]pyridine-5-carboxamide (optical isomer: retention time long) | | | 455.2 |
| 28 | 1,5-anhydro-2,3-dideoxy-3-(((7-(4-(1-methyl-1H-pyrazol-3-yl)benzyl)-2,3-dihydrofuro[3,2-b]pyridin-5-yl)carbonyl)amino)-L-threo-pentitol | | | 435.2 |

TABLE 1-continued

| Ex. No. | IUPAC name | structural formula | salt | MS |
|---|---|---|---|---|
| 29 | 1,5-anhydro-2,3-dideoxy-3-(((7-((6-(1-methyl-1H-pyrazol-3-yl)pyridin-3-yl)methyl)-2,3-dihydrofuro[3,2-b]pyridin-5-yl)carbonyl)amino)-L-threo-pentitol | | | 436.2 |
| 30 | N-(2-hydroxycyclobutyl)-7-(4-(1H-pyrazol-1-yl)benzyl)-2,3-dihydrofuro[3,2-b]pyridine-5-carboxamide | | | 391.2 |
| 31 | 1,5-anhydro-2,3-dideoxy-3-(((7-(4-(1-methyl-1H-1,2,3-triazol-4-yl)benzyl)-2,3-dihydrofuro[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-1,2,3-triazol-4-yl)benzyl)-2,3-dihydrofuro[3,2-b]pyridine-5-carboxamide | | | 436.2 |

TABLE 1-continued

| Ex. No. | IUPAC name | structural formula | salt | MS |
|---|---|---|---|---|
| 32 | N-((1S,2S)-2-hydroxycyclohexyl)-7-((6-(1-methyl-1H-pyrazol-3-yl)pyridin-3-yl)methyl)-2,3-dihydrofuro[3,2-b]pyridine-5-carboxamide | | | 434.2 |
| 33 | N-((1S,2S)-2-hydroxycyclohexyl)-7-((6-(1-methyl-1H-1,2,3-triazol-4-yl)pyridin-3-yl)methyl)furo[3,2-b]pyridine-5-carboxamide | | | 433.2 |
| 34 | 1,5-anhydro-2,3-dideoxy-3-(((7-((6-(1-methyl-1H-1,2,3-triazol-4-yl)pyridin-3-yl)methyl)furo[3,2-b]pyridin-5-yl)carbonyl)amino)-L-threo-pentitol | | | 435.2 |

TABLE 1-continued

| Ex. No. | IUPAC name | structural formula | salt | MS |
|---|---|---|---|---|
| 35 | N-((1S,2S)-2-hydroxycyclohexyl)-7-((6-(1-methyl-1H-pyrazol-4-yl)pyridin-3-yl)methyl)furo[3,2-b]pyridine-5-carboxamide | | | 432.2 |
| 36 | 1,5-anhydro-2,3-dideoxy-3-(((7-((6-(1-methyl-1H-pyrazol-4-yl)pyridin-3-yl)methyl)furo[3,2-b]pyridin-5-yl)carbonyl)amino)-L-threo-pentitol (synonym) N-((3R,4S)-3-hydroxytetrahydro-2H-pyran-4-yl)-7-((6-(1-methyl-1H-pyrazol-4-yl)pyridin-3-yl)methyl)furo[3,2-b]pyridine-5-carboxamide | | | 434.1 |
| 37 | 1,5-anhydro-2,3-dideoxy-3-(((7-((6-methoxypyridin-3-yl)methyl)furo[3,2-b]pyridin-5-yl)carbonyl)amino)-L-threo-pentitol | | | 384.2 |
| 38 | 1,5-anhydro-2,3-dideoxy-3-(((7-((6-oxo-1,6-dihydropyridin-3-yl)methyl)furo[3,2-b]pyridin-5-yl)carbonyl)amino)-L-threo-pentitol | | | 370.2 |

TABLE 1-continued

| Ex. No. | IUPAC name | structural formula | salt | MS |
|---|---|---|---|---|
| 39 | 1,5-anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol | | | 452.2 |
| 40 | 1,5-anhydro-2,3-dideoxy-3-(((7-(4-(1-methyl-1H-pyrazol-4-yl)benzyl)furo[3,2-b]pyridin-5-yl)carbonyl)amino)-L-threo-pentitol | | | 433.2 |
| 41 | 1,5-anhydro-2,4-dideoxy-2-(((7-(4-(1-methyl-1H-pyrazol-4-yl)benzyl)furo[3,2-b]pyridin-5-yl)carbonyl)amino)-L-threo-pentitol | | | 433.2 |

TABLE 1-continued

| Ex. No. | IUPAC name | structural formula | salt | MS |
|---|---|---|---|---|
| 42 | N-(trans-4,4-difluoro-2-hydroxycyclohexyl)-7-(4-(1H-pyrazol-1-yl)benzyl)-2,3-dihydrofuro[3,2-b]pyridine-5-carboxamide | | | 455.2 |
| 43 | 1,5-anhydro-2,3-dideoxy-3-(((7-(4-(6-methylpyridazin-4-yl)benzyl)furo[3,2-b]pyridin-5-yl)carbonyl)amino)-L-threo-pentitol | | | 445.2 |
| 44 | 1,5-anhydro-2,3-dideoxy-3-(((7-(4-(1-methyl-1H-pyrazol-4-yl)benzyl)-2,3-dihydrofuro[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-pyrazol-4-yl)benzyl)-2,3-dihydrofuro[3,2-b]pyridine-5-carboxamide | | | 435.2 |

TABLE 1-continued

| Ex. No. | IUPAC name | structural formula | salt | MS |
|---|---|---|---|---|
| 45 | N-(trans-4,4-difluoro-2-hydroxycyclohexyl)-7-(4-(1H-pyrazol-1-yl)benzyl)-2,3-dihydrofuro[3,2-b]pyridine-5-carboxamide (optical isomer: retention time short) | | | 455.2 |
| 46 | N-(trans-4,4-difluoro-2-hydroxycyclohexyl)-7-(4-(1H-pyrazol-1-yl)benzyl)-2,3-dihydrofuro[3,2-b]pyridine-5-carboxamide (optical isomer: retention time long) | | | 455.2 |
| 47 | N-((1S,2S)-2-hydroxycyclohexyl)-7-(4-(1-methyl-1H-1,2,3-triazol-4-yl)benzyl)-2,3-dihydrofuro[3,2-b]pyridine-5-carboxamide | | | 434.2 |

TABLE 1-continued

| Ex. No. | IUPAC name | structural formula | salt | MS |
|---|---|---|---|---|
| 48 | 1,5-anhydro-2,3-dideoxy-3-(((7-(4-(1H-pyrazol-1-yl)benzyl)furo[3,2-b]pyridin-5-yl)carbonyl)amino)-L-threo-pentitol | | | 419.2 |
| 49 | 1,5-anhydro-2,3-dideoxy-3-(((7-(4-(2-methylpyrimidin-4-yl)benzyl)furo[3,2-b]pyridin-5-yl)carbonyl)amino)-L-threo-pentitol | | | 445.2 |
| 50 | N-((1S,2S)-2-hydroxycyclohexyl)-7-(4-(2-methylpyrimidin-4-yl)benzyl)furo[3,2-b]pyridine-5-carboxamide | | | 443.3 |

TABLE 1-continued

| Ex. No. | IUPAC name | structural formula | salt | MS |
|---|---|---|---|---|
| 51 | 1,5-anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol (stereoisomer: retention time short) | | | 452.2 |
| 52 | 1,5-anhydro-2,3-dideoxy-3-(((7-(fluoro(6-(1-methyl-1H-pyrazol-4-yl)pyridin-3-yl)methyl)furo[3,2-b]pyridin-5-yl)carbonyl)amino)-L-threo-pentitol (stereoisomer: retention time long) | | | 452.2 |
| 53 | 1,5-anhydro-2,3-dideoxy-3-(((7-(fluoro(4-(1-methyl-1H-1,2,3-triazol-4-yl)phenyl)methyl)furo[3,2-b]pyridin-5-yl)carbonyl)amino)-L-threo-pentitol | | | 452.2 |

TABLE 1-continued

| Ex. No. | IUPAC name | structural formula | salt | MS |
|---|---|---|---|---|
| 54 | 7-(fluoro(4-(1-methyl-1H-1,2,3-triazol-4-yl)phenyl)methyl)-N-((1S,2S)-2-hydroxycyclohexyl)furo[3,2-b]pyridine-5-carboxamide | | | 450.2 |
| 55 | 1,5-anhydro-2,3-dideoxy-3-(((7-(fluoro(4-(1-methyl-1H-1,2,3-triazol-4-yl)phenyl)methyl)furo[3,2-b]pyridin-5-yl)carbonyl)amino)-L-threo-pentitol (stereoisomer: retention time short) (synonym) 7-(fluoro(4-(1-methyl-1H-1,2,3-triazol-4-yl)phenyl)methyl)-N-((3R,4S)-3-hydroxytetrahydro-2H-pyran-4-yl)furo[3,2-b]pyridine-5-carboxamide (stereoisomer: retention time short) | | | 452.2 |
| 56 | 1,5-anhydro-2,3-dideoxy-3-(((7-(fluoro(4-(1-methyl-1H-1,2,3-triazol-4-yl)phenyl)methyl)furo[3,2-b]pyridin-5-yl)carbonyl)amino)-L-threo-pentitol (stereoisomer: retention time long) | | | 452.2 |

TABLE 1-continued

| Ex. No. | IUPAC name | structural formula | salt | MS |
|---|---|---|---|---|
| 57 | 7-(fluoro(4-(1-methyl-1H-1,2,3-triazol-4-yl)phenyl)methyl)-N-((1S,2S)-2-hydroxycyclohexyl)furo[3,2-b]pyridine-5-carboxamide (stereoisomer: retention time short) | 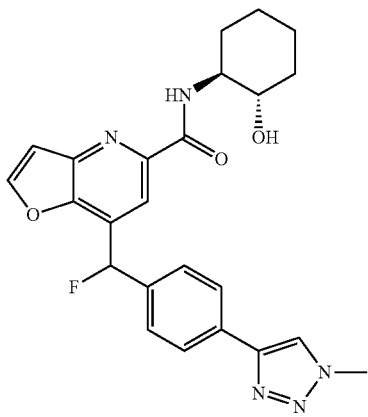 | | 450.2 |
| 58 | 7-(fluoro(4-(1-methyl-1H-1,2,3-triazol-4-yl)phenyl)methyl)-N-((1S,2S)-2-hydroxycyclohexyl)furo[3,2-b]pyridine-5-carboxamide (stereoisomer: retention time long) | 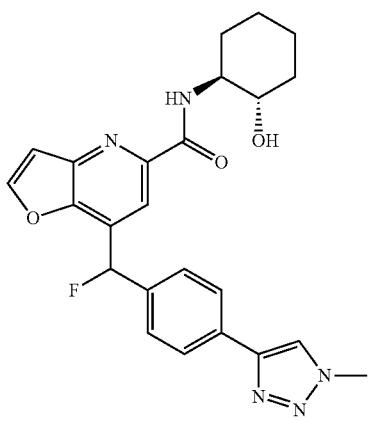 [SMILES: Cn1cc(-c2ccc(C(F)c3cc(C(=O)N[C@H]4CCCC[C@@H]4O)nc4ccoc34)cc2)nn1] | | 450.2 |
| 59 | 1,5-anhydro-2,3-dideoxy-3-(((7-(4-(1-methyl-1H-1,2,3-triazol-4-yl)benzyl)-2,3-dihydrofuro[3,2-b]pyridin-5-yl)carbonyl)amino)-D-threo-pentitol | 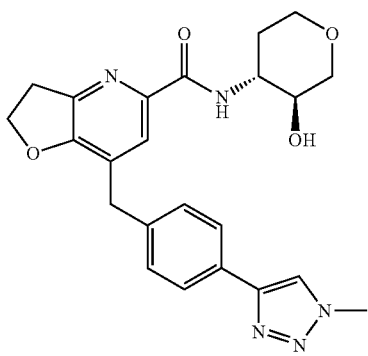 [SMILES: Cn1cc(-c2ccc(Cc3cc(C(=O)N[C@@H]4CCOC[C@H]4O)nc4c3OCC4)cc2)nn1] | | 436.2 |

TABLE 1-continued

| Ex. No. | IUPAC name | structural formula | salt | MS |
|---|---|---|---|---|
| 60 | 1,5-anhydro-2,3-dideoxy-3-(((7-((6-(1-methyl-1H-pyrazol-4-yl)pyridin-3-yl)methyl)-2,3-dihydrofuro[3,2-b]pyridin-5-yl)carbonyl)amino)-L-threo-pentitol | | | 436.2 |
| 61 | N-((1S,2S)-2-hydroxycyclohexyl)-7-((6-(1-methyl-1H-pyrazol-4-yl)pyridin-3-yl)methyl)-2,3-dihydrofuro[3,2-b]pyridine-5-carboxamide | | | 434.1 |
| 62 | 1,5-anhydro-2,3-dideoxy-3-(((7-(3-fluoro-4-(methylcarbamoyl)benzyl)furo[3,2-b]pyridin-5-yl)carbonyl)amino)-L-threo-pentitol | | | 428.1 |

TABLE 1-continued

| Ex. No. | IUPAC name | structural formula | salt | MS |
|---|---|---|---|---|
| 63 | 1,5-anhydro-2,3-dideoxy-3-(((7-(3-fluoro-4-(methylcarbamoyl)benzyl)-2,3-dihydrofuro[3,2-b]pyridin-5-yl)carbonyl)amino)-L-threo-pentitol | | | 430.1 |
| 64 | 1,5-anhydro-2,3-dideoxy-3-(((2-methyl-7-(4-(1-methyl-1H-1,2,3-triazol-4-yl)benzyl)furo[3,2-b]pyridin-5-yl)carbonyl)amino)-L-threo-pentitol | | | 448.1 |
| 65 | 1,5-anhydro-2,3-dideoxy-3-(((7-(3-fluoro-4-(methylcarbamoyl)benzyl)-2-methylfuro[3,2-b]pyridin-5-yl)carbonyl)amino)-L-threo-pentitol | | | 442.1 |

TABLE 1-continued

| Ex. No. | IUPAC name | structural formula | salt | MS |
|---|---|---|---|---|
| 66 | 1,5-anhydro-2,3-dideoxy-3-(((2-methyl-7-(4-(1-methyl-1H-pyrazol-4-yl)benzyl)furo[3,2-b]pyridin-5-yl)carbonyl)amino)-L-threo-pentitol | | | 447.1 |
| 67 | 1,5-anhydro-2,3-dideoxy-3-(((2-methyl-7-(4-(1H-pyrazol-1-yl)benzyl)furo[3,2-b]pyridin-5-yl)carbonyl)amino)-L-threo-pentitol | | | 433.1 |
| 68 | 1,5-anhydro-2,3-dideoxy-3-(((2-methyl-7-((6-(1-methyl-1H-1,2,3-triazol-4-yl)pyridin-3-yl)methyl)furo[3,2-b]pyridin-5-yl)carbonyl)amino)-L-threo-pentitol | | | 449.1 |

TABLE 1-continued

| Ex. No. | IUPAC name | structural formula | salt | MS |
|---|---|---|---|---|
| 69 | 7-(fluoro(6-(1-methyl-1H-pyrazol-4-yl)pyridin-3-yl)methyl)-N-((1S,2S)-2-hydroxycyclohexyl)furo[3,2-b]pyridine-5-carboxamide | | | 450.1 |
| 70 | 7-(fluoro(6-(1-methyl-1H-pyrazol-4-yl)pyridin-3-yl)methyl)-N-((1S,2S)-2-hydroxycyclohexyl)furo[3,2-b]pyridine-5-carboxamide | | | 450.1 |
| 71 | 1,5-anhydro-2,3-dideoxy-3-(((7-(4-(1-methyl-1H-1,2,3-triazol-4-yl)benzyl)furo[3,2-b]pyridin-5-yl)carbonyl)amino)-D-threo-pentitol | | | 434.1 |
| 72 | 7-(3-fluoro-4-(methylcarbamoyl)benzyl)-N-((1S,2S)-2-hydroxycyclopentyl)-2,3-dihydrofuro[3,2-b]pyridine-5-carboxamide | | | 414.2 |

TABLE 1-continued

| Ex. No. | IUPAC name | structural formula | salt | MS |
|---|---|---|---|---|
| 73 | 7-(3-fluoro-4-(methylcarbamoyl)benzyl)-N-((1S,2S)-2-hydroxycyclohexyl)-2,3-dihydrofuro[3,2-b]pyridine-5-carboxamide | | | 428.2 |
| 74 | 1,5-anhydro-2,3-dideoxy-3-(((7-(4-(1-methyl-1H-imidazol-4-yl)benzyl)-2,3-dihydrofuro[3,2-b]pyridin-5-yl)carbonyl)amino)-L-threo-pentitol (synonym) N-((3R,4S)-3-hydroxytetrahydro-2H-pyran-4-yl)-7-(4-(1-methyl-1H-imidazol-4-yl)benzyl)-2,3-dihydrofuro[3,2-b]pyridine-5-carboxamide | | | 435.1 |
| 75 | N-(1S,2S)-2-hydroxycyclohexyl)-7-(4-(1-methyl-1H-imidazol-4-yl)benzyl)-2,3-dihydrofuro[3,2-b]pyridine-5-carboxamide | | | 433.1 |
| 76 | 1,5-anhydro-2,3-dideoxy-3-(((7-(3-fluoro-4-((2-methoxyethyl)carbamoyl)benzyl)-2,3-dihydrofuro[3,2-b]pyridin-5-yl)carbonyl)amino)-L-threo-pentitol (synonym) 7-(3-fluoro-4-((2-methoxyethyl)carbamoyl)benzyl)-N-((3R,4S)-3-hydroxytetrahydro-2H-pyran-4-yl)-2,3-dihydrofuro[3,2-b]pyridine-5-carboxamide | | | 474.1 |

TABLE 1-continued

| Ex. No. | IUPAC name | structural formula | salt | MS |
|---|---|---|---|---|
| 77 | 1,5-anhydro-2,3-dideoxy-3-(((7-(3-fluoro-4-(((2S)-tetrahydrofuran-2-ylmethyl)carbamoyl)benzyl)-2,3-dihydrofuro[3,2-b]pyridin-5-yl)carbonyl)amino)-L-threo-pentitol (synonym) 7-(3-fluoro-4-((((S)-tetrahydrofuran-2-yl)methyl)carbamoyl)benzyl)-N-((3R,4S)-3-hydroxytetrahydro-2H-pyran-4-yl)-2,3-dihydrofuro[3,2-b]pyridine-5-carboxamide | | | 500.2 |
| 78 | 1,5-anhydro-3-(((7-(4-((cyclopropylmethyl)carbamoyl)-3-fluorobenzyl)-2,3-dihydrofuro[3,2-b]pyridin-5-yl)carbonyl)amino)-2,3-dideoxy-L-threo-pentitol | | | 470.2 |
| 79 | 1,5-anhydro-3-(((7-(4-((cyclopentylmethyl)carbamoyl)-3-fluorobenzyl)-2,3-dihydrofuro[3,2-b]pyridin-5-yl)carbonyl)amino)-2,3-dideoxy-L-threo-pentitol | | | 498.2 |
| 80 | 1,5-anhydro-3-(((7-(4-(butylcarbamoyl)-3-fluorobenzyl)-2,3-dihydrofuro[3,2-b]pyridin-5-yl)carbonyl)amino)-2,3-dideoxy-L-threo-pentitol | | | 472.2 |

TABLE 1-continued

| Ex. No. | IUPAC name | structural formula | salt | MS |
|---|---|---|---|---|
| 81 | 1,5-anhydro-2,3-dideoxy-3-(((7-(4-(ethylcarbamoyl)-3-fluorobenzyl)-2,3-dihydrofuro[3,2-b]pyridin-5-yl)carbonyl)amino)-L-threo-pentitol | | | 444.2 |
| 82 | 1,5-anhydro-3-(((7-(4-(cyclopropylcarbamoyl)-3-fluorobenzyl)-2,3-dihydrofuro[3,2-b]pyridin-5-yl)carbonyl)amino)-2,3-dideoxy-L-threo-pentitol | | | 456.2 |
| 83 | 1,5-anhydro-2,3-dideoxy-3-(((7-(3-fluoro-4-(isopropylcarbamoyl)benzyl)-2,3-dihydrofuro[3,2-b]pyridin-5-yl)carbonyl)amino)-L-threo-pentitol | | | 458 |
| 84 | 1,5-anhydro-2,3-dideoxy-3-(((7-(3-fluoro-4-(propylcarbamoyl)benzyl)-2,3-dihydrofuro[3,2-b]pyridin-5-yl)carbonyl)amino)-L-threo-pentitol | | | 458.2 |

TABLE 1-continued

| Ex. No. | IUPAC name | structural formula | salt | MS |
|---|---|---|---|---|
| 85 | 1,5-anhydro-2,3-dideoxy-3-(((7-(3-fluoro-4-(isobutylcarbamoyl)benzyl)-2,3-dihydrofuro[3,2-b]pyridin-5-yl)carbonyl)amino)-L-threo-pentitol | | | 472.2 |
| 86 | 1,5-anhydro-2,3-dideoxy-3-(((7-(4-((2-ethoxyethyl)carbamoyl)-3-fluorobenzyl)-2,3-dihydrofuro[3,2-b]pyridin-5-yl)carbonyl)amino)-L-threo-pentitol | | | 488.2 |
| 87 | 1,5-anhydro-2,3-dideoxy-3-(((7-(3-fluoro-4-((3-methoxypropyl)carbamoyl)benzyl)-2,3-dihydrofuro[3,2-b]pyridin-5-yl)carbonyl)amino)-L-threo-pentitol | | | 488.2 |
| 88 | 1,5-anhydro-2,3-dideoxy-3-(((7-(3-fluoro-4-(((2R)-tetrahydrofuran-2-ylmethyl)carbamoyl)benzyl)-2,3-dihydrofuro[3,2-b]pyridin-5-yl)carbonyl)amino)-L-threo-pentitol | | | 500.3 |

TABLE 1-continued

| Ex. No. | IUPAC name | structural formula | salt | MS |
|---|---|---|---|---|
| 89 | 1,5-anhydro-3-(((7-(4-((2-tert-butoxy ethyl)carbamoyl)-3-fluorobenzyl)-2,3-dihydrofuro[3,2-b]pyridin-5-yl)carbonyl)amino)-2,3-dideoxy-L-threo-pentitol | | | 514 |
| 90 | 1,5-anhydro-2,3-dideoxy-3-(((7-(3-fluoro-4-((4-hydroxybenzyl)carbamoyl)benzyl)-2,3-dihydrofuro[3,2-b]pyridin-5-yl)carbonyl)amino)-L-threo-pentitol | | | 522.2 |
| 91 | 1,5-anhydro-2,3-dideoxy-3-(((7-(3-fluoro-4-((3-hydroxybenzyl)carbamoyl)benzyl)-2,3-dihydrofuro[3,2-b]pyridin-5-yl)carbonyl)amino)-L-threo-pentitol | | | 522.2 |
| 92 | 1,5-anhydro-2,3-dideoxy-3-(((7-(3-fluoro-4-((4-hydroxyphenyl)carbamoyl)benzyl)-2,3-dihydrofuro[3,2-b]pyridin-5-yl)carbonyl)amino)-L-threo-pentitol | | | 507.9 |

TABLE 1-continued

| Ex. No. | IUPAC name | structural formula | salt | MS |
|---|---|---|---|---|
| 93 | 1,5-anhydro-2,3-dideoxy-3-(((7-(3-fluoro-4-((1-methoxypropan-2-yl)carbamoyl)benzyl)-2,3-dihydrofuro[3,2-b]pyridin-5-yl)carbonyl)amino)-L-threo-pentitol | | | 488.0 |
| 94 | 1,5-anhydro-2,3-dideoxy-3-(((7-(3-fluoro-4-(pentylcarbamoyl)benzyl)-2,3-dihydrofuro[3,2-b]pyridin-5-yl)carbonyl)amino)-L-threo-pentitol | | | 486 |
| 95 | methyl ((2-fluoro-4-((5-(((3R,4S)-3-hydroxytetrahydro-2H-pyran-4-yl)carbamoyl)-2,3-dihydrofuro[3,2-b]pyridin-7-yl)methyl)benzoyl)amino)acetate | | | 488.2 |
| 96 | ((2-fluoro-4-((5-(((3R,4S)-3-hydroxytetrahydro-2H-pyran-4-yl)carbamoyl)-2,3-dihydrofuro[3,2-b]pyridin-7-yl)methyl)benzoyl)amino)acetic acid | | | 474.2 |

TABLE 1-continued

| Ex. No. | IUPAC name | structural formula | salt | MS |
|---|---|---|---|---|
| 97 | 1,5-anhydro-2,3-dideoxy-3-(((7-(3-fluoro-4-((2-(isopropylsulfanyl)ethyl)-carbamoyl)benzyl)-2,3-dihydrofuro[3,2-b]pyridin-5-yl)carbonyl)amino)-L-threo-pentitol | | | 518.2 |
| 98 | 1,5-anhydro-3-(((7-(4-((2-(tert-butylsulfanyl)ethyl)carbamoyl)-3-fluorobenzyl)-2,3-dihydrofuro[3,2-b]pyridin-5-yl)carbonyl)amino)-2,3-dideoxy-L-threo-pentitol | | | 532.4 |
| 99 | 1,5-anhydro-2,3-dideoxy-3-(((7-(4-((2-(diethylamino)-2-oxoethyl)carbamoyl)-3-fluorobenzyl)-2,3-dihydrofuro[3,2-b]pyridin-5-yl)carbonyl)amino)-L-threo-pentitol | | | 529.2 |

TABLE 1-continued

| Ex. No. | IUPAC name | structural formula | salt | MS |
|---|---|---|---|---|
| 100 | 1,5-anhydro-2,3-dideoxy-3-(((7-(4-((2-(dimethylamino)-2-oxoethyl)carbamoyl)-3-fluorobenzyl)-2,3-dihydrofuro[3,2-b]pyridin-5-yl)carbonyl)amino)-L-threo-pentitol | | | 501.2 |
| 101 | 1,5-anhydro-2,3-dideoxy-3-(((7-(3-fluoro-4-((2-oxo-2-(pyrrolidin-1-yl)ethyl)carbamoyl)benzyl)-2,3-dihydrofuro[3,2-b]pyridin-5-yl)carbonyl)amino)-L-threo-pentitol | | | 527.3 |
| 102 | 1,5-anhydro-2,3-dideoxy-3-(((7-(3-fluoro-4-(((2S)-tetrahydrofuran-2-ylmethyl)carbamoyl)benzyl)-furo[3,2-b]pyridin-5-yl)carbonyl)amino)-L-threo-pentitol (synonym) 7-(3-fluoro-4-((((S)-tetrahydrofuran-2-yl)methyl)carbamoyl)benzyl)-N-((3R,4S)-3-hydroxytetrahydro-2H-pyran-4-yl)furo[3,2-b]pyridine-5-carboxamide | | | 498.2 |

TABLE 1-continued

| Ex. No. | IUPAC name | structural formula | salt | MS |
|---|---|---|---|---|
| 103 | 1,5-anhydro-2,3-dideoxy-3-(((7-(3-fluoro-4-(propylcarbamoyl)benzyl)furo[3,2-b]pyridin-5-yl)carbonyl)amino)-L-threo-pentitol | | | 456.2 |
| 104 | 1,5-anhydro-2,3-dideoxy-3-(((7-(3-fluoro-4-((3-methoxypropyl)carbamoyl)-benzyl)furo[3,2-b]pyridin-5-yl)carbonyl)amino)-L-threo-pentitol | | | 486.2 |
| 105 | 1,5-anhydro-2,3-dideoxy-3-(((7-(3-fluoro-4-(((2R)-tetrahydrofuran-2-ylmethyl)carbamoyl)benzyl)-furo[3,2-b]pyridin-5-yl)carbonyl)amino)-L-threo-pentitol | | | 498.2 |
| 106 | 1,5-anhydro-3-(((7-(4-(cyclopropylcarbamoyl)-3-fluorobenzyl)furo[3,2-b]pyridin-5-yl)carbonyl)amino)-2,3-dideoxy-L-threo-pentitol | | | 454.2 |

TABLE 1-continued

| Ex. No. | IUPAC name | structural formula | salt | MS |
|---|---|---|---|---|
| 107 | 1,5-anhydro-2,3-dideoxy-3-(((7-(4-((2-ethoxyethyl)carbamoyl)-3-fluorobenzyl)furo[3,2-b]pyridin-5-yl)carbonyl)amino)-L-threo-pentitol | 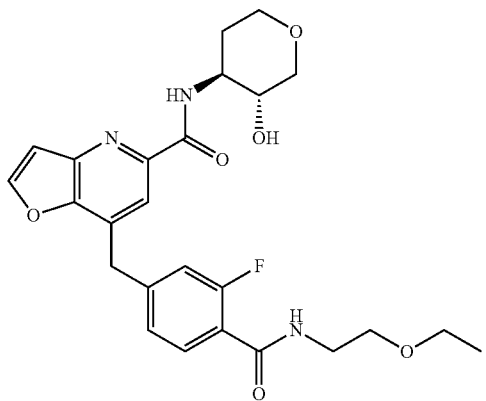 [SMILES: CCOCCNC(=O)c1ccc(Cc2cc(C(=O)N[C@H]3CCOC[C@@H]3O)nc3ccoc23)cc1F] | | 486.2 |
| 108 | 1,5-anhydro-2,3-dideoxy-3-(((7-(3-fluoro-4-((tetrahydro-2H-pyran-2-ylmethyl)carbamoyl)benzyl)-furo[3,2-b]pyridin-5-yl)carbonyl)amino)-L-threo-pentitol | 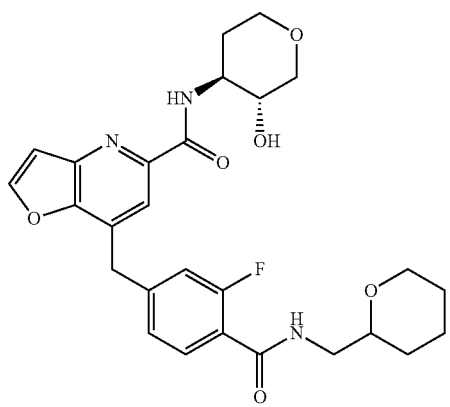 [SMILES: O=C(N[C@H]1CCOC[C@@H]1O)c1cc(Cc2ccc(C(=O)NCC3CCCCO3)c(F)c2)c2occc2n1] | | 512.3 |
| 109 | 1,5-anhydro-2,3-dideoxy-3-(((7-(3-fluoro-4-((2-methoxyethyl)carbamoyl)benzyl)-furo[3,2-b]pyridin-5-yl)carbonyl)amino)-L-threo-pentitol (synonym) 7-(3-fluoro-4-((2-methoxyethyl)carbamoyl)benzyl)-N-((3R,4S)-3-hydroxytetrahydro-2H-pyran-4-yl)furo[3,2-b]pyridine-5-carboxamide | 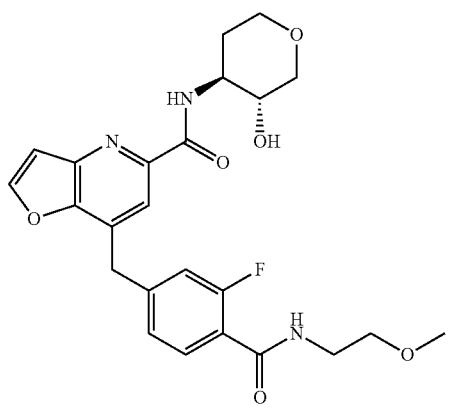 [SMILES: COCCNC(=O)c1ccc(Cc2cc(C(=O)N[C@H]3CCOC[C@@H]3O)nc3ccoc23)cc1F] | | 472.2 |

TABLE 1-continued

| Ex. No. | IUPAC name | structural formula | salt | MS |
|---|---|---|---|---|
| 110 | 1,5-anhydro-3-(((7-(4-((cyclopropylmethyl)carbamoyl)-3-fluorobenzyl)furo[3,2-b]pyridin-5-yl)carbonyl)amino)-2,3-dideoxy-L-threo-pentitol | | | 468.3 |
| 111 | 1,5-anhydro-2,3-dideoxy-3-(((7-(1-(3-fluoro-4-((2-methoxyethyl)carbamoyl)phenyl)-ethyl)furo[3,2-b]pyridin-5-yl)carbonyl)amino)-L-threo-pentitol | | | 486.3 |
| 112 | 1,5-anhydro-2,3-dideoxy-3-(((7-(1-(3-fluoro-4-((2-methoxyethyl)carbamoyl)phenyl)-ethyl)-2,3-dihydrofuro[3,2-b]pyridin-5-yl)carbonyl)amino)-L-threo-pentitol | | | 488.2 |
| 113 | 1,5-anhydro-2,3-dideoxy-3-(((7-((2-methyl-1-oxo-2,3-dihydro-1H-isoindol-5-yl)methyl)-2,3-dihydrofuro[3,2-b]pyridin-5-yl)carbonyl)amino)-L-threo-pentitol | | | 424.2 |

Formulation Example 1

| (1) | compound obtained in Example 1 | 10.0 g |
| --- | --- | --- |
| (2) | Lactose | 60.0 g |
| (3) | Cornstarch | 35.0 g |
| (4) | Gelatin | 3.0 g |
| (5) | Magnesium stearate | 2.0 g |

A mixture of the compound (10.0 g) obtained in Example 1, lactose (60.0 g) and cornstarch (35.0 g) is passed through a 1 mm mesh sieve and granulated by using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of sucrose, titanium dioxide, talc and gum arabic. The coated tablets are glazed with beeswax to give 1000 coated tablets.

Formulation Example 2

| (1) | compound obtained in Example 1 | 10.0 g |
| --- | --- | --- |
| (2) | Lactose | 70.0 g |
| (3) | Cornstarch | 50.0 g |
| (4) | Soluble starch | 7.0 g |
| (5) | Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

Experimental Example 1

Measurement of M1 Receptor Positive Allosteric Modulator (M1PAM) Activity

The activity of a test compound in the presence of acetylcholine at EC20 concentration (final concentration 0.8-1.0 nM), which affords an action corresponding to about 20% of the maximum activity, was measured as PAM activity. The method is as follows. CHO-K1 cells stably expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and assay buffer A containing calcium indicator (Recording medium (DOJINDO LABORATORIES), 0.1% BSA (Wako Pure Chemical Industries, Ltd.), 2.5 μg/mL Fluo-4 AM (DOJINDO LABORATORIES), 0.08% Pluronic F127 (DOJINDO LABORATORIES), 1.25 mM probenecid (DOJINDO LABORATORIES)) was added at 30 μL/well. The cells were left standing in the incubator at 37° C., 5% $CO_2$ for 30 min, and further left standing at room temperature for 30 min. A test compound prepared by diluting with assay buffer B (HBSS (Invitrogen), 20 mM HEPES (Invitrogen), 0.1% BSA) containing 3.2-4.0 nM acetylcholine was added at 10 μL/well, and the fluorescence was measured by FDSS/μCELL (Hamamatsu Photonics K.K.) for 1 min every for 1 second. With the definition that the amount of change in the fluorescence on addition of acetylcholine (final concentration 1 μM) is 100% and that on addition of DMSO instead of a test compound is 0%, the activity (%) of the test compound was calculated, and the inflection point in the concentration-dependent curve of the test compound was calculated as IP values. The results are shown in Table 2.

TABLE 2

| Example No. | IP value (nM) | activity (%) at 10 μM |
| --- | --- | --- |
| 3 | 13 | 100 |
| 8 | 7.9 | 100 |
| 16 | 10 | 100 |
| 18 | 12 | 97 |
| 20 | 0.88 | 98 |
| 21 | 1.6 | 100 |
| 22 | 1.7 | 106 |
| 23 | 1.5 | 99 |
| 27 | 4.5 | 100 |
| 28 | 2.3 | 101 |
| 31 | 1.4 | 101 |
| 34 | 2.4 | 100 |
| 36 | 1.5 | 96 |
| 40 | 1.6 | 98 |
| 43 | 2.4 | 110 |
| 44 | 1.5 | 105 |
| 46 | 4.3 | 107 |
| 47 | 1.8 | 101 |
| 48 | 1.1 | 103 |
| 49 | 2.9 | 104 |
| 51 | 0.88 | 104 |
| 55 | 0.63 | 107 |
| 56 | 42 | 106 |
| 57 | 1.1 | 99 |
| 60 | 1.6 | 104 |
| 61 | 1.8 | 104 |
| 64 | 2.4 | 109 |
| 65 | 8.5 | 106 |
| 70 | 1.2 | 99 |
| 74 | 1.5 | 108 |
| 76 | 3.5 | 109 |
| 77 | 3.2 | 108 |
| 81 | 5.3 | 108 |
| 82 | 6.4 | 110 |
| 88 | 7.6 | 111 |
| 89 | 25 | 110 |
| 90 | 1.4 | 113 |
| 96 | 11 | 107 |
| 97 | 5.1 | 107 |
| 100 | 3.8 | 103 |
| 102 | 2.7 | 107 |
| 105 | 4.3 | 105 |
| 109 | 2.4 | 107 |
| 111 | 8.8 | 107 |
| 113 | 21 | 109 |

Experimental Example 2

Rat Defecation Experiment

Male SD rats (5-6 weeks old) were used after an acclimation period for about 1 week. A test drug (1 mg/kg or 3 mg/kg) was suspended in 0.5% methylcellulose solution and orally administered at a volume of 5 mL/kg, and the number of feces 2 hr later was counted. Only 0.5% methylcellulose was administered to a solvent administration group.

The results are shown in Table 3. The results show mean±standard error.

TABLE 3

| Ex. No. | | solvent administra-tion group 0 mg/kg | dose 1 mg/kg | 3 mg/kg |
|---|---|---|---|---|
| 20 | number of feces 2 hr later | 4.9 ± 1.0 | 10.6 ± 1.3 | 12.1 ± 1.1 |
| 31 | number of feces 2 hr later | 3.5 ± 0.6 | 10.0 ± 1.4 | — |
| 76 | number of feces 2 hr later | 3.3 ± 1.0 | 8.3 ± 0.8 | 10.3 ± 0.9 |
| 77 | number of feces 2 hr later | 2.1 ± 0.6 | 13.9 ± 1.5 | 12.3 ± 1.6 |
| 102 | number of feces 2 hr later | 4.4 ± 1.1 | 8.9 ± 1.3 | 12.4 ± 0.9 |

Experimental Example 3

Rat PK Test

As the rat, 8-week-old male SD rats (Japan SLC, Inc.) were used. They were fed on a solid commercially available diet (CE-2, CLEA Japan, Inc.) and allowed to freely ingest tap water as the drinking water. An intravenous administration solution for the rats was prepared by weighing a test compound, dissolving same in dimethylacetamide (DMA) (Wako Pure Chemical Industries, Ltd.), adding the same volume of 1,3-butanediol (Wako Pure Chemical Industries, Ltd.) and mixing by stirring to give a DMA:1,3-butanediol (1:1, v/v) solution. An oral administration solution was prepared by weighing a test compound, pulverizing same in an agate mortar, and gradually adding 0.5 w/v % aqueous methylcellulose solution to give a suspension. For intravenous administration, the solution was administered into femoral vein of the rats at 0.1 mg/0.5 mL/kg (salt converted to free form). For oral administration, the suspension was administered to the rats at 1 mg/5 mL/kg (salt converted to free form). The cassette dosing method was used for the both administration routes, and the test compound was administered in the following manner.

Compound of Example 20 (intravenous: 8 compounds cassette administration, oral: 5 compounds cassette administration)
Compound of Example 22 (intravenous: 5 compounds cassette administration, oral: 5 compounds cassette administration)
Compound of Example 31 (intravenous: 10 compounds cassette administration, oral: 5 compounds cassette administration)
Compound of Example 36 (intravenous: 10 compounds cassette administration, oral: 5 compounds cassette administration)
Compound of Example 44 (intravenous: 10 compounds cassette administration, oral: 5 compounds cassette administration)
Compound of Example 55 (intravenous: 6 compounds cassette administration, oral: 4 compounds cassette administration)
Compound of Example 74 (intravenous: 10 compounds cassette administration, oral: 5 compounds cassette administration)
Compound of Example 76 (intravenous: 9 compounds cassette administration, oral: 4 compounds cassette administration)
Compound of Example 77 (intravenous: 10 compounds cassette administration, oral: 5 compounds cassette administration)
Compound of Example 102 (intravenous: 10 compounds cassette administration, oral: 5 compounds cassette administration)
Compound of Example 109 (intravenous: 7 compounds cassette administration, oral: 4 compounds cassette administration)

In the case of intravenous administration, blood samples were collected from the tail vein at 5, 10, 15, 30 min, 1, 2, 4, 8 hr after administration, an anticoagulation treatment with heparin sodium (Shimizu Pharmaceutical Co., Ltd.) was performed, and plasma was collected after centrifugation and subjected to the measurement of drug concentration. In the case of oral administration, blood samples were collected from the tail vein at 15, 30 min, 1, 2, 4, 8 hr after administration, an anticoagulation treatment with heparin sodium was performed, and plasma was collected after centrifugation and subjected to the measurement of drug concentration.

All drug concentrations were measured by LC-MS/MS analysis. For a pharmacokinetics test, the plasma (50 µL) was placed in a tube, acetonitrile (150 µL) containing internal standard solution was added and they were mixed on a vortex mixer. Thereafter, the mixture was centrifuged (5000 rpm, 5 min, 4° C.). The supernatant (60 µL) after centrifugation was added to 10 mmol/L ammonium formate (160 µL) added earlier and mixed therewith. This sample was injected to LC/MS/MS. The HPLC system used was Shimadzu LC-20A (Shimadzu Corporation), the column used was Unison UK-C18 HT (3.0 µm, 2.0×20 mm, Imtakt) at 50° C., and 10 mmol/L ammonium formate, 0.2% formic acid as mobile phase A and acetonitrile, 0.2% formic acid as mobile phase B were fed each at a flow rate of 1.2 mL/min under gradient conditions of (B concentration: 0 min→0.1 min, 5%, 0.1→0.75 min, 5-99%, 0.75→1.15 min, 99%, 1.15→1.16 min, 5%, 1.16→1.5 min, 5%). MS/MS used was AB Sciex TQ5500-MPX (Applied Biosystems).

The results are shown in Table 4.

Tmax: time to reach maximum plasma concentration
MRT: mean residence time
iv: intravenous administration
CL total: total clearance

TABLE 4

| Example No. | Tmax (h) | MRT iv (h) | CL total (mL/h/kg) |
|---|---|---|---|
| 20 | 2.0 | 1.8 | 246 |
| 22 | 2.0 | 1.9 | 280 |
| 31 | 1.0 | 1.5 | 200 |
| 36 | 1.3 | 1.9 | 327 |
| 44 | 1.3 | 1.3 | 286 |
| 55 | 1.7 | 0.6 | 1814 |
| 74 | 0.8 | 0.9 | 843 |
| 76 | 0.8 | 1.2 | 335 |

TABLE 4-continued

| Example No. | Tmax (h) | MRT iv (h) | CL total (mL/h/kg) |
|---|---|---|---|
| 77 | 1.0 | 0.8 | 488 |
| 102 | 1.0 | 0.9 | 703 |
| 109 | 1.0 | 1.5 | 404 |

Experimental Example 4

MDR1 Membrane Permeability Test

When MDR1 is expressed in excess in LLC-PK1 cell, which is a polar cell, MDR1 is localized in apical membrane (A), thus promoting transcellular transport from the basement membrane side (B) toward direction A. When a ratio to the transcellular transport in the opposite direction is taken and a ratio to a control cell in which a mock vector has been introduced is further taken, an efflux ratio of MDR1 to simple diffusion (corrected efflux ratio) is calculated. Similarly, when a brain/plasma concentration ratio in Mdr1(−/−) mouse is divided by a brain/plasma concentration ratio in wild-type mouse, an efflux ratio of Mdr1 to simple diffusion in blood-brain barrier (BBB) (Kp, brain ratio, higher value means lower central nervous system permeability) is calculated. Adachi Y. et al. (Reference 1) has reported a positive correlation between corrected efflux ratio and Kp, brain ratio (FIG. 5(C)), and efflux ratio in MDR1 expressing cell and Kp, brain ratio (FIG. 5(B)). That is, the report shows that a higher efflux ratio of MDR1 in vitro results in lower central nervous system permeability.

To confirm the central nervous system permeability of the compounds of the present invention, a MDR1 membrane permeability test was performed by the following method.

Digoxin and lucifer yellow (LY) were purchased from Sigma-Aldrich, Diclofenac, colchicine and alprenolol were purchased from Wako Pure Chemical Industries, Ltd., and other reagents used were commercially available products of special grade.

Human MDR1-expressing LLC-PK1 cells were cultured according to the report of Takeuchi et al. (Reference 2). Human MDR1-expressing LLC-PK1 cells were cultured in 10% fetal bovine serum (Invitrogen), 500 μg/ml G418 (Invitrogen), 150 ng/ml colchicine-containing M199 medium (Invitrogen) under 5% $CO_2$ conditions at 37° C.

Transcellular transport was performed according to the report of Sugimoto et al. (Reference 3). The cells were cultured for 3 days on HTS Transwell (registered trademark) 96 well permeable support (pore size 0.4 μm, 0.143 $cm^2$ surface area, Corning Life Sciences) having polyethylene terephthalate membrane on which the cells had been seeded at 3.45×10$^4$ cells/well. After preincubation in M199 medium (containing 10 mmol/L HEPES, 1% BSA, pH 7.4) for 30 min, a drug solution (10 μmol/L digoxin, 200 μmol/L LY, 10 μmol/L test compound) dissolved in M199 medium was added to the apical side or basolateral side of the Transwell by 75 or 250 μL each and the cells were cultured under 5% $CO_2$ conditions at 37° C. After 1 hr, the sample was collected from the side opposite to the side where the drug solution was added, and the concentration of the test compound was measured by LC-MS/MS. As an internal standard substance, 100 ng/mL alprenolol and diclofenac were used. The analysis conditions were as follows.

LC: UFLC LC-20 (Shimadzu)
MS/MS: API4000 (AB Sciex Instruments)
LC condition: gradient method

TABLE 5

| Time (min) | Pump B (%) |
|---|---|
| 0.02 | 5 |
| 0.40 | 95 |
| 0.80 | 95 |
| 0.81 | 5 |
| 1.50 | Stop |

Column: Unison UK-C18 HT (3.0 μm, 2.0×20 mm)
Column temperature: 50° C.
Flow rate: 0.7 mL/min (for 1.5 min run), 1.0 mL/min (for 1.0 min run)
Mobile phase A: 50 mM $CH_3COONH_4$:MeCN:water=1:1:8
Mobile phase B: 50 mM $CH_3COONH_4$:MeCN=1:9
Injection volume: 1-20 μL
  LY was measured by a fluorescence plate reader (Fluoroskan Ascent FL).
  $P_{app}$, A to B and $P_{app}$, B to A (apparent permeability) were calculated from the formula (1), and the efflux ratio (ER) was calculated from the formula (2).

$$P_{app} = \frac{Amount}{Area \times C_0 \times Time} \quad (1)$$

Amount: amount of transported digoxin/well
Area: surface area of cell monolayer (0.143 $cm^2$)
$C_0$: concentration of drug solution added
Time: incubation time $$ER = \frac{P_{app}, B \text{ to } A}{P_{app}, A \text{ to } B} \quad (2)$$

The results are shown in Table 6.

TABLE 6

| Example No. | MDR1 substrate screening 1 μM (MDRSUB1)/ Ratio (NUMBER) |
|---|---|
| 20 | 4.8 |
| 22 | 2.6 |
| 31 | 11 |
| 36 | 9.1 |
| 44 | 5.5 |
| 55 | 6.5 |
| 74 | 11 |
| 76 | 35 |
| 77 | 25 |
| 102 | 20 |
| 109 | 10 |

REFERENCES

1. Adachi Y. et al., Comparative studies on in vitro methods for evaluating in vivo function of MDR1 P-glycoprotein, Pharm. Res. 18:1660-1668, 2001
2. Takeuchi T., Yoshitomi S., Higuchi T., Ikemoto K., Niwa S., Ebihara T., Katoh M., Yokoi T. and Asahi S., Establishment and characterization of the transformants stably-expressing MDR1 derived from various animal species in LLC-PK1, Pharm. Res., 23(7):1460-1472, 2006
3. Sugimoto H., Hirabayashi H., Kimura Y., Furuta A., Amano N. and Moriwaki T., Quantitative investigation of the impact of P-glycoprotein inhibition on drug transport across blood-brain barrier in rats, Drug Metab. Dispos., 39(1):8-14, 2011

INDUSTRIAL APPLICABILITY

The compound of the present invention may have a cholinergic muscarinic M1 receptor positive allosteric modulator activity and may be useful as a medicament such as an agent for the prophylaxis or treatment of constipation and the like.

This application is based on patent application Nos. 2017-120859 and 2018-005960 filed in Japan, and patent application No. 62/683,418 filed in the United States of America, the entire contents of which are incorporated by reference herein.

The invention claimed is:

1. A compound represented by the formula (I):

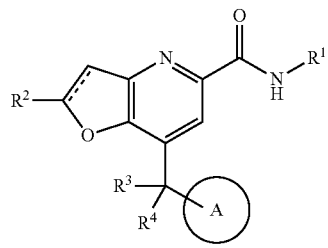

(I)

wherein
$R^1$ is an optionally substituted cyclic group;
$R^2$ is a hydrogen atom, a halogen atom, a cyano group, an optionally substituted $C_{1-6}$ alkyl group, or an optionally substituted $C_{1-6}$ alkoxy group;
----- is a single bond or a double bond;
ring A is a benzene ring substituted by (a) one halogen atom and (b) one mono- or di-$C_{1-6}$ alkyl-carbamoyl group optionally substituted by 1 or 2 substituents selected from (i) a $C_{1-6}$ alkoxy group, (ii) a $C_{3-10}$ cycloalkyl group, (iii) a 3- to 14-membered non-aromatic heterocyclic group, (iv) a $C_{6-14}$ aryl group optionally substituted by 1 to 3 hydroxy groups, (v) a $C_{1-6}$ alkoxy-carbonyl group, (vi) a carboxy group, (vii) a $C_{1-6}$ alkylthio group, (viii) a mono- or di-$C_{1-6}$ alkyl-carbamoyl group, and (ix) a 3- to 14-membered non-aromatic heterocyclylcarbonyl group; and
$R^3$ and $R^4$ are each independently a hydrogen atom, a halogen atom, a hydroxy group, an optionally substituted $C_{1-6}$ alkyl group, or an optionally substituted $C_{1-6}$ alkoxy group,
or a salt thereof.

2. The compound according to claim 1, wherein
$R^1$ is
(1) an optionally substituted 3- to 14-membered non-aromatic heterocyclic group, or
(2) an optionally substituted $C_{3-10}$ cycloalkyl group;
$R^2$ is a hydrogen atom or an optionally substituted $C_{1-6}$ alkyl group; and
$R^3$ and $R^4$ are each independently a hydrogen atom, a halogen atom or an optionally substituted $C_{1-6}$ alkyl group,
or a salt thereof.

3. The compound according to claim 1, wherein
$R^1$ is
(1) a 3- to 14-membered non-aromatic heterocyclic group optionally substituted by 1 to 3 hydroxy groups, or
(2) a $C_{3-10}$ cycloalkyl group optionally substituted by 1 to 3 substituents selected from a hydroxy group and a halogen atom;
$R^2$ is a hydrogen atom or a $C_{1-6}$ alkyl group; and
$R^3$ and $R^4$ are each independently a hydrogen atom, a halogen atom or a $C_{1-6}$ alkyl group,
or a salt thereof.

4. The compound according to claim 3, wherein
R is

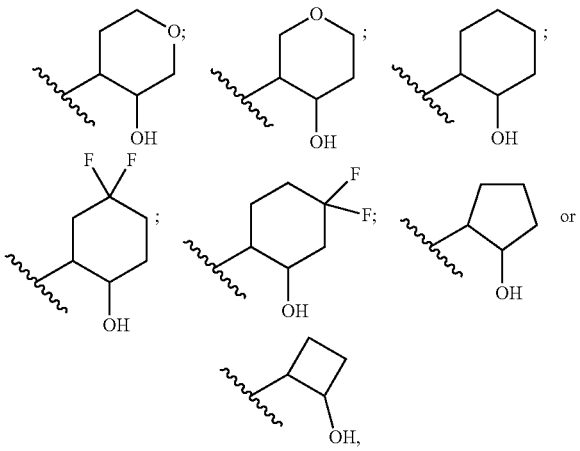

or a salt thereof.

5. The compound according to claim 3, wherein
ring A is
a benzene ring substituted by (a) one halogen atom and (b) one mono- or di-$C_{1-6}$ alkyl-carbamoyl group optionally substituted by 1 or 2 substituents selected from (i) a $C_{1-6}$ alkoxy group and (ii) a 3- to 14-membered non-aromatic heterocyclic group,
or a salt thereof.

6. The compound according to claim 1, wherein
$R^1$ is a 3- to 14-membered non-aromatic heterocyclic group substituted by one hydroxy group;
$R^2$ is a hydrogen atom;
ring A is
a benzene ring substituted by (a) one halogen atom and (b) one mono- or di-$C_{1-6}$ alkyl-carbamoyl group optionally substituted by 1 or 2 substituents selected from (i) a $C_{1-6}$ alkoxy group and (ii) a 3- to 14-membered non-aromatic heterocyclic group; and $R^3$ and $R^4$ are each independently a hydrogen atom or a halogen atom, or a salt thereof.

7. A pharmaceutical composition comprising the compound according to claim 1 or a salt thereof and a pharmaceutically acceptable carrier.

8. A method of cholinergic muscarinic M1 receptor positive allosteric modulation in a mammal, comprising administering an effective amount of the compound according to claim 1 or a salt thereof to said mammal.

9. A compound represented by the formula (I):

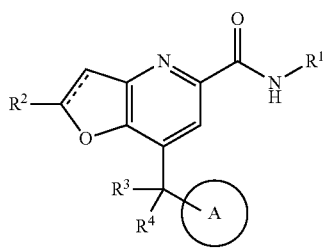

(I)

wherein:

$R^1$ is (1) a 3- to 14-membered non-aromatic heterocyclic group optionally substituted by 1 to 3 hydroxy groups, or (2) a $C_{3-10}$ cycloalkyl group optionally substituted by 1 to 3 substituents selected from a hydroxy group and a halogen atom;

$R^2$ is a hydrogen atom or a $C_{1-6}$ alkyl group;

----- is a single bond or a double bond;

ring A is

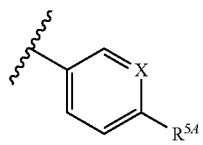

wherein $R^{5A}$ is a mono- or di-$C_{1-6}$ alkyl-carbamoyl group optionally substituted by 1 or 2 substituents selected from a $C_{1-6}$ alkoxy group and a 3- to 14-membered non-aromatic heterocyclic group;

X is $CR^{6A}$; and $R^{6A}$ is a hydrogen atom or a halogen atom; and $R^3$ and $R^4$ are each independently a hydrogen atom, a halogen atom or a $C_{1-6}$ alkyl group, or a salt thereof.

10. A method for the treatment of constipation in a mammal, comprising administering an effective amount of a compound represented by the formula (I):

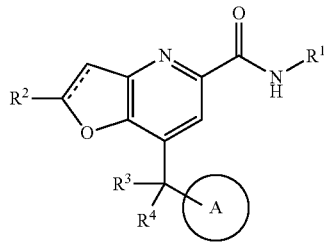

(I)

wherein $R^1$ is an optionally substituted cyclic group;

$R^2$ is a hydrogen atom, a halogen atom, a cyano group, an optionally substituted $C_{1-6}$ alkyl group, or an optionally substituted $C_{1-6}$ alkoxy group;

----- is a single bond or a double bond;

ring A is an optionally substituted ring; and $R^3$ and $R^4$ are each independently a hydrogen atom, a halogen atom, a hydroxy group, an optionally substituted $C_{1-6}$ alkyl group, or an optionally substituted $C_{1-6}$ alkoxy group, or a salt thereof to the mammal.

11. The method according to claim 10, wherein $R^1$ is (1) an optionally substituted 3- to 14-membered non-aromatic heterocyclic group, or (2) an optionally substituted $C_{3-10}$ cycloalkyl group;

$R^2$ is a hydrogen atom or an optionally substituted $C_{1-6}$ alkyl group;

ring A is (1) an optionally substituted benzene ring, (2) an optionally substituted 5- or 6-membered monocyclic aromatic heterocycle, (3) an optionally substituted 4- to 6-membered monocyclic non-aromatic heterocycle, or (4) an optionally substituted 9- to 14-membered fused polycyclic non-aromatic heterocycle; and $R^3$ and $R^4$ are each independently a hydrogen atom, a halogen atom or an optionally substituted $C_{1-6}$ alkyl group.

12. The method according to claim 10, wherein $R^1$ is (1) a 3- to 14-membered non-aromatic heterocyclic group optionally substituted by 1 to 3 hydroxy groups, or (2) a $C_{3-10}$ cycloalkyl group optionally substituted by 1 to 3 substituents selected from a hydroxy group and a halogen atom;

$R^2$ is a hydrogen atom or a $C_{1-6}$ alkyl group;

ring A is (1) a benzene ring optionally substituted by 1 to 3 substituents selected from (a) a halogen atom, (b) a $C_{1-6}$ alkoxy group, (c) a mono- or di-$C_{1-6}$ alkyl-carbamoyl group optionally substituted by 1 or 2 substituents selected from (i) a $C_{1-6}$ alkoxy group, (ii) a $C_{3-10}$ cycloalkyl group, (iii) a 3- to 14-membered non-aromatic heterocyclic group, (iv) a $C_{6-14}$ aryl group optionally substituted by 1 to 3 hydroxy groups, (v) a $C_{1-6}$ alkoxy-carbonyl group, (vi) a carboxy group, (vii) a $C_{1-6}$ alkylthio group, (viii) a mono- or di-$C_{1-6}$ alkyl-carbamoyl group, and (ix) a 3- to 14-membered non-aromatic heterocyclylcarbonyl group, (d) a mono- or di-$C_{3-10}$ cycloalkyl-carbamoyl group, (e) a $C_{6-14}$ aryl-carbamoyl group optionally substituted by 1 to 3 hydroxy groups, and
(f) a 5- to 14-membered aromatic heterocyclic group optionally substituted by 1 to 3 $C_{1-6}$ alkyl groups, (2) a 5- or 6-membered monocyclic aromatic heterocycle optionally substituted by 1 to 3 substituents selected from (a) a $C_{1-6}$ alkoxy group and (b) a 5- to 14-membered aromatic heterocyclic group optionally substituted by 1 to 3 $C_{1-6}$ alkyl groups, (3) a 4- to 6-membered monocyclic non-aromatic heterocycle optionally substituted by one oxo group, or (4) a 9- to 14-membered fused polycyclic non-aromatic heterocycle optionally substituted by 1 to 3 substituents selected from a $C_{1-6}$ alkyl group and an oxo group; and $R^3$ and $R^4$ are each independently a hydrogen atom, a halogen atom or a $C_{1-6}$ alkyl group.

13. The method according to claim 12, wherein $R^1$ is

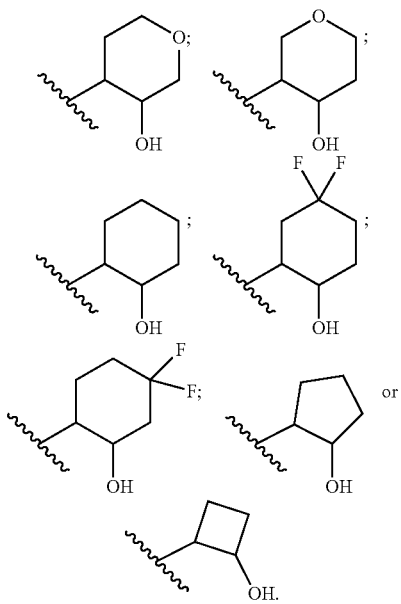

14. The method according to claim 12, wherein ring A is (1) a benzene ring substituted by 1 to 3 substituents selected from (a) a halogen atom, (b) a mono- or di-$C_{1-6}$ alkyl-carbamoyl group optionally substituted by 1 or 2 substituents selected from (i) a $C_{1-6}$ alkoxy group and (ii) a 3- to 14-membered non-aromatic heterocyclic group, and (c) a 5- to 14-membered aromatic heterocyclic group optionally substituted by 1 to 3 $C_{1-6}$ alkyl groups, or (2) a 5- or 6-membered monocyclic aromatic heterocycle substituted by one 5- to 14-membered aromatic heterocyclic group optionally substituted by 1 to 3 $C_{1-6}$ alkyl groups.

15. The method according to claim 12, wherein ring A is

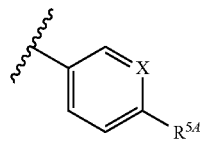

wherein $R^{5A}$ is a mono- or di-$C_{1-6}$ alkyl-carbamoyl group optionally substituted by 1 or 2 substituents selected from a $C_{1-6}$ alkoxy group and a 3- to 14-membered non-aromatic heterocyclic group;

X is $CR^{6A}$; and $R^{6A}$ is a hydrogen atom or a halogen atom.

16. The method according to claim 12, wherein ring A is

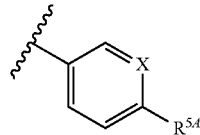

wherein $R^{5A}$ is a 5- to 14-membered aromatic heterocyclic group optionally substituted by 1 to 3 $C_{1-6}$ alkyl groups;

X is $CR^{6A}$ or N; and $R^{6A}$ is a hydrogen atom or a halogen atom.

17. The method according to claim 10, wherein $R^1$ is a 3- to 14-membered non-aromatic heterocyclic group substituted by one hydroxy group;

$R^2$ is a hydrogen atom;

ring A is (1) a benzene ring substituted by 1 to 3 substituents selected from (a) a halogen atom, (b) a mono- or di-$C_{1-6}$ alkyl-carbamoyl group optionally substituted by 1 or 2 substituents selected from (i) a $C_{1-6}$ alkoxy group and (ii) a 3- to 14-membered non-aromatic heterocyclic group, and (c) a 5- to 14-membered aromatic heterocyclic group optionally substituted by 1 to 3 $C_{1-6}$ alkyl groups, or (2) a 5- or 6-membered monocyclic aromatic heterocycle substituted by one 5- to 14-membered aromatic heterocyclic group optionally substituted by 1 to 3 $C_{1-6}$ alkyl groups; and $R^3$ and $R^4$ are each independently a hydrogen atom or a halogen atom.

* * * * *